(12) United States Patent
Klaassen et al.

(10) Patent No.: US 9,096,675 B2
(45) Date of Patent: Aug. 4, 2015

(54) CELL SUITABLE FOR FERMENTATION OF A MIXED SUGAR COMPOSITION

(75) Inventors: Paul Klaassen, Dordrecht (NL); Bianca Elisabeth Maria Gielesen, Maassluis (NL); Gijsberdina Pieternella Van Suylekom, Gravenmoer (NL); Wilbert Herman Marie Heijne, Dordrecht (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 13/642,114

(22) PCT Filed: Apr. 19, 2011

(86) PCT No.: PCT/EP2011/056232
§ 371 (c)(1),
(2), (4) Date: Nov. 20, 2012

(87) PCT Pub. No.: WO2011/131667
PCT Pub. Date: Oct. 27, 2011

(65) Prior Publication Data
US 2013/0059331 A1    Mar. 7, 2013

Related U.S. Application Data

(60) Provisional application No. 61/326,358, filed on Apr. 21, 2010, provisional application No. 61/326,351, filed on Apr. 21, 2010.

(30) Foreign Application Priority Data

Apr. 21, 2010  (EP) .................................... 10160622
Apr. 21, 2010  (EP) .................................... 10160647

(51) Int. Cl.
| | |
|---|---|
| C12P 7/06 | (2006.01) |
| C12N 1/20 | (2006.01) |
| C12N 9/00 | (2006.01) |
| C07K 14/395 | (2006.01) |
| C12N 1/36 | (2006.01) |

(52) U.S. Cl.
CPC ................ *C07K 14/395* (2013.01); *C12N 1/36* (2013.01); *Y02E 50/343* (2013.01)

(58) Field of Classification Search
CPC .............. C12N 1/18; C12N 9/90; C12N 9/92; C12N 1/20; C12N 1/22; C12N 9/001; C12N 9/1205; C12N 9/2462; C12N 15/81; C12N 15/815
USPC .................. 435/77, 47, 106, 224, 161, 252.3, 435/254.2, 183
See application file for complete search history.

(56) References Cited

U.S. PATENT DOCUMENTS 8,399,215 B2 *  3/2013  Klaassen et al. ................ 435/41
2012/0034648 A1 *  2/2012  Klaassen et al. ................ 435/43

FOREIGN PATENT DOCUMENTS

| WO | 2007143245 A2 | 12/2007 |
| WO | 2009/109633 | 9/2009 |
| WO | 2009109633 A1 | 9/2009 |

OTHER PUBLICATIONS

Written Opinion of ISR for PCT/EP2011/056232., Oct. 23, 2012.*
Matsushika et al., Appl Microbiol Biotechnol. 84:37-53, 2009.*
Karhumaa et al., Investigation of limiting metabolic steps in the utilization of xylose by recombinant *Saccharomyces cerevisiae* using metabolic engineering. Yeast. 22: 359-368, 2005.*
Hahn-Hagerdal et al., Towards industrial pentose-fermenting yeast strains. Appl Microbiol Biotechnol. 74:937-953, 2007.*
Karhumaa et al., Investigation of limiting metabolic steps in the utilization of xylose by recombinant *Saccharomyces cerevisiae* using metabolic engineering. Yeast. 22: 359-368, 2005, in Ids.*
Matsushika et al., Appl. Microbiol Biotechnol. Ethanol production from xylose in engineered *Saccharomyces cerevisiae* strains: current state and perspectives. 84:37-53, 2009.*
Madhavan et al., Xylose isomerase from polycentric fungus Orpinomyces: gene sequencing, cloning, and expression in *Saccharomyces cerevisiae* for bioconversion of xylose to ethanol. Appl. Microbiol. Biotechnol. 82:1067-1078, 2009.*
International Search Report for PCT/EP2011/056232 Mailed August 9, 2011.
Written Opinion for PCT/EP2011/056232 Mailed August 9, 2011.
Karhumaa et al., "Co-Utilization of L-Arabinose and D-Xylose by Laboratory and Industrial *Saccharomyces cerevisiae* Strains," Microbial Cell Factories, vol. 5, No. 1, pp. 1-11, (Apr. 10. 206)
Wahlbom et al., "Generation of the Improved Recombinant Xylose-Utilizing *Saccharomyces cerevisiae* TMB 3400 by Random Mutagenesis and Physiological Comparison With *Pichia stipitis* CBS 6054," FEMS Yeast Research, vol. 3, pp. 319-326, (Jan. 1, 2003).
Wang et al., "Establishment of a Xylose Metabolic Pathway in an Industrial Strain of *Saccharomyces cerevisiae*," Biotechnology Letters, vol. 26, No. 11, pp. 885-890, (Jun. 2004).
Lopes et al., "High-Copy-No. Integration Into the Ribosomal DNA of *Saccharomyces cerevisiae*: A New Vector for High-Level Expression," Gene, vol. 79, No. 2, pp. 199-206, (Jul. 15, 1989).
Torchia et al., "Disruption of Regulatory Gene GAL-80 in *Saccharomyces cerevisiae*: Effects.On Carbon-Controlled Regulation of the Galactose/Melibiose Pathway Genes," Molecular and Cellular Biology, vol. 4, No. 8, pp. 1521-1527, (Aug. 1984.)
Wisselink et al., "Engineering of *Saccharomyces cerevisiae* for Efficient Anaerobic Alcoholic Fermentation of L-Arabinose," Applied and Environmental Microbiology, vol. 73, No. 15, pp. 4881-4891, (Aug. 1, 2007).

(Continued)

*Primary Examiner* — Tekchand Saidha
(74) *Attorney, Agent, or Firm* — Miles & Stockbridge PC

(57) ABSTRACT

The present invention relates to a cell suitable for production of one or more fermentation product from a sugar composition comprising glucose, galactose, arabinose and xylose, wherein the cell comprises two to fifteen copies of one or more xylose isomerase gene or two to fifteen copies of one or more xylose reductase and xylitol dehydrogenase, and two to ten copies of araA, araB and araD, genes, wherein these genes are integrated into the cell genome.

16 Claims, 25 Drawing Sheets

(56) References Cited

OTHER PUBLICATIONS

Wisselink et al., "Novel Evolutionary Engineering Approach for Accelerated Utilization of Glucose, Xylose, and Arabinose Mixtures by Engineeered *Saccharomyces cerevisiae* Strains," Applied and Environmental Microbiology, vol. 75, No. 4, pp. 907-914, (Feb. 1, 2009).

Van Maris et al., "Alcoholic Fermentation of Carbon Sources in Biomass Hydrolysates by *Saccharomyces cerevisiae*: Current Status," Antonie van Leeuwenhoek, vol. 90, No. 4, pp. 391-418, (Oct. 11, 2006).

Wisselink, et al., "Engineering of *Saccharomyces cerevisiae* for Efficient Anaerobic Alcoholic Fermenation of L-Arabinose", Applied and Environmental Microbiology, Aug. 2007;73(15):4881-4891.

Wiedemann et al., "Codon-Optimized Bacterial Genes Improve L-Arabinose Fermentation in Recombinant *Saccharomycs cerevisiae*", Applied and Environmental Microbiology, Apr. 2008;74(7):2043-2050.

Wisselink, et al., "Novel Evolutionary Engineering Approach for Accelerated Utilization of Glucose, Xylose, and Arabinose Mixtures by Engineered *Saccharomyces cerevisiae* Strains", Applied and Environmental Microbiology, Feb. 2009;75(4):907-914.

Wang et al., "Establishment of a xylose metabolic pathway in an industrial strain of *Saccharomyces cerevisiae*", Biotechnology Letters, Jan. 2004;26:885-890.

Kuyper et al., Metabolic engineering of a xylose-isomerase-expressing *Saccharomyces cerevisiae* strain for rapid anaerobic xylose fermentation , FEMS Yeast Research. 2005;5:399-409.

Becker et al., "A Modified *Saccharomyces cerevisiae* Strain That Consumes L-Arabinose and Produces Ethanol," Applied and Environmental Microbiology, Jul. 2003;69(7):4144-4150.

Wisselink, et al., "Engineering of *Saccharomyces cerevisiae* for Efficient Anaerobic Alcoholic Fermentation of L-Arabinose", Applied and Environmental Microbiology, Aug. 2007;73(15):4881-4891.

Lopes, et al., "High-copy-number integration in to the ribosomal DNA of *Saccharomuces cerevisiae*: a new vector for high-level expression", Gene, 1999;79:199-206.

* cited by examiner

CELL SUITABLE FOR FERMENTATION OF A MIXED SUGAR COMPOSITION

CROSS REFERENCE TO RELATED APPLICATIONS

This application is a §371 National Stage Application of PCT/EP2011/056232, filed Apr. 19, 2011, which claims priority to European Application Nos. 10160622.6, filed Apr. 21, 2010; and Ser. No. 10/160,647.3, filed Apr. 21, 2010, and U.S. Provisional Application Nos. 61/326,351, filed Apr. 21, 2010; and 61/326,358, filed Apr. 21, 2010.

BACKGROUND OF THE INVENTION

1. Field of the Invention

The invention relates to a cell (herein also designated as mixed sugar cell), suitable for fermentation of a sugar composition comprising multiple C5 and/or C6 sugars (such composition is herein also designated as mixed sugar composition). The mixed sugar composition may originate from ligno-cellulosic material. The invention also relates to a process for the production of fermentation product from the mixed sugar composition using the mixed sugar cell.

2. Description of Related Art

Most of the ethanol produced as alternative for fossil fuels is currently from fermentation of corn starch and sugar cane based sucrose. In order to reach the ambitious goals for producing renewable fuels, new technologies are being developed for converting non-food biomass into fermentation products such as ethanol. Saccharomyces cerevisiae is the organism of choice in the ethanol industry, but it cannot utilize five-carbon sugars contained in the hemicellulose component of biomass feedstocks. Hemicellulose can make up to 20-30% of biomass, with xylose and arabinose being the most abundant C5 sugars. Heterologous expression of a xylose isomerase (XI) is an option for enabling yeast cells to metabolize and ferment xylose. Likewise, expression of bacterial genes araA, araB, and araD in S. cerevisiae strains results in utilization and efficient alcoholic fermentation of arabinose. Galactose is a C6-sugar that is also a sugar that is often present in lignocellulose, often in amounts (~4% of total sugars) that are not to be neglected for economic reasons.

J. van den Brink et al, Microbiology (2009)155, 1340-1350 discloses that glucose is the favoured carbon source for Saccharomyces cerevisiae and that upon switching from glucose limited fermentation conditions to galactose-excess condition under anaerobic condition, galactose was not consumed.

Sofar no process has been disclosed to convert glucose, arabinose, xylose and galactose, into a fermentation product in the same process with glucose.

SUMMARY

An object the invention is to provide a cell capable of converting glucose, xylose and galactose and mannose, i.e. a mix of four sugars, into a fermentation product. Another object of the invention is to such cell that is capable of converting glucose, xylose, arabinose, galactose and mannose, i.e. a mix of five sugars, into a fermentation product. A further object of the invention is to provide such above defined cell that is stable. A further object of the invention is to provide such above defined strain that is marker-free. A further object of the invention is to provide a process wherein glucose, xylose, arabinose, and galactose are simultaneously converted into a fermentation product. One or more of these objects are attained according to the invention.

The present invention provides a cell suitable for production of one or more fermentation product from a sugar composition comprising glucose, galactose, xylose, arabinose and mannose, wherein the cell comprises two to fifteen copies of one or more xylose isomerase gene or two to fifteen copies of one or more xylose reductase and xylitol dehydrogenase, and two to ten copies of araA, araB and araD, genes, wherein these genes are integrated into the cell genome.

The invention further provides to a process for the production of one or more fermentation product from a sugar composition comprising glucose, arabinose and xylose and optionally galactose and/or mannose comprising the following steps:

a) fermentation of the sugar composition in the presence of a mixed sugar cell comprising two to fifteen copies of one or more xylose isomerase gene and/or two to fifteen copies of one or more xylose reductase and xylitol dehydrogenase, wherein these genes are integrated into the genome; and b) recovery of the fermentation product.

In an embodiment, the mixed sugar cell is of the genus Saccharomyces. In an embodiment the mixed sugar cell is of the species Saccharomyces cerevisiae. In an embodiment, the fermentation product is ethanol.

BRIEF DESCRIPTION OF THE SEQUENCE LISTING

Figure 1:
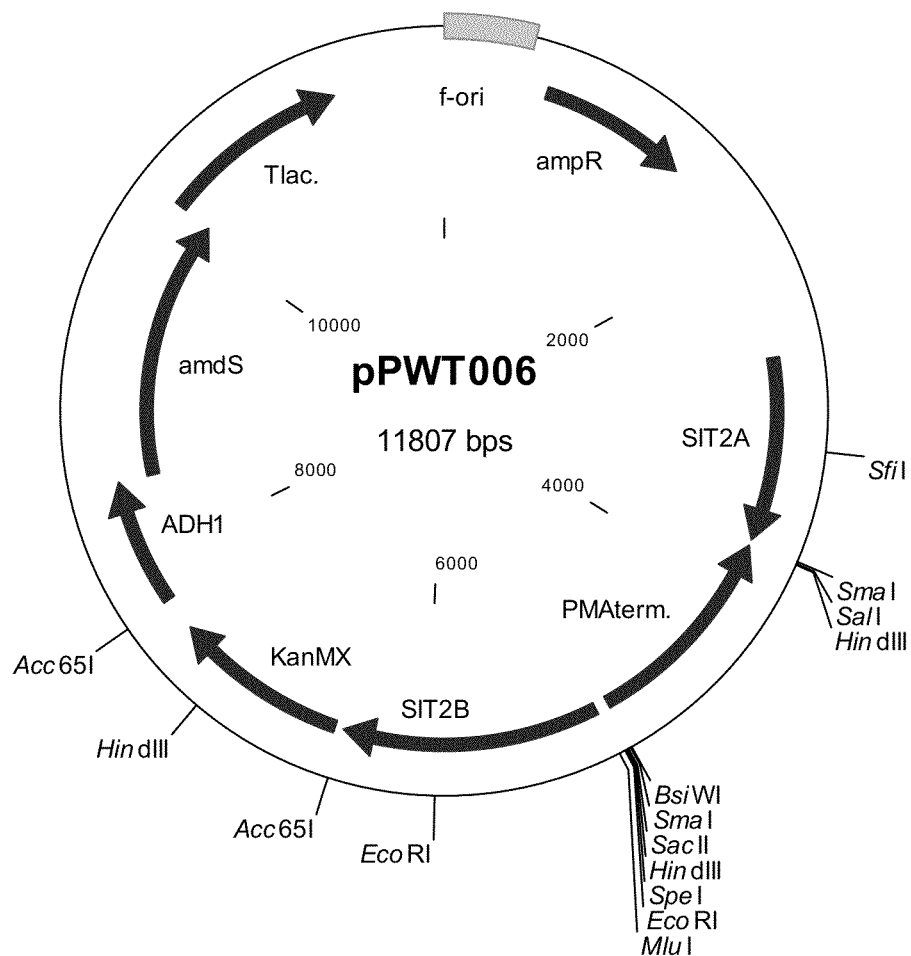
FIG. 1 sets out a physical map of plasmid pPWT006.

SEQ ID NO: 1 sets out the sequence of plasmid pPWT018
SEQ ID NO: 2 sets out the sequence of primer for checking the integration of pPWT018

SEQ ID NO: 3 sets out the sequence of primer for checking the integration of pPWT018 (with SEQ ID NO: 2) and for checking copy number pPWT018 (with SEQ ID NO: 4)

SEQ ID NO: 4 sets out the sequence of primer for checking copy number pPWT018

SEQ ID NO: 5 sets out the sequence of primer for checking the presence of pPWT018 in genome in combination with SEQ ID NO: 4

SEQ ID NO: 6 sets out the sequence of forward primer for generating the SIT2 probe SEQ ID NO: 7 sets out the sequence of reverse primer for generating the SIT2 probe SEQ ID NO: 8 sets out the sequence of plasmid pPWT080

SEQ ID NO: 9 sets out the sequence of forward primer for checking correct integration of pPWT080 at the end of the GRE3-locus (with SEQ ID NO: 10) and for checking the copy number plasmid pPWT080 (with SEQ ID NO: 11)

SEQ ID NO: 10 sets out the sequence of reverse primer for checking correct integration of pPWT080 at the end of the GRE3-locus SEQ ID NO: 11 sets out the sequence of reverse primer for checking the copy number plasmid pPWT080

SEQ ID NO: 12 sets out the sequence of forward primer for generating an RKI1-probe SEQ ID NO: 13 sets out the sequence of reverse primer for generating an RKI1-probe SEQ ID NO: 14 sets out sequence of plasmid pPWT042

SEQ ID NO: 15 sets out the sequence of primer for checking integration of pPWT042

SEQ ID NO: 16 sets out the sequence of primer for checking integration of pPWT042

SEQ ID NO: 17 sets out the sequence of primer for checking integration of pPWT042

SEQ ID NO: 18 sets out the sequence of primer for checking marker loss of pPWT042

SEQ ID NO: 19 sets out the sequence of primer for amplification of xylA-cassette SEQ ID NO: 20 sets out the sequence of primer for amplification of xylA-cassette SEQ ID NO: 21 sets out the sequence of primer for the amplification of kanMX-cassette SEQ ID NO: 22 sets out the sequence of primer for the amplification of the kanMX-cassette SEQ ID NO: 23 sets out the sequence of primer for quantitative PCR SEQ ID NO: 24 sets out the sequence of primer for quantitative PCR.

SEQ ID NO: 25 sets out the sequence of primer for quantitative PCR

SEQ ID NO: 26 sets out the sequence of primer for quantitative PCR.

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The various embodiments of the invention described herein may be cross-combined.

The Sugar Composition

The sugar composition according to the invention comprises glucose, arabinose and xylose. Any sugar composition may be used in the invention that suffices those criteria. Optional sugars in the sugar composition are galactose and mannose. In a preferred embodiment, the sugar composition is a hydrolysate of one or more lignocellulosic material.

cultural process, forestry wood waste, or a combination of any two or more thereof.

An overview of some suitable sugar compositions derived from lignocellulose and the sugar composition of their hydrolysates is given in table 1. The listed lignocelluloses include: corn cobs, corn fiber, rice hulls, melon shells, sugar beet pulp, wheat straw, sugar cane bagasse, wood, grass and olive pressings.

TABLE 1

Overview of sugar compositions from lignocellulosic materials.

| Lignocellulosic material | Gal | Xyl | Ara | Man | Glu | Rham | Sum | %. Gal. | Lit. |
| --- | --- | --- | --- | --- | --- | --- | --- | --- | --- |
| Corn cob a | 10 | 286 | 36 | | 227 | 11 | 570 | 1.7 | (1) |
| Corn cob b | 131 | 228 | 160 | | 144 | | 663 | 19.8 | (1) |
| Rice hulls a | 9 | 122 | 24 | 18 | 234 | 10 | 417 | 2.2 | (1) |
| Rice hulls b | 8 | 120 | 28 | | 209 | 12 | 378 | 2.2 | (1) |
| Melon Shells | 6 | 120 | 11 | | 208 | 16 | 361 | 1.7 | (1) |
| Sugar beet pulp | 51 | 17 | 209 | 11 | 211 | 24 | 523 | 9.8 | (2) |
| Wheat straw Idaho | 15 | 249 | 36 | | 396 | | 696 | 2.2 | (3) |
| Corn fiber | 36 | 176 | 113 | | 372 | | 697 | 5.2 | (4) |
| Cane Bagasse | 14 | 180 | 24 | 5 | 391 | | 614 | 2.3 | (5) |
| Corn stover | 19 | 209 | 29 | | 370 | | 626 | | (6) |
| Athel (wood) | 5 | 118 | 7 | 3 | 493 | | 625 | 0.7 | (7) |
| Eucalyptus (wood) | 22 | 105 | 8 | 3 | 445 | | 583 | 3.8 | (7) |
| CWR (grass) | 8 | 165 | 33 | | 340 | | 546 | 1.4 | (7) |
| JTW (grass) | 7 | 169 | 28 | | 311 | | 515 | 1.3 | (7) |
| MSW | 4 | 24 | 5 | 20 | 440 | | 493 | 0.9 | (7) |
| Reed Canary Grass Veg | 16 | 117 | 30 | 6 | 209 | 1 | 379 | 4.2 | (8) |
| Reed Canary Grass Seed | 13 | 163 | 28 | 6 | 265 | 1 | 476 | 2.7 | (9) |
| Olive pressing residu | 15 | 111 | 24 | 8 | 329 | | 487 | 3.1 | (9) |

Gal = galactose,
Xyl = xylose,
Ara = arabinose,
Man = mannose,
Glu = glutamate,
Rham = rhamnose.
The percentage galactose (% Gal) and literature source is given.

Lignocellulose herein includes hemicellulose and hemicellulose parts of biomass. Also lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agri- It is clear from table 1 that in these lignocelluloses a high amount of sugar is presence in de form of glucose, xylose, arabinose and galactose. The conversion of glucose, xylose, arabinose and galactose to fermentation product is thus of great economic importance. Also mannose is present in some lignocellulose materials be it usually in lower amounts than the previously mentioned sugars. Advantageously therefore also mannose is converted by the mixed sugar cell.

The Mixed Sugar Cell

The mixed sugar cell comprises two to fifteen copies of one or more xylose isomerase gene or two to fifteen copies of one or more xylose reductase and xylitol dehydrogenase, and two to ten copies of araA, araB and araD, genes, wherein these genes are integrated into the cell genome. I In one embodiment, the mixed sugar cell comprises about eight copies or eight copies of xylose isomerase, wherein these genes are integrated into the mixed sugar cell genome. In another embodiment, the mixed sugar cell comprises eight copies of a xylose reductase and xylitol dehydrogenase, wherein these genes are integrated into the mixed sugar cell genome.

The number of copies may be determined by the skilled person by any known method. In the examples, a suitable method is described.

The mixed sugar cell comprises two to ten copies of araA, araB and araD, genes, wherein these genes are integrated into the cell genome. t is able to ferment glucose, arabinose, xylose and galactose.

In an embodiment, the mixed sugar cell comprises two copies, three copies, four copies five copies, six copies, seven copies, eight copies, nine copies or ten copies, two to ten, two to nine, two to eight, two to seven, two to six, two to five, two to four, three to ten, three to nine, three to eight, three to seven, three to six, three to five, four to ten, four to nine, four to eight, four to seven or four to six copies of each of araA, araB and araD, genes, wherein these genes are integrated into the cell genome. In an embodiment the mixed sugar cell comprises about four, or four copies of each of araA, araB and araD genes, wherein these genes are integrated into the cell genome.

In an embodiment the number of copies of xylose isomerase gene or xylose reductase and xylitol dehydrogenase in to mixed sugar cell is eight or nine. In an embodiment the number of copies of araA, araB and araD genes in the mixed sugar cell is 3 or 4.

In an embodiment, the cell is capable of converting 90% or more glucose, xylose arabinose, galactose and mannose available, into a fermentation product. In an embodiment, cell is capable of converting 91% or more, 92% or more, 94% or more, 95% or more, 96% or more, 97% or more, 98% or more or 100% of all glucose, xylose arabinose, galactose and mannose available, into a fermentation product.

In an embodiment, the cell has a disruption or deletion of the GAL80 gene.

In one embodiment of the invention the mixed sugar cell is able to ferment one or more additional sugar, preferably C5 and/or C6 sugar e.g. mannose. In an embodiment of the invention the mixed sugar cell comprises one or more of: a xylA-gene, XYL1 gene and XYL2 gene and/or XKS1-gene, to allow the mixed sugar cell to ferment xylose; deletion of the aldose reductase (GRE3) gene; overexpression of PPP-genes TAL1, TKL1, RPE1 and RKI1 to allow the increase of the flux through the pentose phosphate pass-way in the cell.

In an embodiment, the mixed sugar cell is an industrial cell, more preferably an industrial yeast. An industrial cell and industrial yeast cell may be defined as follows. The living environments of (yeast) cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. In one embodiment, the industrial mixed sugar cell is constructed on the basis of an industrial host cell, wherein the construction is conducted as described hereinafter. Examples of industrial yeast (*S. cerevisiae*) are ETHANOL RED® (*S. cerevisiae*; Fermentis) FERMIOL® (*S. cerevisiae*; DSM) and THERMOSACC® (*S. cerevisiae*; Lallemand).

In an embodiment the mixed sugar cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxymethylfurfural. Examples or phenolic compounds are vanillin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions. For phenolics: several tens of milligrams per liter, up to a gram per liter, depending on the feedstock, the pretreatment and the hydrolysis conditions.

The mixed sugar strains according to the invention are inhibitor tolerant, i.e. they can withstand common inhibitors at the level that they typically have with common pretreatment and hydrolysis conditions, so that the mixed sugar strains can find broad application, i.e. it has high applicability for different feedstock, different pretreatment methods and different hydrolysis conditions.

In one embodiment, the industrial mixed sugar cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

In an embodiment, the mixed sugar cell is marker-free. As used herein, the term "marker" refers to a gene encoding a trait or a phenotype which permits the selection of, or the screening for, a host cell containing the marker. Marker-free means that markers are essentially absent in the mixed sugar cell. Being marker-free is particularly advantageous when antibiotic markers have been used in construction of the mixed sugar cell and are removed thereafter. Removal of markers may be done using any suitable prior art technique, e.g intramolecular recombination. A suitable method of marker removal is illustrated in the examples.

A mixed sugar cell may be able to convert plant biomass, celluloses, hemicelluloses, pectins, rhamnose, galactose, frucose, maltose, maltodextrines, ribose, ribulose, or starch, starch derivatives, sucrose, lactose and glycerol, for example into fermentable sugars. Accordingly, a mixed sugar cell may express one or more enzymes such as a cellulase (an endo-cellulase or an exocellulase), a hemicellulase (an endo- or exo-xylanase or arabinase) necessary for the conversion of cellulose into glucose monomers and hemicellulose into xylose and arabinose monomers, a pectinase able to convert pectins into glucuronic acid and galacturonic acid or an amylase to convert starch into glucose monomers.

The mixed sugar cell further may comprise those enzymatic activities required for conversion of pyruvate to a desired fermentation product, such as ethanol, butanol, lactic acid, 3-hydroxy-propionic acid, acrylic acid, acetic acid, succinic acid, citric acid, fumaric acid, malic acid, itaconic acid, an amino acid, 1,3-propane-diol, ethylene, glycerol, a β-lactam antibiotic or a cephalosporin.

In an embodiment, the mixed sugar cell a cell that is naturally capable of alcoholic fermentation, preferably, anaerobic alcoholic fermentation. A mixed sugar cell preferably has a high tolerance to ethanol, a high tolerance to low pH (i.e. capable of growth at a pH lower than about 5, about 4, about 3, or about 2.5) and towards organic and/or a high tolerance to elevated temperatures.

Any of the above characteristics or activities of a mixed sugar cell may be naturally present in the cell or may be introduced or modified by genetic modification.

Construction of the Mixed Sugar Strain

According to an embodiment, the genes may be introduced in the mixed sugar cell by introduction into a host cell:
a) a cluster consisting of the genes araA, araB and araD under control of a strong constitutive promoter
b) a cluster consisting of PPP-genes TAL1, TKL1, RPE1 and RKI1, optionally under control of strong constitutive promoter; and deletion of an aldose reductase gene;
c) a cluster consisting of a xylA-gene and a XKS1-gene under control of strong constitutive promoter;
d) a construct comprising a xylA gene under control of a strong constitutive promoter, which has the ability to integrate into the genome on multiple loci;
and adaptive evolution to produce the mixed sugar cell. The above cell may be constructed using recombinant expression techniques.

Recombinant Expression

The mixed sugar cell is a recombinant cell. That is to say, a mixed sugar cell comprises, or is transformed with or is genetically modified with a nucleotide sequence that does not naturally occur in the cell in question.

Techniques for the recombinant expression of enzymes in a cell, as well as for the additional genetic modifications of a mixed sugar cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635 574, WO 98/46772, WO 99/60102, WO 00/37671, WO90/14423, EP-A-0481008, EP-A-0635574 and U.S. Pat. No. 6,265,186.

Typically, the nucleic acid construct may be a plasmid, for instance a low copy plasmid or a high copy plasmid. The cell according to the present invention may comprise a single or multiple copies of the nucleotide sequence encoding a enzyme, for instance by multiple copies of a nucleotide construct or by use of construct which has multiple copies of the enzyme sequence.

The nucleic acid construct may be maintained episomally and thus comprise a sequence for autonomous replication, such as an autosomal replication sequence sequence. A suitable episomal nucleic acid construct may e.g. be based on the yeast 2p or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265,186).

Most episomal or 2μ plasmids are relatively unstable, being lost in approximately $10^{-2}$ or more cells after each generation. Even under conditions of selective growth, only 60% to 95% of the cells retain the episomal plasmid. The copy number of most episomal plasmids ranges from 20-100 per cell of cir$^+$ hosts. However, the plasmids are not equally distributed among the cells, and there is a high variance in the copy number per cell in populations. Strains transformed with integrative plasmids are extremely stable, even in the absence of selective pressure. However, plasmid loss can occur at approximately $10^{-3}$ to $10^{-4}$ frequencies by homologous recombination between tandemly repeated DNA, leading to looping out of the vector sequence. Preferably, the vector design in the case of stable integration is thus, that upon loss of the selection marker genes (which also occurs by intramolecular, homologous recombination) that looping out of the integrated construct is no longer possible. Preferably the genes are thus stably integrated. Stable integration is herein defined as integration into the genome, wherein looping out of the integrated construct is no longer possible. Preferably selection markers are absent. Typically, the enzyme encoding sequence will be operably linked to one or more nucleic acid sequences, capable of providing for or aiding the transcription and/or translation of the enzyme sequence.

The term "operably linked" refers to a juxtaposition wherein the components described are in a relationship permitting them to function in their intended manner. For instance, a promoter or enhancer is operably linked to a coding sequence the said promoter or enhancer affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

The promoter that could be used to achieve the expression of a nucleotide sequence coding for an enzyme according to the present invention, may be not native to the nucleotide sequence coding for the enzyme to be expressed, i.e. a promoter that is heterologous to the nucleotide sequence (coding sequence) to which it is operably linked. The promoter may, however, be homologous, i.e. endogenous, to the host cell.

Promoters are widely available and known to the skilled person. Suitable examples of such promoters include e.g. promoters from glycolytic genes, such as the phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), and the enolase promoter (ENO). Other promoters, both constitutive and inducible, and enhancers or upstream activating sequences will be known to those of skill in the art. The promoters used in the host cells of the invention may be modified, if desired, to affect their control characteristics. Suitable promoters in this context include both constitutive and inducible natural promoters as well as engineered promoters, which are well known to the person skilled in the art. Suitable promoters in eukaryotic host cells may be GAL7, GAL10, or GAL1, CYC1, HIS3, ADH1, PGL, PH05, GAPDH, ADC1, TRP1, URA3, LEU2, ENO1, TPI1, and AOX1. Other suitable promoters include PDC1, GPD1, PGK1, TEF1, and TDH3.

In a mixed sugar cell, the 3'-end of the nucleotide acid sequence encoding enzyme preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. Usually a nucleotide sequence encoding the enzyme comprises a terminator. Preferably, such terminators are combined with mutations that prevent nonsense mediated mRNA decay in the host mixed sugar cell (see for example: Shirley et al., 2002, Genetics 161:1465-1482).

The transcription termination sequence further preferably comprises a polyadenylation signal.

Optionally, a selectable marker may be present in a nucleic acid construct suitable for use in the invention. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Examples of suitable antibiotic resistance markers include e.g. dihydrofolate reductase, hygromycin-B-phosphotransferase, 3'-O-phosphotransferase II (kanamycin, neomycin and G418 resistance). Antibiotic resistance markers may be most convenient for the transformation of polyploid host cells, Also non-antibiotic resistance markers may be used, such as auxotrophic markers (URA3, TRP1, LEU2) or the S. pombe TPI gene (described by Russell P R, 1985, Gene 40: 125-130). In a preferred embodiment the host cells transformed with the nucleic acid constructs are marker gene free. Methods for constructing recombinant marker gene free microbial host cells are disclosed in EP-A-0 635 574 and are based on the use of bidirectional markers such as the A. nidulans amdS (acetamidase) gene or the yeast URA3 and LYS2 genes. Alternatively, a screenable marker such as Green Fluorescent Protein, lacL, luciferase, chloramphenicol acetyltransferase, beta-glucuronidase may be incorporated into the nucleic acid constructs of the invention allowing to screen for transformed cells.

Optional further elements that may be present in the nucleic acid constructs suitable for use in the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence.

The recombination process may thus be executed with known recombination techniques. Various means are known to those skilled in the art for expression and overexpression of enzymes in a mixed sugar cell. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively, overexpression of enzymes in the host cells of the invention may be achieved by using a promoter that is not native to the sequence coding for the enzyme to be overexpressed, i.e. a promoter that is heterologous to the coding sequence to which it is operably linked. Although the promoter preferably is heterologous to the coding sequence to which it is operably linked, it is also preferred that the promoter is homologous, i.e. endogenous to the host cell. Preferably the heterologous promoter is capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters.

In an embodiment, the mixed sugar cell is markerfree, which means that no auxotrophic or dominant markers, in particular antibiotic resistance markers, are present in the genome or extra-chromosomally.

The coding sequence used for overexpression of the enzymes mentioned above may preferably be homologous to the host cell. However, coding sequences that are heterologous to the host may be used.

Overexpression of an enzyme, when referring to the production of the enzyme in a genetically modified cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Preferably in a host, an enzyme to be overexpressed is overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

Adaptation

Adaptation is the evolutionary process whereby a population becomes better suited (adapted) to its habitat or habitats. This process takes place over several to many generations, and is one of the basic phenomena of biology.

The term adaptation may also refer to a feature which is especially important for an organism's survival. Such adaptations are produced in a variable population by the better suited forms reproducing more successfully, by natural selection.

Changes in environmental conditions alter the outcome of natural selection, affecting the selective benefits of subsequent adaptations that improve an organism's fitness under the new conditions. In the case of an extreme environmental change, the appearance and fixation of beneficial adaptations can be essential for survival. A large number of different factors, such as e.g. nutrient availability, temperature, the availability of oxygen, etcetera, can drive adaptive evolution.

Fitness

There is a clear relationship between adaptedness (the degree to which an organism is able to live and reproduce in a given set of habitats) and fitness. Fitness is an estimate and a predictor of the rate of natural selection. By the application of natural selection, the relative frequencies of alternative phenotypes will vary in time, if they are heritable.

Genetic Changes

When natural selection acts on the genetic variability of the population, genetic changes are the underlying mechanism. By this means, the population adapts genetically to its circumstances. Genetic changes may result in visible structures, or may adjust the physiological activity of the organism in a way that suits the changed habitat.

It may occur that habitats frequently change. Therefore, it follows that the process of adaptation is never finally complete. In time, it may happen that the environment changes gradually, and the species comes to fit its surroundings better and better. On the other hand, it may happen that changes in the environment occur relatively rapidly, and then the species becomes less and less well adapted. Adaptation is a genetic process, which goes on all the time to some extent, also when the population does not change the habitat or environment.

The Adaptive Evolution

The mixed sugar cells may in their preparation be subjected to adaptive evolution. A mixed sugar cell may be adapted to sugar utilisation by selection of mutants, either spontaneous or induced (e.g. by radiation or chemicals), for growth on the desired sugar, preferably as sole carbon source, and more preferably under anaerobic conditions. Selection of mutants may be performed by techniques including serial transfer of cultures as e.g. described by Kuyper et al. (2004, FEMS Yeast Res. 4: 655-664) or by cultivation under selective pressure in a chemostat culture. E.g. in a preferred host cell at least one of the genetic modifications described above, including modifications obtained by selection of mutants, confer to the host cell the ability to grow on the xylose as carbon source, preferably as sole carbon source, and preferably under anaerobic conditions. When XI is used as gene to convert xylose, preferably the cell produce essentially no xylitol, e.g. the xylitol produced is below the detection limit or e.g. less than about 5, about 2, about 1, about 0.5, or about 0.3% of the carbon consumed on a molar basis.

Adaptive evolution is also described e.g. in Wisselink H. W. et al, Applied and Environmental Microbiology August 2007, p. 4881-4891

In one embodiment of adaptive evolution a regimen consisting of repeated batch cultivation with repeated cycles of consecutive growth in different media is applied, e.g. three media with different compositions (glucose, xylose, and arabinose; xylose and arabinose. See Wisselink et al. (2009) Applied and Environmental Microbiology, February 2009, p. 907-914.

Yeast Transformation and Genetic Stability

Genetic engineering, i.e. transformation of yeast cells with recombinant DNA, became feasible for the first time in 1978 [Beggs, 1978; Hinnen et al., 1978]. Recombinant DNA technology in yeast has established itself since then. A multitude of different vector constructs are available. Generally, these plasmid vectors, called shuttle vectors, contain genetic material derived from E. coli vectors consisting of an origin of replication and a selectable marker (often the βlactamase gene, ampR), which enable them to be propagated in E. coli prior to transformation into yeast cells. Additionally, the shuttle vectors contain a selectable marker for selection in yeast. Markers can be genes encoding enzymes for the synthesis of a particular amino acid or nucleotide, so that cells carrying the corresponding genomic deletion (or mutation) are complemented for auxotrophy or auxotrophy. Alternatively, these vectors contain heterologous dominant resistance markers, which provides recombinant yeast cells (i.e. the cells that have taken up the DNA and express the marker gene) resistance towards certain antibiotics, like g418 (Geneticin), hygromycinB or phleomycin. In addition, these vectors may contain a sequence of (combined) restriction sites (multiple cloning site or MCS) which will allow to clone foreign DNA into these sites, although alternative methods exist as well.

Traditionally, four types of shuttle vectors can be distinguished by the absence or presence of additional genetic elements:

Integrative plasmids (YIp) which by homologous recombination are integrated into the host genome at the locus of the marker or another gene, when this is opened by restriction and the linearized DNA is used for transformation of the yeast cells. This generally results in the presence of one copy of the foreign DNA inserted at this particular site in the genome.

Episomal plasmids (YEp) which carry part of the 2μ plasmid DNA sequence necessary for autonomous replication in yeast cells. Multiple copies of the transformed plasmid are propagated in the yeast cell and maintained as episomes.

Autonomously replicating plasmids (YRp) which carry a yeast origin of replication (ARS, autonomously replicated sequence) that allows the transformed plasmids to be propagated several hundred-fold.

CEN plasmids (YCp) which carry in addition to an ARS sequence a centromeric sequence (derived from one of the nuclear chromosomes) which normally guarantees stable mitotic segregation and usually reduces the copy number of self-replicated plasmid to just one.

These plasmids are being introduced into the yeast cells by transformation. Transformation of yeast cells may be achieved by several different techniques, such as permeabilization of cells with lithium acetate (Ito et al, 1983) and electroporation methods.

In commercial application of recombinant microorganisms, plasmid instability is the most important problem. Instability is the tendency of the transformed cells to lose their engineered properties because of changes to, or loss of, plasmids. This issue is discussed in detail by Zhang et al (Plasmid stability in recombinant *Saccharomyces cerevisiae*. Biotechnology Advances, Vol. 14, No. 4, pp. 401-435, 1996). Strains transformed with integrative plasmids are extremely stable, even in the absence of selective pressure (Fred Sherman, *Yeast Genetics, in THE ENCYCLOPEDIA OF MOLECULAR BIOLOGY AND MOLECULAR MEDICINE*. 1997; 6:302-305; Sherman, "Getting Started with Yeast," *Methods Enymol*. 2002; 350:3-41, and references therein).

The heterologous DNA is usually introduced into the organism in the form of extra-chromosomal plasmids (YEp, YCp and YRp). Unfortunately, it has been found with both bacteria and yeasts that the new characteristics may not be retained, especially if the selection pressure is not applied continuously. This is due to the segregational instability of the hybrid plasmid when recombinant cells grow for a long period of time. This leads to population heterogeneity and clonal variability, and eventually to a cell population in which the majority of the cells has lost the properties that were introduced by transformation. If vectors with auxotrophic markers are being used, cultivation in rich media often leads to rapid loss of the vector, since the vector is only retained in minimal media. The alternative, the use of dominant antibiotic resistance markers, is often not compatible with production processes. The use of antibiotics may not be desired from a registration point of view (the possibility that trace amounts of the antibiotic end up in the end product) or for economic reasons (costs of the use of antibiotics at industrial scale).

Loss of vectors leads to problems in large scale production situations. Alternative methods for introduction of DNA do exist for yeasts, such as the use of integrating plasmids (YIp). The DNA is integrated into the host genome by recombination, resulting in high stability. (Gaunt, P. Stability of recombinant plasmids in yeast. Journal of Biotechnology 9 (1988) 173-192). We have found that an integration method using the host transposons are a good alternative.

Transposons

According to the invention, two to fifteen xylose isomerase gene or xylose reductase gene and xylitol dehydrogenase is integrated into the mixed sugar cell genome. In an embodiment the Initial introduction (i.e. before adaptive evolution)

of multiple copies be executed in any way known in the art that leads to introduction of the genes. In an embodiment, this may be accomplished using a vector with parts homologous to repeated sequences (transposons), of the host cell. When the host cell is a yeast cell, suitable repeated sequences are the long terminal repeats (LTR) of the Ty element, known as delta sequence.

Ty elements fall into two rather similar subfamilies called Ty1 and Ty2. These elements are about 6 kilobases (kb) in length and are bounded by long terminal repeats (LTR), sequences of about 335 base pairs (Boeke J D et al, The *Saccharomyces cerevisiae* Genome Contains Functional and Nonfunctional Copies of Transposon Ty1. Molecular and Cellular Biology, April 1988, p. 1432-1442 Vol. 8, No. 4). In the fully sequenced *S. cerevisiae* strain, S288c, the most abundant transposons are Ty1 (31 copies) and Ty2 (13 copies) (Gabriel A, Dapprich J, Kunkel M, Gresham D, Pratt S C, et al. (2006) Global mapping of transposon location. PLoS Genet. 2(12): e212.doi:10.1371/journal.pgen.0020212). These transposons consist of two overlapping open reading frames (ORFS), each of which encode several proteins. The coding regions are flanked by the aforementioned, nearly identical LTRs. Other, but less abundant and more distinct Ty elements in *S. cereviaise* comprise Ty3, Ty4 and Ty5. For each family of full-length Ty elements there are an order of magnitude more solo LTR elements dispersed through the genome. These are thought to arise by LTR-LTR recombination of full-length elements, with looping out of the internal protein encoding regions.

The retrotransposition mechanism of the Ty retrotransposon has been exploited to integrate multiple copies throughout the genome (Boeke et al., 1988; Jacobs et al., 1988). The long terminal repeats (LTR) of the Ty element, known as delta sequences, are also good targets for integration by homologous recombination as they exist in about 150-200 copies that are either Ty associated or solo sites (Boeke, 1989; Kingsman and Kingsman, 1988). (Parekh R. N. (1996). An Integrating Vector for Tunable, High Copy, Stable Integration into the Dispersed Ty DELTA Sites of *Saccharomyces cerevisiae*. Biotechnol. Prog. 1996, 12, 16-21). By adaptive evolution, the number of copies may change.

The Host Cell

The host cell may be any host cell suitable for production of a useful product. A host cell may be any suitable cell, such as a prokaryotic cell, such as a bacterium, or a eukaryotic cell. Typically, the cell will be a eukaryotic cell, for example a yeast or a filamentous fungus.

Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form.

Yeasts may either grow by budding of a unicellular thallus or may grow by fission of the organism. A preferred yeast as a mixed sugar cell may belong to the genera *Saccharomyces, Kluyveromyces, Candida, Pichia, Schizosaccharomyces, Hansenula, Kloeckera, Schwanniomyces* or *Yarrowia*. Preferably the yeast is one capable of anaerobic fermentation, more preferably one capable of anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the suitable for use as a cell of the present invention are morphologically, physiologically, and genetically distinct from yeasts.

Filamentous fungal cells may be advantageously used since most fungi do not require sterile conditions for propagation and are insensitive to bacteriophage infections. Vegetative growth by filamentous fungi is by hyphal elongation and carbon catabolism of most filamentous fungi is obligately aerobic. Preferred filamentous fungi as a host cell may belong to the genus *Aspergillus, Trichoderma, Humicola, Acremoniurra, Fusarium* or *Penicillium*. More preferably, the filamentous fungal cell may be a *Aspergillus niger, Aspergillus oryzae*, a *Penicillium chrysogenum*, or *Rhizopus oryzae* cell.

In one embodiment the host cell may be yeast.

Preferably the host is an industrial host, more preferably an industrial yeast. An industrial host and industrial yeast cell may be defined as follows. The living environments of yeast cells in industrial processes are significantly different from that in the laboratory. Industrial yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of *Saccharomyces cerevisiae*. Under adverse industrial conditions, the environmental tolerant strains should allow robust growth and production. Industrial yeast strains are generally more robust towards these changes in environmental conditions which may occur in the applications they are used, such as in the baking industry, brewing industry, wine making and the ethanol industry. Examples of industrial yeast (*S. cerevisiae*) are ETHANOL RED® (*S. cerevisiae*. Fermentis) FERMIOL® (*S. cerevisiae*; DSM) and THERMOSACC® (*S. cerevisiae*; Lallemand).

In an embodiment the host is inhibitor tolerant. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant *S. cerevisiae* strain ATCC 26602 was selected.

araA, araB and araD Genes

A mixed sugar cell is capable of using arabinose. A mixed sugar cell is therefore, be capable of converting L-arabinose into L-ribulose and/or xylulose 5-phosphate and/or into a desired fermentation product, for example one of those mentioned herein.

Organisms, for example *S. cerevisiae* strains, able to produce ethanol from L-arabinose may be produced by modifying a cell introducing the araA (L-arabinose isomerase), araB (L-ribulokinase) and araD (L-ribulose-5-P4-epimerase) genes from a suitable source. Such genes may be introduced into a mixed sugar cell is order that it is capable of using arabinose. Such an approach is given is described in WO2003/095627. araA, araB and araD genes from *Lactobacillus plantanum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591.

PPP-Genes

A mixed sugar cell may comprise one or more genetic modifications that increases the flux of the pentose phosphate pathway. In particular, the genetic modification(s) may lead to an increased flux through the non-oxidative part of the pentose phosphate pathway. A genetic modification that causes an increased flux of the non-oxidative part of the pentose phosphate pathway is herein understood to mean a modification that increases the flux by at least a factor of about 1.1, about 1.2, about 1.5, about 2, about 5, about 10 or about 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and subtracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e. $Q_s=\mu/Y_{xs}$). Therefore the increased flux of the non-oxidative part of the pentose phosphate pathway may be deduced from the increase in maximum growth rate under these conditions unless transport (uptake is limiting).

One or more genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase. Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

The enzyme "ribulose 5-phosphate epimerase" (EC 5.1.3.1) is herein defined as an enzyme that catalyses the epimerisation of D-xylulose 5-phosphate into D-ribulose 5-phosphate and vice versa. The enzyme is also known as phosphoribulose epimerase; erythrose-4-phosphate isomerase; phosphoketopentose 3-epimerase; xylulose phosphate 3-epimerase; phosphoketopentose epimerase; ribulose 5-phosphate 3-epimerase; D-ribulose phosphate-3-epimerase; D-ribulose 5-phosphate epimerase; D-ribulose-5-P 3-epimerase; D-xylulose-5-phosphate 3-epimerase; pentose-5-phosphate 3-epimerase; or D-ribulose-5-phosphate 3-epimerase. A ribulose 5-phosphate epimerase may be further defined by its amino acid sequence. Likewise a ribulose 5-phosphate epimerase may be defined by a nucleotide sequence encoding the enzyme as well as by a nucleotide sequence hybridising to a reference nucleotide sequence encoding a ribulose 5-phosphate epimerase. The nucleotide sequence encoding for ribulose 5-phosphate epimerase is herein designated RPE1.

The enzyme "ribulose 5-phosphate isomerase" (EC 5.3.1.6) is herein defined as an enzyme that catalyses direct isomerisation of D-ribose 5-phosphate into D-ribulose 5-phosphate and vice versa. The enzyme is also known as phosphopentosisomerase; phosphoriboisomerase; ribose phosphate isomerase; 5-phosphoribose isomerase; D-ribose 5-phosphate isomerase; D-ribose-5-phosphate ketol-isomerase; or D-ribose-5-phosphate aldose-ketose-isomerase. A ribulose 5-phosphate isomerase may be further defined by its amino acid sequence. Likewise a ribulose 5-phosphate isomerase may be defined by a nucleotide sequence encoding the enzyme as well as by a nucleotide sequence hybridising to a reference nucleotide sequence encoding a ribulose 5-phosphate isomerase. The nucleotide sequence encoding for ribulose 5-phosphate isomerase is herein designated RKI1.

The enzyme "transketolase" (EC 2.2.1.1) is herein defined as an enzyme that catalyses the reaction: D-ribose 5-phosphate+D-xylulose 5-phosphate<->sedoheptulose 7-phosphate+D-glyceraldehyde 3-phosphate and vice versa. The enzyme is also known as glycolaldehydetransferase or sedoheptulose-7-phosphate:D-glyceraldehyde-3-phosphate glycolaldehydetransferase. A transketolase may be further defined by its amino acid. Likewise a transketolase may be defined by a nucleotide sequence encoding the enzyme as well as by a nucleotide sequence hybridising to a reference nucleotide sequence encoding a transketolase. The nucleotide sequence encoding for transketolase is herein designated TKL1.

The enzyme "transaldolase" (EC 2.2.1.2) is herein defined as an enzyme that catalyses the reaction: sedoheptulose 7-phosphate+D-glyceraldehyde 3-phosphate<->D-erythrose 4-phosphate+D-fructose 6-phosphate and vice versa. The enzyme is also known as dihydroxyacetonetransferase; dihydroxyacetone synthase; formaldehyde transketolase; or sedoheptulose-7-phosphate:D-glyceraldehyde-3-phosphate glyceronetransferase. A transaldolase may be further defined by its amino acid sequence. Likewise a transaldolase may be defined by a nucleotide sequence encoding the enzyme as well as by a nucleotide sequence hybridising to a reference nucleotide sequence encoding a transaldolase. The nucleotide sequence encoding for transketolase from is herein designated TAL1.

Xylose Isomerase or Xylose Reductase Genes

According to the invention, two to fifteen copies of one or more xylose isomerase gene and/or one or more xylose reductase and xylitol dehydrogenase are introduced into the genome of the host cell. The presence of these two to fifteen genetic elements confers on the cell the ability to convert xylose by isomerisation or reduction.

In one embodiment, the two to fifteen copies of one or more xylose isomerase gene are introduced into the genome of the host cell.

A "xylose isomerase" (EC 5.3.1.5) is herein defined as an enzyme that catalyses the direct isomerisation of D-xylose into D-xylulose and/or vice versa. The enzyme is also known as a D-xylose ketoisomerase. A xylose isomerase herein may also be capable of catalysing the conversion between D-glucose and D-fructose (and accordingly may therefore be referred to as a glucose isomerase). A xylose isomerase herein may require a bivalent cation, such as magnesium, manganese or cobalt as a cofactor.

Accordingly, such a mixed sugar cell is capable of isomerizing xylose to xylulose. The ability of isomerizing xylose to xylulose is conferred on the host cell by transformation of the host cell with a nucleic acid construct comprising a nucleotide sequence encoding a defined xylose isomerase. A mixed sugar cell isomerizes xylose into xylulose by the direct isomerisation of xylose to xylulose.

A unit (U) of xylose isomerase activity may herein be defined as the amount of enzyme producing 1 nmol of xylulose per minute, under conditions as described by Kuyper et al. (2003, FEMS Yeast Res. 4: 69-78).

The Xylose isomerise gene may have various origin, such as for example *Pyromyces* sp. as disclosed in WO2006/009434. Other suitable origins are *Bacteroides*, in particular *Bacteroides uniformis* as described in PCT/EP2009/52623, *Bacillus*, in particular *Bacillus stearothermophilus* as described in PCT/EP2009/052625.

In another embodiment, the two to fifteen copies of one or more xylose reductase and xylitol dehydrogenase genes are introduced into the genome of the host cell. In this embodiment the conversion of xylose is conducted in a two step conversion of xylose into xylulose via a xylitol intermediate as catalysed by xylose reductase and xylitol dehydrogenase, respectively. In an embodiment thereof xylose reductase (XR), xylitol dehydrogenase (XDH), and xylokinase (XK) may be overexpressed, and optionally one or more of genes encoding NADPH producing enzymes are up-regulated and one or more of the genes encoding NADH consuming enzymes are up-regulated, as disclosed in WO 2004085627.

XKS1 Gene

A mixed sugar cell may comprise one or more genetic modifications that increase the specific xylulose kinase activity. Preferably the genetic modification or modifications causes overexpression of a xylulose kinase, e.g. by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell is a nucleotide sequence encoding a polypeptide with xylulose kinase activity.

The enzyme "xylulose kinase" (EC 2.7.1.17) is herein defined as an enzyme that catalyses the reaction ATP+D-xylulose=ADP+D-xylulose 5-phosphate. The enzyme is also known as a phosphorylating xylulokinase, D-xylulokinase or ATP:D-xylulose 5-phosphotransferase. A xylulose kinase of the invention may be further defined by its amino acid sequence. Likewise a xylulose kinase may be defined by a nucleotide sequence encoding the enzyme as well as by a nucleotide sequence hybridising to a reference nucleotide sequence encoding a xylulose kinase.

In a mixed sugar cell, a genetic modification or modifications that increase(s) the specific xylulose kinase activity may be combined with any of the modifications increasing the flux of the pentose phosphate pathway as described above. This is not, however, essential.

Thus, a host cell may comprise only a genetic modification or modifications that increase the specific xylulose kinase activity. The various means available in the art for achieving and analysing overexpression of a xylulose kinase in the host cells of the invention are the same as described above for enzymes of the pentose phosphate pathway. Preferably in the host cells of the invention, a xylulose kinase to be overexpressed is overexpressed by at least a factor of about 1.1, about 1.2, about 1.5, about 2, about 5, about 10 or about 20 as compared to a strain which is genetically identical except for the genetic modification(s) causing the overexpression. It is to be understood that these levels of overexpression may apply to the steady state level of the enzyme's activity, the steady state level of the enzyme's protein as well as to the steady state level of the transcript coding for the enzyme.

Aldose reductase (GRE3) Gene Deletion

In the embodiment, where XI is used as gene to convert xylose, it may be advantageous to reduce aldose reducatase activity. A mixed sugar cell may therefore comprise one or more genetic modifications that reduce unspecific aldose reductase activity in the host cell. Preferably, unspecific aldose reductase activity is reduced in the host cell by one or more genetic modifications that reduce the expression of or inactivates a gene encoding an unspecific aldose reductase. Preferably, the genetic modification(s) reduce or inactivate the expression of each endogenous copy of a gene encoding an unspecific aldose reductase in the host cell (herein called GRE3 deletion). Mixed sugar cells may comprise multiple copies of genes encoding unspecific aldose reductases as a result of di-, poly- or aneu-ploidy, and/or the host cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or down-stream of the coding sequence, the (partial) deletion or inactivation of which results in a reduction of expression of unspecific aldose reductase activity in the host cell.

A nucleotide sequence encoding an aldose reductase whose activity is to be reduced in the host cell is a nucleotide sequence encoding a polypeptide with aldose reductase activity.

Thus, a host cell comprising only a genetic modification or modifications that reduce(s) unspecific aldose reductase activity in the host cell is specifically included in the invention.

The enzyme "aldose reductase" (EC 1.1.1.21) is herein defined as any enzyme that is capable of reducing xylose or xylulose to xylitol. In the context of the present invention an aldose reductase may be any unspecific aldose reductase that is native (endogenous) to a host cell of the invention and that is capable of reducing xylose or xylulose to xylitol. Unspecific aldose reductases catalyse the reaction:

The enzyme has a wide specificity and is also known as aldose reductase; polyol dehydrogenase (NADP$^+$); alditol:NADP oxidoreductase; alditol:NADP$^+$ 1-oxidoreductase; NADPH-aldopentose reductase; or NADPH-aldose reductase.

A particular example of such an unspecific aldose reductase that is endogenous to *S. cerevisiae* and that is encoded by the GRE3 gene (Traff et al., 2001, Appl. Environ. Microbiol. 67: 5668-74). Thus, an aldose reductase of the invention may be further defined by its amino acid sequence. Likewise an aldose reductase may be defined by the nucleotide sequences encoding the enzyme as well as by a nucleotide sequence hybridising to a reference nucleotide sequence encoding an aldose reductase.

Sequence Identity

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably.

The terms "homology", "percent homology", "percent identity" or "percent similarity" are used interchangeably herein. For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids/based or amino acids. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences (amino acid or nucleotide) is calculated according to the definition of "longest-identity" as can be carried out by using the program NEEDLE.

The protein sequences used in the present invention can further be used as a "query sequence" to perform a search against sequence databases, for example to identify other family members or related sequences. Such searches can be performed using the BLAST programs. Software for performing BLAST analyses is publicly available through the National Center for Biotechnology Information (NCBI). BLASTP is used for amino acid sequences and BLASTN for nucleotide sequences. The BLAST program uses as defaults:

Cost to open gap: default=5 for nucleotides/11 for proteins
Cost to extend gap: default=2 for nucleotides/1 for proteins
Penalty for nucleotide mismatch: default=-3
Reward for nucleotide match: default=1
Expect value: default=10
Wordsize: default=11 for nucleotides/28 for megablast/3 for proteins Furthermore the degree of local identity (homology) between the amino acid sequence query or nucleic acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

Bioproducts Production

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmo-tolerance, capability of anaerobic growth, and of course its high alcoholic fermentative capacity. Preferred yeast species as host cells include *S. cerevisiae*, *S. bulderi*, *S. barnetti*, *S. exiguus*, *S. uvarum*, *S. diastaticus*, *K. lactis*, *K. marxianus* or *K. fragilis*.

A mixed sugar cell may be a cell suitable for the production of ethanol. A mixed sugar cell may, however, be suitable for the production of fermentation products other than ethanol Such non-ethanolic fermentation products include in principle any bulk or fine chemical that is producible by a eukaryotic microorganism such as a yeast or a filamentous fungus.

A mixed sugar cell that may be used for production of non-ethanolic fermentation products is a host cell that contains a genetic modification that results in decreased alcohol dehydrogenase activity.

In an embodiment the mixed sugar cell may be used in a process wherein sugars originating from lignocellulose are converted into ethanol.

Liqnocellulose

Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes. The conversion with the cellulases may be executed at ambient temperatures or at higher tempatures, at a reaction time to release sufficient amounts of sugar(s). The result of the enzymatic hydrolysis is hydrolysis product comprising C5/C6 sugars, herein designated as the sugar composition.

Fermentation

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

Thus, in a preferred anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, citric acid, malic acid, fumaric acid, an amino acid, 1,3-propane-diol, ethylene, glycerol, a β-lactam antibiotic and a cephalosporin.

The fermentation process is preferably run at a temperature that is optimal for the cell. Thus, for most yeasts or fungal host cells, the fermentation process is performed at a temperature which is less than about 42° C., preferably less than about 38° C. For yeast or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also relates to a process for producing a fermentation product.

The fermentation process according to the present invention may be run under aerobic and anaerobic conditions. In an embodiment, the process is carried out under micro-aerophilic or oxygen limited conditions.

An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention may comprise recovery of the fermentation product.

In a preferred process the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as yeasts are well known in the art The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more.

According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 gl/L-200 g/L, 40 g/L-200 g/L, 50 g/L-200 g/L, 60 g/L-200 g/L, 70 g/L-200 g/L, 80 g/L-200 g/L, 90 g/L, 80 g/L-200 g/L.

Product Concentration in SSF mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose)

The theoretical maximum yield (Yps max in gr product per gram glucose) of a fermentation product can be derived from textbook biochemistry. For ethanol, 1 mole of glucose (180 gr) yields according to normal glycolysis fermentation pathway in yeast 2 moles of ethanol ($=2\times46=92$ gr ethanol. The theoretical maximum yield of ethanol on glucose is therefore $92/180=0.511$ gr ethanol/gr glucose.

For Butanol (MW 74 gr/mole) or iso butanol, the theoretical maximum yield is 1 mole of butanol per mole of glucose. So Yps max for (iso-)butanol=$74/180=0.411$ gr (iso-)butanol/gr glucose.

For lactic acid the fermentation yield for homolactic fermentation is 2 moles of lactic acid (MW=90 gr/mole) per mole of glucose. According to this stoichiometry, the Yps max=1 gr lactic acid/gr glucose.

For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L Accordingly, the invention provides a method for the preparation of a fermentation product, which method comprises:

a. degrading lignocellulose using a method as described herein; and
b. fermenting the resulting material, thereby to prepare a fermentation product.

Fermentation Product

The fermentation product of the invention may be any useful product. In one embodiment, it is a product selected from the group consisting of ethanol, n-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase. For example the fermentation products may be produced by cells according to the invention, following prior art cell preparation methods and fermentation processes, which examples however should herein not be construed as limiting. n-butanol may be produced by cells as described in WO2008121701 or WO2008086124; lactic acid as described in US2011053231 or US2010137551; 3-hydroxy-propionic acid as described in WO2010010291; acrylic acid as described in WO2009153047 acetic acid as described in . . . , succinic acid as described in . . . cells of the fumarase-deficient mutant fermenting glucose accumulated extracellular fumaric acid (***Note still to be added.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol.

The following examples illustrate the invention:

Unless indicated otherwise, the methods described in here are standard biochemical techniques. Examples of suitable general methodology textbooks include Sambrook et al., Molecular Cloning, a Laboratory Manual (1989) and Ausubel et al., Current Protocols in Molecular Biology (1995), John Wiley & Sons, Inc.

Medium Composition

Growth experiments: *Saccharomyces cerevisiae* strains are grown on medium having the following composition: 0.67% (w/v) yeast nitrogen base or synthetic medium (Verduyn et al., Yeast 8:501-517, 1992) and glucose, arabinose, galactose or xylose, or a combination of these substrates, at varying concentrations (see examples for specific details; concentrations in % weight over volume (w/v)). For agar plates the medium is supplemented with 2% (w/v) bacteriological agar.

Ethanol Production

Pre-cultures were prepared by inoculating 25 ml Verduyn-medium (Verduyn et al., Yeast 8:501-517, 1992) supplemented with 2% glucose in a 100 ml shake flask with a frozen stock culture or a single colony from agar plate. After incubation at 30° C. in an orbital shaker (280 rpm) for approximately 24 hours, this culture was harvested and used for determination of $CO_2$ evolution and ethanol production experiments.

Cultivations for ethanol production were performed at 30° C. in 100 ml synthetic model medium (Verduyn-medium (Verduyn et al., Yeast 8:501-517, 1992) with 5% glucose, 5% xylose, 3.5% arabinose and 1% galactose) in the BAM (Biological Activity Monitor, Halotec, The Netherlands). The pH of the medium was adjusted to 4.2 with 2 M $NaOH/H_2SO4$ prior to sterilisation. The synthetic medium for anaerobic cultivation was supplemented with 0.01 g $l^{-1}$ ergosterol and 0.42 g $l^{-1}$ Tween 80 dissolved in ethanol (Andreasen and Stier. J. Cell Physiol. 41:23-36, 1953; and Andreasen and Stier. J. Cell Physiol. 43:271-281, 1954). The medium was inoculated at an initial OD600 of approximately 2. Cultures were stirred by a magnetic stirrer. Anaerobic conditions developed rapidly during fermentation as the cultures were not aerated. $CO_2$ production was monitored constantly. Sugar conversion and product formation (ethanol, glycerol) was analyzed by NMR. Growth was monitored by following optical density of the culture at 600 nm on a LKB Ultrospec K spectrophotometer.

Transformation of *S. cerevisiae*

Transformation of *S. cerevisiae* was done as described by Gietz and Woods (2002; Transformation of the yeast by the LiAc/SS carrier DNA/PEG method. Methods in Enzymology 350: 87-96).

Colony PCR

A single colony isolate was picked with a plastic toothpick and resuspended in 50 μl milliQ water. The sample was incubated for 10 minutes at 99° C. 5 μl of the incubated sample was used as a template for the PCR reaction, using PHUSION® DNA polymerase (Finnzymes) according to the instructions provided by the supplier.

PCR Reaction Conditions:

| step 1 | 3' | 98° C. | |
|---|---|---|---|
| step 2 | 10" | 98° C. | |
| step 3 | 15" | 58° C. | repeat step 2 to 4 for 30 cycles |
| step 4 | 30" | 72° C. | |
| step 5 | 4' | 72° C. | |
| step 6 | 30" | 20° C. | |

Chromosomal DNA Isolation

Yeast cells were grown in YEP-medium containing 2% glucose, in a rotary shaker (overnight, at 30° C. and 280 rpm in an orbital shaker). 1.5 ml of these cultures were transferred to an Eppendorf tube and centrifuged for 1 minute at maximum speed. The supernatant was decanted and the pellet was resuspended in 200 μl of YCPS (0.1% SB3-14 (Sigma Aldrich, the Netherlands) in 10 mM Tris.HCl pH 7.5; 1 mM EDTA) and 1 μl RNase (20 mg/ml RNase A from bovine pancreas, Sigma, the Netherlands). The cell suspension was incubated for 10 minutes at 65° C. The suspension was centrifuged in an Eppendorf centrifuge for 1 minute at 7000 rpm. The supernatant was discarded. The pellet was carefully dissolved in 200 μl CLS (25 mM EDTA, 2% SDS) and 1 μl RNase A. After incubation at 65° C. for 10 minutes, the suspension was cooled on ice. After addition of 70 μl PPS (10M ammonium acetate) the solutions were thoroughly mixed on a Vortex mixer. After centrifugation (5 minutes in Eppendorf centrifuge at maximum speed), the supernatant was mixed with 200 μl ice-cold isopropanol. The DNA readily precipitated and was pelleted by centrifugation (5 minutes, maximum speed). The pellet was washed with 400 μl ice-cold 70% ethanol. The pellet was dried at room temperature and dissolved in 50 μl TE (10 mM Tris.HCl pH7.5, 1 mM EDTA).

Transformation of Yeast Cells by Electroporation

Yeast cells were cultured by inoculating 25 ml of YEP-medium containing 2% glucose with a single yeast colony. The flask was incubated overnight at 30° C.

The optical density at 600 nm was determined and the amount needed to obtain an optical density of 0.2 was transferred to 100 ml YEP-medium with 2% glucose. The cells were grown for 4 to 5 hours, in order to reach an optical density of approximately 1.2 to 1.3, which corresponds to 2 to 3 generations. Cells were collected by centrifugation and resuspended in 28 ml TE (10 mM Tris.HCl, 1 mM EDTA, pH 7.5). 3 ml of a 1M LiAC solution (set at pH 7.5 with concentrated HAc) was added. The cells were gently shaken in a rotary incubator (150 rpm, 30° C.) for 45 minutes. After addition of 500 μl of a 1M DTT (dithiothreitol) solution, the cells were incubated once more under these conditions, for 15 minutes. The volume was made up to 100 ml with sterile, ice-cold milliQ water. The cells were collected by centrifugation.

The supernatant was discarded and the pelleted cells were washed with 50 ml of sterile, ice cold milliQ water, and collected by centrifugation. A subsequent washing treatment was done with 30 ml of an ice cold 1M sorbitol solution. After centrifugation, the supernatant was discarded and the cell pellet was resuspended in 4 ml of an ice cold 1M sorbitol solution. After centrifugation, the supernatant was discarded and the cell pellet was resuspended in 300 μl of an ice cold 1M sorbitol solution.

For each transformation, 40 μl of the cell suspension is transferred into ice cold Eppendorf tubes. The transforming DNA and 5 μg salmon sperm DNA (as carrier DNA) is added, together in a maximum volume of 20 μl. The DNA should be dissolved in TE. Carefully tap the Eppendorf tube in order to mix the content gently. Transfer the content to a pre-chilled (on ice) electroporation cuvette with a gap of 0.2 cm. Apply a pulse (using e.g. a BioRad Electroporation Device) at 1.5 kV, 200 Ohm and 25 μF. The pulse time should be around 5 ms. Transfer the cells immediately to 200 μl 1M sorbitol. Add 4 ml of YEP 2% glucose and incubate at 30° C. for 1 hour. Collect cells by centrifugation, discard the supernatant and resuspend the pellet in 4 ml of 1M sorbitol. Collect cells by centrifugation, discard the supernatant and resuspend the pellet in 300 μl of 1M sorbitol. Dilute the cells as appropriate and spread on selective plates or use in selective media.

Yeast Application Test on Real Hydrolysates

Dilute acid pretreated samples of corn stover and wheat straw were enzymatically hydrolyzed by using an experimental broad spectrum cellulase preparation at 60° C. for 3 days (72 hours). The pH at the start of the hydrolysis was 5.0. The dry matter content at the start of the hydrolysis was 10% w/w.

The conditions for the hydrolysis of pretreated corn fiber samples was essentially the same, except that the hydrolysis temperature was 50° C. and the dry matter content at the start of the hydrolysis was 13.8%.

After hydrolysis (72 hrs), the samples were allowed to be cooled to room temperature. The pH was adjusted to 5.5 using 10% NaOH. Subsequently, 1 milliliter of a 200 gram per liter $(NH_4)_2SO_4$ and 1 milliliter of 100 gram per liter $KH_2PO_4$ was added. Finally, yeast samples were added corresponding to a yeast dry matter content of 1 gram yeast per kilogram hydrolysate. The CO2 evolution in time was followed using the AFM (Alcohol Fermentation Monitor; HaloteC Instruments BV, Veenendaal, the Netherlands). Experiments were performed in at least triplicate, for 72 hours at 33° C. One of these is sampled at regular intervals in order to be able to analyze ethanol formation and residual sugar concentrations. These data can be used to calculate fermentation yields. The broth of the other two experiments is not sampled. Instead, at the end of the fermentation the broth is distilled using a Buchi K-355 distillation unit at 45% steam for 15 minutes. The alcohol produced is being determined using an Anton Paar DMA 5000 density meter (Anton Paar Benelux BVBA, Dongen, the Netherlands).

Quantitative PCR

Quantitative PCR reactions were performed to determine the copy number of the genes that were present in the genome, especially in case of the xylose isomerase genes. To this end, the Bio-Rad iCycler iQ system from Bio-Rad (Bio-Rad Laboratories, Hercules, Calif., USA) was used. The iQ SYBR Green Supermix (Bio-Rad) was used. Experiments were set up as suggested in the manual of the provider. As primers for the detection of the xylose isomerase gene, primers of SEQ ID NO: 23 and SEQ ID NO: 24 were used.

The PCR conditions were as follows:
3 minutes incubation at 95° C.
40 cycles: 10 seconds at 95° C.
   45 seconds at 58° C.
   45 seconds at 72° C.
1 minute incubation at 95° C.
1 minute incubation at 65° C.

The melting curve is being determined by starting to measure fluorescence at 65° C. for 10 seconds. The temperature is increased every 10 seconds with 0.5° C., until a temperature of 95° C. is reached. From the reads, the copy number of the gene of interest may be calculated and/or estimated. The method has its limitations with respect to an accurate determination of the copy number above a certain threshold, as will be appreciated by those skilled in the art.

Example 1

Construction of Strain BIE104A2P1

Figure 2:
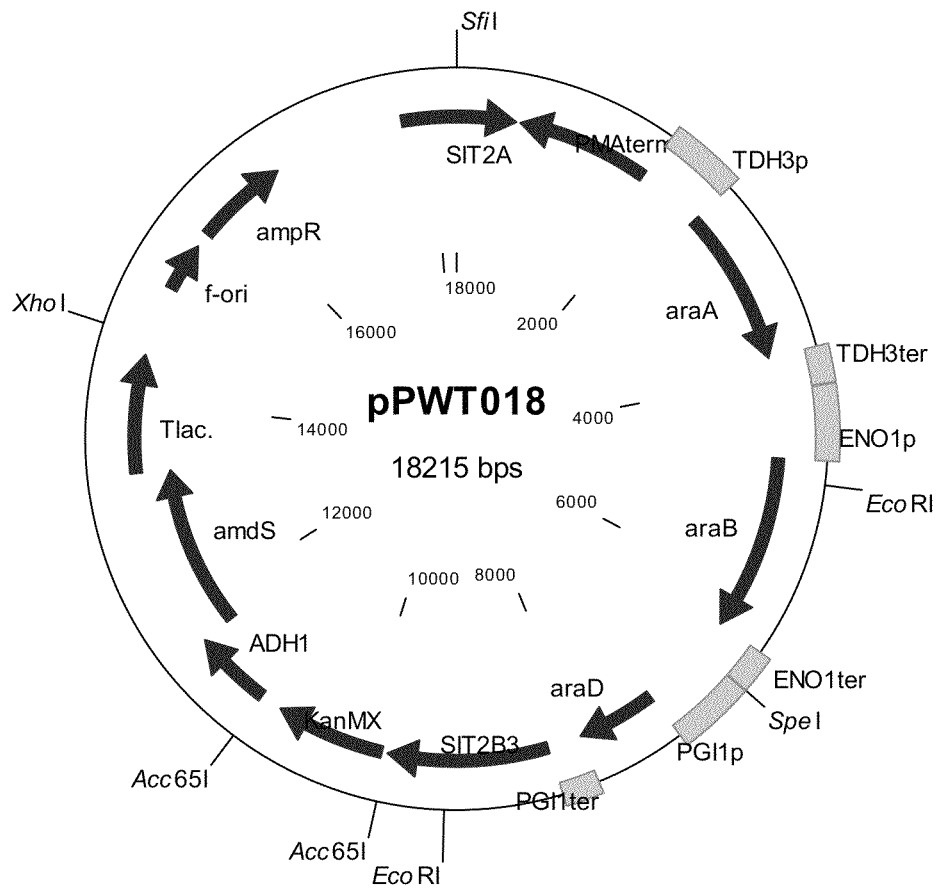
FIG. 2 sets out a physical map of plasmid pPWT018.

1.1 Construction of an Expression Vector Containing the Genes for Arabinose Pathway Plasmid pPWT018, as set out in FIG. 2, was constructed as follows: vector pPWT006 (FIG. 1, consisting of a S/T2-locus (Gottlin-Ninfa and Kaback (1986) Molecular and Cell Biology vol. 6, no. 6, 2185-2197) and the markers allowing for selection of transformants on the antibiotic G418 and the ability to grow on acetamide was digested with the restriction enzymes BsiWI and MluI. The kanMX-marker, conferring resistance to G418, was isolated from p427TEF (Dualsystems Biotech) and a fragment containing the amdS-marker has been described in the literature (Swinkels, B. W., Noordermeer, A. C. M. and Renniers, A. C. H. M (1995) The use of the amdS cDNA of *Aspergillus nidulans* as a dominant, bidirectional selectable marker for yeast transformation. Yeast Volume 11, Issue 1995A, page S579; and U.S. Pat. No. 6,051, 431). The genes encoding arabinose isomerase (araA), L-ribulokinase (araB) and L-ribulose-5-phosphate-4-epimerase (araD) from *Lactobacillus plantarum*, as disclosed in patent application WO2008/041840, were synthesized by BaseClear (Leiden, the Netherlands). One large fragment was synthesized, harbouring the three arabinose-genes mentioned above, under control of (or operable linked to) strong promoters from *S. cerevisiae*, i.e. the TDH3-promoter controlling the expression of the araA-gene, the ENO1-promoter controlling the araB-gene and the PGI1-promoter controlling the araD-gene. This fragment was surrounded by the unique restriction enzymes Acc65I and MluI. Cloning of this fragment into pPWT006 digested with MluI and BsiWI, resulted in plasmid pPWT018 (FIG. 2). The sequence of plasmid pPWT018 is set out in SEQ ID NO: 1.

1.2 Yeast Transformation

CEN.PK113-7D (MATa URA3 HIS3 LEU2 TRP1 MAL2-8 SUC2) was transformed with plasmid pPWT018, which was previously linearized with SfiI (New England Biolabs), according to the instructions of the supplier. A synthetic SfiI-site was designed in the 5'-flank of the SIT2-gene (see FIG. 2). Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml. After two to four days, colonies appeared on the plates, whereas the negative control (i.e. no addition of DNA in the transformation experiment) resulted in blank YPD/G418-plates. The integration of plasmid pPWT018 is directed to the SIT2-locus. Transformants were characterized using PCR and Southern blotting techniques.

PCR reactions, which are indicative for the correct integration of one copy of plasmid pPWT018, were performed with the primers indicated by SEQ ID NO: 2 and SEQ ID NO: 3, and SEQ ID NO: 3 and SEQ ID NO: 4. With the primer pairs of SEQ ID NO: 2 and SEQ ID NO: 3, the correct integration at the S/T2-locus was checked. If plasmid pPWT018 was integrated in multiple copies (head-to-tail integration), the primer pair of SEQ ID NO: 3 and SEQ ID NO: 4 will give a PCR-product. If the latter PCR product is absent, this is indicative for one copy integration of pPWT018. A strain in which one copy of plasmid pPWT018 was integrated in the S/T2-locus was designated BIE104R2.

1.3 Marker Rescue

In order to be able to transform the yeast strain with other constructs using the same selection markers, it is necessary to remove the selectable markers. The design of plasmid pPWT018 was such, that upon integration of pPWT018 in the chromosome, homologous sequences are in close proximity of each other. This design allows the selectable markers to be lost by spontaneous intramolecular recombination of these homologous regions.

Upon vegetative growth, intramolecular recombination will take place, although at low frequency. The frequency of this recombination depends on the length of the homology and the locus in the genome (unpublished results). Upon sequential transfer of a subfraction of the culture to fresh medium, intramolecular recombinants will accumulate in time.

To this end, strain BIE104R2 was cultured in YPD-medium (per liter: 10 grams of yeast extract, 20 grams per liter peptone, 20 grams per liter dextrose), starting from a single colony isolate. 25 μl of an overnight culture was used to inoculate fresh YPD medium. After at least five of such serial transfers, the optical density of the culture was determined and cells were diluted to a concentration of approximately 5000 per ml. 100 μl of the cell suspension was plated on Yeast Carbon Base medium (Difco) containing 30 mM KPi (pH 6.8), 0.1% (NH4)2SO4, 40 mM fluoro-acetamide (Amersham) and 1.8% agar (Difco). Cells identical to cells of strain BIE104R2, i.e. without intracellular recombination, still contain the amdS-gene. To those cells, fluoro-acetamide is toxic. These cells will not be able to grow and will not form colonies on a medium containing fluoro-acetamide. However, if intramolecular recombination has occurred, BIE104R2-variants that have lost the selectable markers will be able to grow on the fluoro-acetamide medium, since they are unable to convert fluoro-acetamide into growth inhibiting compounds. Those cells will form colonies on this agar medium.

The thus obtained fluoro-acetamide resistant colonies were subjected to PCR analysis using primers of SEQ ID NO:2 and SEQ ID NO: 3, and SEQ ID NO: 4 and SEQ ID NO: 5. Primers of SEQ ID NO: 2 and SEQ ID NO: 3 will give a band if recombination of the selectable markers has taken place as intended. As a result, the cassette with the genes araA, araB and araD under control of the strong yeast promoters have been integrated in the SIT2-locus of the genome of the host strain. In that case, a PCR reaction using primers of SEQ ID NO: 4 and SEQ ID NO: 5 should not result in a PCR product, since primer 4 primes in a region that should be lost due to the recombination. If a band is obtained with the latter primers, this is indicative for the presence of the complete plasmid pPWT018 in the genome, so no recombination has taken place.

If primers of SEQ ID NO: 2 and SEQ ID NO: 3 do not result in a PCR product, recombination has taken place, but in such a way that the complete plasmid pPWT018 has recombined out of the genome. Not only were the selectable markers lost, but also the arabinose-genes. In fact, wild-type yeast has been retrieved.

Figure 3:
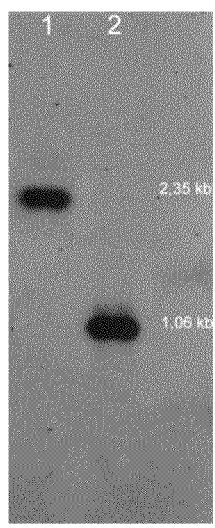
FIG. 3 sets out a Southern blot autoradiogram. Chromosomal DNA of wild-type strain CEN.PK113-7D (lane 1) and BIE104A2 (lane 2) was digested with both EcoRI and HindIII. The blot was hybridized with a specific SIT2-probe.

Isolates that showed PCR results in accordance with one copy integration of pPWT018 were subjected to Southern blot analysis. The chromosomal DNA of strains CEN.PK113-7D and the correct recombinants were digested with EcoRI and HindIII (double digestion). A S/T2-probe was prepared with primers of SEQ ID NO: 6 and SEQ ID NO: 7, using chromosomal DNA of strain CEN.PK113-7D as a template. The result of the hybridisation experiment is shown in FIG. 3.

In the wild-type strain, a band of 2.35 kb is observed, which is in accordance with the expected size of the wild-type gene. Upon integration and partial loss by recombination of the plasmid pPWT018, a band of 1.06 kb was expected. Indeed, this band is observed, as shown in FIG. 3 (lane 2).

One of the strains that showed the correct pattern of bands on the Southern blot (as can be deduced from FIG. 3) is the strain designated as BIE104A2.

1.4 Introduction of Four Constitutively Expressed Genes of the Non-Oxidative Pentose Phosphate Pathway

Figure 4:
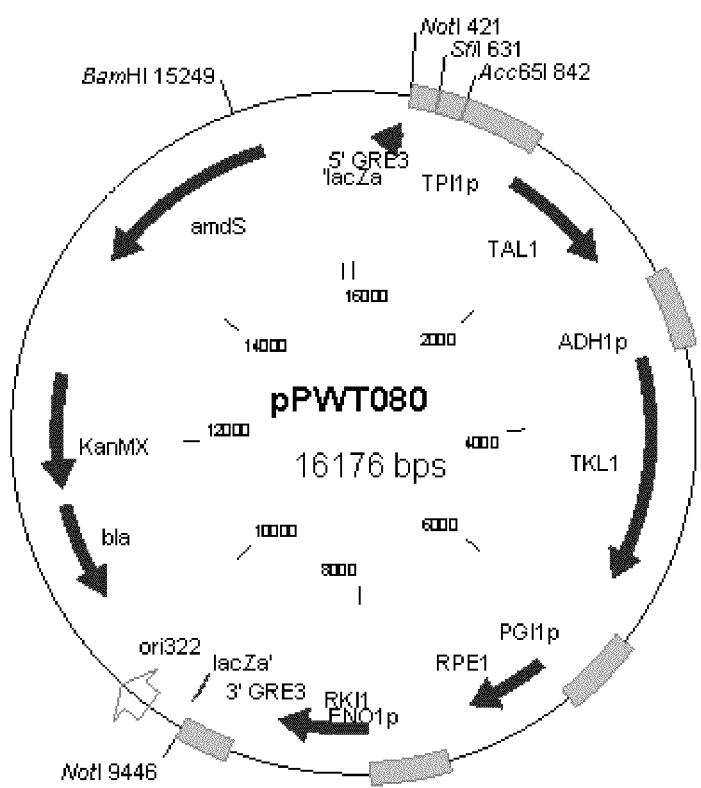
FIG. 4 sets out a physical map of plasmid pPWT080, the sequence of which is given in SEQ ID NO: 8

*Saccharomyces cerevisiae* BIE104A2, expressing the genes araA, araB and araD constitutively, was transformed with plasmid pPWT080 (FIG. 4). The sequence of plasmid pPWT080 is set out in SEQ ID NO: 8. The procedure for transformation and selection, after selecting a one copy integration transformant, are the same as described above in sections 1.1, 1.2 and 1.3. In short, BIE104A2 was transformed with SfiI-digested pPWT080. Transformation mixtures were plated on YPD-agar (per liter: 10 grams of yeast extract, 20 grams per liter peptone, 20 grams per liter dextrose, 20 grams of agar) containing 100 µg G418 (Sigma Aldrich) per ml.

After two to four days, colonies appeared on the plates, whereas the negative control (i.e. no addition of DNA in the transformation experiment) resulted in blank YPD/G418-plates.

The integration of plasmid pPWT080 is directed to the GRE3-locus. Transformants were characterized using PCR and Southern blotting techniques. The correct integration of the plasmid pPWT080 at the GRE3-locus was checked by PCR using primer pairs SEQ ID NO: 9 and SEQ ID NO: 10, and the primer pair SEQ ID NO: 9 and SEQ ID NO: 11 was used to detect single or multicopy integration of the plasmid pPWT080. For Southern analysis, a probe was prepared by PCR using SEQ ID NO: 12 and SEQ ID NO: 13, amplifying a part of the RKI1-gene of *S. cerevisiae*. Next to the native RKI1-gene, an extra signal was obtained resulting from the integration of the plasmid pPWT080 (data not shown)

A transformant showing correct integration of one copy of plasmid pPWT080, in accordance with the expected hybridisation pattern, was designated BIE104A2F1. In order to remove the selection markers introduced by the integration of plasmid pPWT080, strain BIE104A2F1 was cultured in YPD-medium, starting from a colony isolate. 25 µl of an overnight culture was used to inoculate fresh YPD-medium. After five serial transfers, the optical density of the culture was determined and cells were diluted to a concentration of approximately 5000 per ml. 100 µl of the cell suspension was plated on Yeast Carbon Base medium (Difco) containing 30 mM KPi (pH 6.8), 0.1% (NH4)2SO4, 40 mM fluoro-acetamide (Amersham) and 1.8% agar (Difco). Fluoro-acetamide resistant colonies were subjected to PCR analysis using the primers of SEQ ID NO: 9 and SEQ ID NO: 10. In case of correct PCR-profiles, Southern blot analysis was performed in order to verify the correct integration, again using the probe of the RKI1-gene. One of the strains that showed the correct pattern of bands on the Southern blot is the strain designated as BIE104A2P1.

Example 2

Adaptive Evolution in Shake Flask Leading to BIE104A2P1c and BIE201

2.1 Adaptive Evolution (Aerobically)

Figure 5:
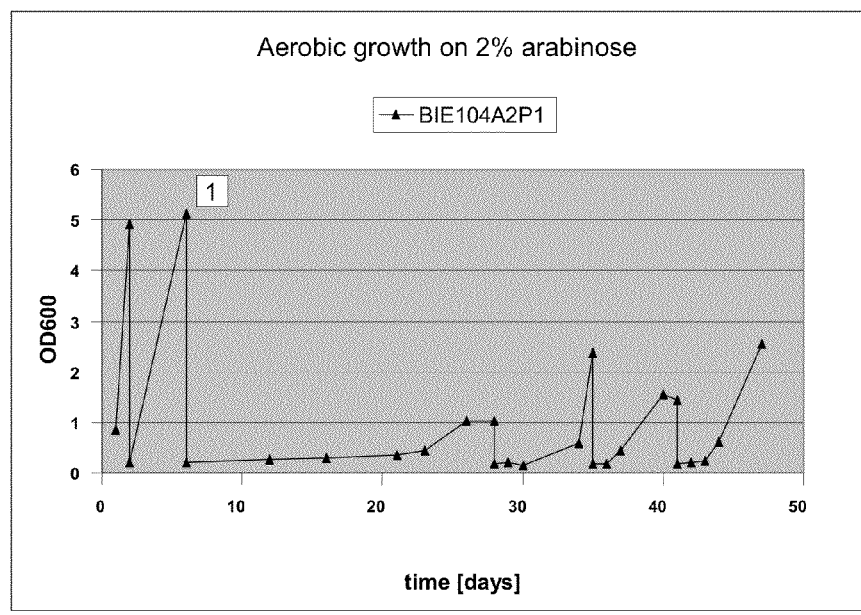
FIG. 5 sets out a growth curves under aerobic conditions of BIE104P1A2 on different media. Strain BIE104A2P1 was pregrown on YNB 2% galactose. Growth curve was started on 2% galactose and 1% arabinose, followed by event indicated in the graph by number (1) transfer to YNB with 2% arabinose as sole carbon source. After reaching an OD 600 more than 1, the culture was transferred to fresh medium with a starting OD 600 of 0.2. Upon three transfers on pure arabinose medium the resulting strain was designated BIE104P1A2c.

A single colony isolate of strain BIE104A2P1 was used to inoculate YNB-medium (Difco) supplemented with 2% galactose. The preculture was incubated for approximately 24 hours at 30° C. and 280 rpm in an orbital shaker. Cells were harvested and inoculated in YNB medium containing 1% galactose and 1% arabinose at a starting $OD^{600}$ of 0.2 (FIG. 5). Cells were grown at 30° C. and 280 rpm in an orbital shaker. The optical density at 600 nm was monitored regularly.

When the optical density reached a value of 5, an aliquot of the culture was transferred to fresh YNB medium containing the same medium. The amount of cells added was such that the starting $OD^{600}$ of the culture was 0.2. After reaching an $OD^{600}$ of 5 again, an aliquot of the culture was transferred to YNB medium containing 2% arabinose as sole carbon source (event indicated by (1) in FIG. 5).

Upon transfer to YNB with 2% arabinose as sole carbon source growth could be observed after approximately two weeks. When the optical density at 600 nm reached a value at least of 1, cells were transferred to a shake flask with fresh YNB-medium supplemented with 2% arabinose at a starting $OD^{600}$ of 0.2 (FIG. 5, day 28).

Sequential transfer was repeated three times, as is set out it in FIG. 5. The resulting strain which was able to grow fast on arabinose was designated BIE104A2P1c.

2.2 Adaptive Evolution (Anaerobically)

Figure 6:
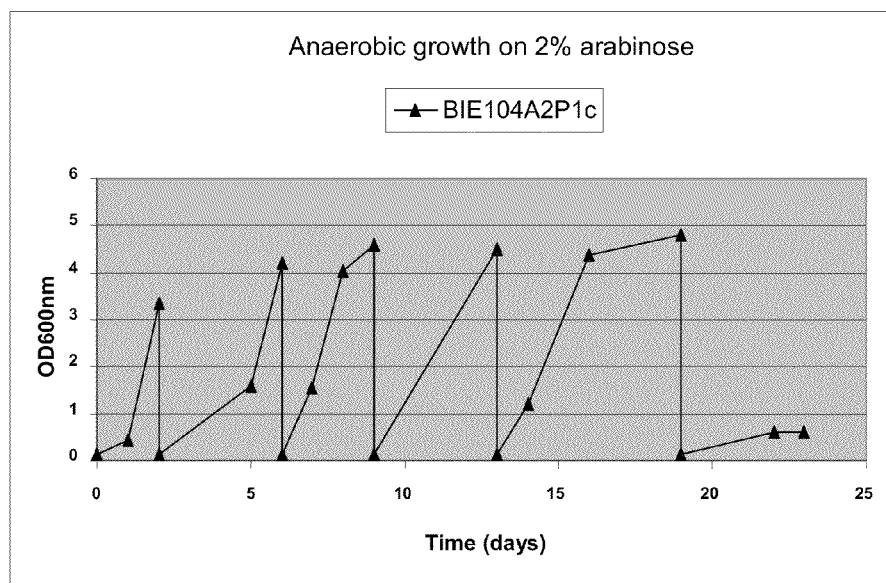
FIG. 6 sets out a growth curves under anaerobic conditions of BIE104P1A2c on YNB 2% arabinose as sole carbon source. After reaching an OD 600 higher than 1, the culture was transferred to fresh medium with a starting OD 600 of 0.2. After several transfers the resulting strain was named BIE104P1A2d (=BIE201).

After adaptation on growth on arabinose under aerobic conditions, a single colony from strain BIE104A2P1c was inoculated in YNB medium supplemented with 2% glucose. The preculture was incubated for approximately 24 hours at 30° C. and 280 rpm in an orbital shaker. Cells were harvested and inoculated in YNB medium containing 2% arabinose, with a initial optical density $OD^{600}$ of 0.2. The flasks were closed with waterlocks, ensuring anaerobic growth conditions after the oxygen was exhausted from the medium and head space. After reaching an $OD^{600}$ minimum of 3, an aliquot of the culture was transferred to fresh YNB medium containing 2% arabinose (FIG. 6), each time at an initial $OD^{600}$ value of 0.2. After several transfers the resulting strain was designated BIE104A2P1d (=BIE201).

Example 3

Construction of strain BIE201X9

3.1 Transformation of Strain BIE201

Figure 7:
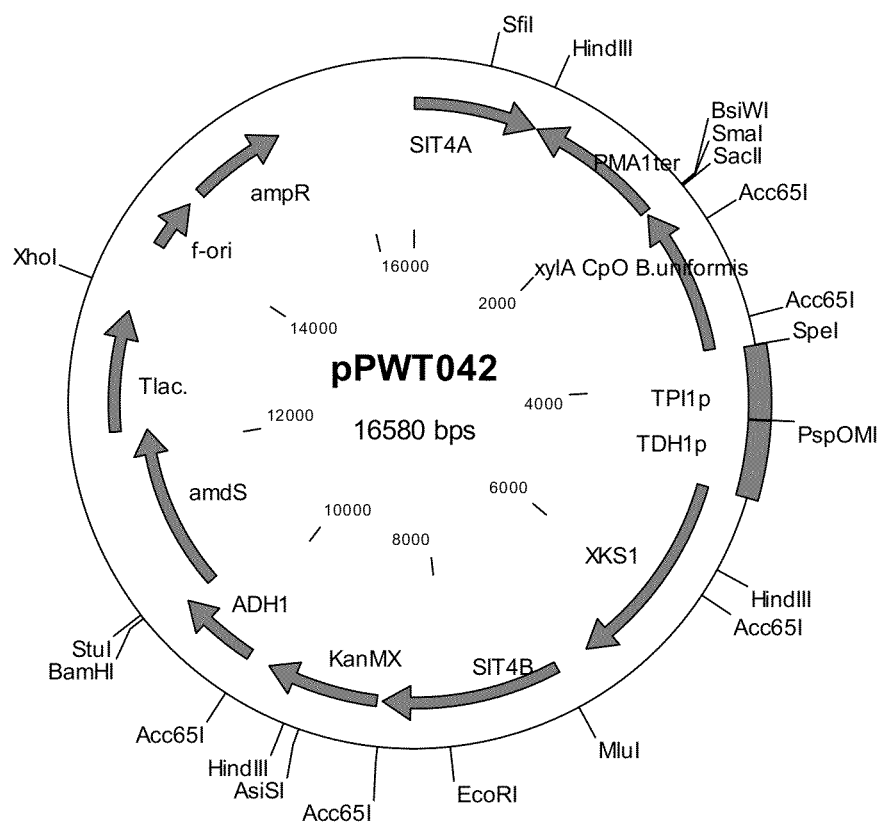
FIG. 7 sets out a physical map of the plasmid pPWT042, the sequence of which is given in SEQ ID NO:14.

Strain BIE201 was transformed with plasmid pPWT042. The physical map of plasmid pPWT042 is set out in FIG. 7. Plasmid pPWT042 (SEQ ID NO: 14) contains a 4630 by insert containing a codon pair optimized xylA-gene from *Bacteroides uniformis* under control of the TPI1-promoter and the XKS1-gene from *S. cerevisiae* under control of the TDH1-promoter. Prior to the transformation of BIE201, pPWT042 was linearized using the restriction enzyme SfiI, according to the instructions provided by the supplier. Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml.

After two to four days, colonies appeared on the plates, whereas the negative control (i.e. no addition of DNA in the transformation experiment) resulted in blank YPD/G418-plates.

Upon digestion of plasmid pPWT042 with SfiI, its integration is directed to the SIT4-locus (Gottlin-Ninfa and Kaback (1986) Molecular and Cellular Biology Vol. 6, No. 6, 2185-2197) in the genome. Transformants were characterized using PCR and Southernblotting techniques. PCR reactions, using PHUSION® DNA polymerase (Finnzymes), which are indicative for the correct integration of one copy of plasmid pPWT042, were performed with the primers indicated by SEQ ID NO's 15 and 16 (correct integration of pPWT042 at the SIT4-locus), and SEQ ID NO's 16 and 17 (band only appears in case of multicopy integration). A strain with one copy of plasmid pPWT042 integrated into the genome was designated BIE201Y9.

3.2 Marker Rescue

In order to remove the selection markers introduced by the integration of plasmid pPWT042, the following procedure was performed. The design of plasmid pPWT042 is such, that upon integration of pPWT042 in the chromosome, homologous sequences are in close proximity of each other. This design allows the selectable markers to be lost by spontaneous intramolecular recombination of these homologous regions. Upon vegetative growth, intramolecular recombination will take place, although at low frequency. The frequency of this recombination depends on the length of the homology and the locus in the genome (unpublished results). Upon sequential transfer of a subfraction of the culture to fresh medium, intramolecular recombinants will accumulate in time.

To this end, strain BIE201Y9 was cultured in YPD-2% glucose, starting from a single colony isolate. 25 μl of an overnight culture was used to inoculate fresh YPD-2% glucose medium. After five serial transfers, the optical density of the culture was determined and cells were diluted to a concentration of approximately 5000 per ml. 100 μl of the cell suspension was plated on Yeast Carbon Base medium (Difco) containing 30 mM KPi (pH 6.8), 0.1% (NH4)2S4, 40 mM fluoro-acetamide (Amersham) and 1.8% agar (Difco). Cells identical to cells of strain BIE201Y9, i.e. without intracellular recombination, still contain the amdS-gene. To those cells, fluoro-acetamide is toxic. These cells will not be able to grow and will not form colonies on a medium containing fluoro-acetamide. However, if intramolecular recombination has occurred, BIE201Y9-variants that have lost the selectable markers will be able to grow on the fluoro-acetamide medium, since they are unable to convert fluoro-acetamide into growth inhibiting compounds. Those cells will form colonies on this agar medium.

The thus obtained fluoro-acetamide resistant colonies were subjected to PCR analysis using primers of SEQ ID NO: 15 and SEQ ID NO: 16, and SE ID NO: 17 and SEQ ID NO: 18. Primers of SEQ ID NO: 15 and SEQ ID NO: 16 will give a band if recombination of the selectable markers has taken place as intended. As a result, the genes xylA and XKS1 have been integrated into the SIT4-locus. In that case, a PCR reaction using primers of SEQ ID NO: 17 and SEQ ID NO: 18 should not result in a PCR product, since primer 17 primes in a region that should be out-recombined. If a band is obtained with these primers, this is indicative for the presence of the complete plasmid pPWT042 in the genome, so no recombination has taken place.

If primers of SEQ ID NO: 15 and SEQ ID NO: 16 do not result in a PCR product, recombination has taken place, but in such a way that the complete plasmid pPWT042 has recombined out of the genome. Not only were the selectable markers lost, but also the xylA- and XKS1-gene. In fact, wild-type yeast has been retrieved.

Isolates that exhibited the expected PCR results, were subjected to Southern blot analysis (vide supra). One of the strains that showed the correct pattern of bands on the Southern blot is the strain designated as BIE201X9.

Example 4

Construction and Selection of Strain BIE252

4.1 Amplification of the xylA-Cassette

In order to introduce extra copies of the xylA-gene into the genome, a PCR reaction was performed using PHUSION® DNA polymerase (Finnzymes) with plasmid pPWT042 as a template and the oligonucleotides with SEQ ID NO: 19 and SEQ ID NO: 20 as primers. With these primers, the xylA-cassette, comprising the TPI1-promotor, the codon-pair optimized xylA-gene and the PMA1-terminator, is being amplified. The primer design is such that the flanks of the PCR fragment are homologous to the consensus sequence of the delta-sequences of the yeast transposon Ty-1. These sequences can be obtained from NCBI ( ) and aligned using a software package allowing to do so, like e.g. Clone Manager 9 Professional Edition (Scientific & Educational Software, Cary, USA).

The xylA-cassette does not contain a selectable marker with which the integration into the genome can be selected for. In order to estimate transformation frequency, a second control transformation was done with the kanMX-marker. To this end, the kanMX-cassette from plasmid p427TEF (Dualsystems Biotech) was amplified in a PCR reaction using the primers corresponding to SEQ ID NO: 21 and SEQ ID NO: 22.

4.2 Transformation of BIE201X9

BIE201X9 was transformed according to the electroporation protocol (as described above) with the fragments comprising either 30 μg of the xylA-cassette (designated X18-Ty1) or 10 μg of the kanMX-cassette. The kanMX-transformation mixture was plated on YPD-agar (per liter: 10 grams of yeast extract, 20 grams per liter peptone, 20 grams per liter dextrose, 20 grams of agar) containing 100 μg G418 (Sigma Aldrich) per ml. After two to four days, colonies appeared on the plates, whereas the negative control (i.e. no addition of DNA in the transformation experiment) resulted in blank YPD/G418-plates. The transformation frequency appeared to be higher than 600 colonies per μg of kanMX-cassette.

The X18-Ty1 transformation mixture was used to inoculate a shake flask containing 100 ml of Verduyn medium, supplemented with 2% xylose. As a control, the negative control of the transformation (i.e. no addition of DNA in the transformation experiment) was used. The shake flasks were incubated at 30° C. and 280 rpm in an orbital shaker. Growth was followed by measuring the optical density at 600 nm on a regular basis.

Figure 8:
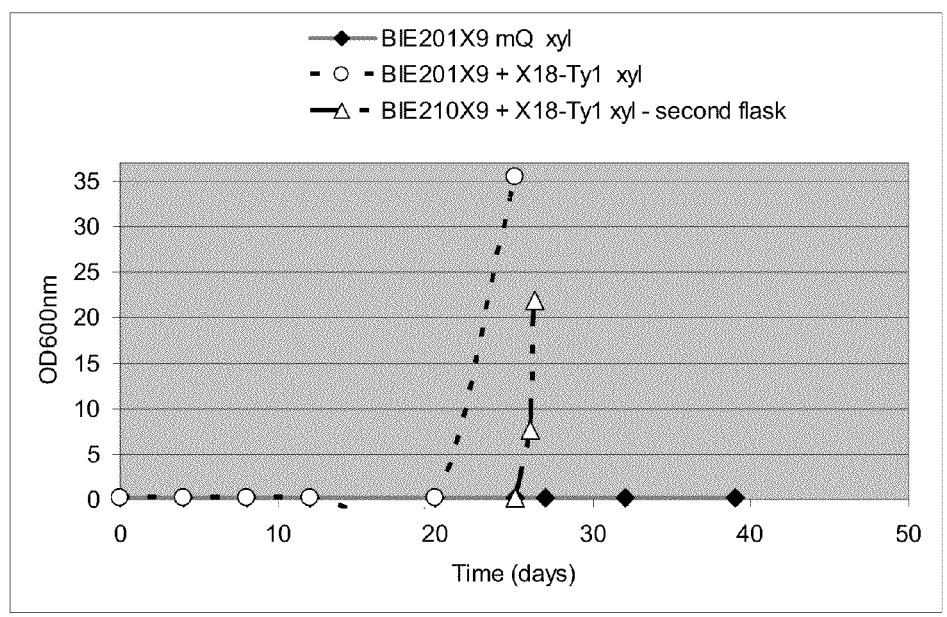
FIG. 8 sets out a growth curve under aerobic conditions of a transformation mixture. Strain BIE201X9 was transformed with fragment X18-Ty1 and the transformation mixture was used to inoculate Verduyn-medium supplemented with 2% xylose. After reaching an OD 600 of approximately 35, an aliquot of the culture was used to inoculate a second flask with fresh medium. From the second flask, colonies were isolated for further analysis.

The result of the growth curve is depicted in FIG. 8. As can be seen, between days 20 and 25, the optical density of the X18-Ty1 shake flask increased spectacularly, while the growth in the negative control was still absent. At day 25, a flask containing fresh Verduyn medium supplemented with 2% xylose was inoculated from the X18-Ty1 culture to a start optical density at 600 nm of 0.15. From FIG. 8 it is clear that upon re-inoculation the culture started to grow on xylose immediately and rapidly. Since it is likely that the culture consists of a mixture of subcultures, thus consisting of cells with differences in copy number of the X18-Ty1 cassette and in growth rate on xylose, cells were diluted in milliQ water and plated on YPD-agar plates in order to get single colony isolates. The single colony isolates were tested for their ability to utilize different carbon sources.

4.3 Selection of Strain BIE252

In order to select a strain which has gained improved growth on xylose as a sole carbon source without losing its ability to utilize the other important sugars (glucose, arabinose and galactose), ten single colony isolates of the adaptive evolution culture were restreaked on YPD-agar. Subsequently, a preculture was done on YPD-medium supplemented with 2% glucose. The ten cultures were incubated overnight at 30° C. and 280° C. Aliquots of each culture were used to inoculate fresh Verduyn medium supplemented with either 2% glucose, or 2% xylose, or 2% arabinose or 2% galactose, at an initial optical density of 0.15. As controls, strains BIE201, BIE201X9 and the mixed population (from which the ten single colony isolates were retrieved) were included in the experiment. Cells were grown at 30° C. and 280 rpm in an orbital shaker. Growth was assessed on basis of optical density measurements at 600 nm. The results of the optical density at 600 nm after 19 hours of incubation are presented in FIG. 9.

Figure 9:
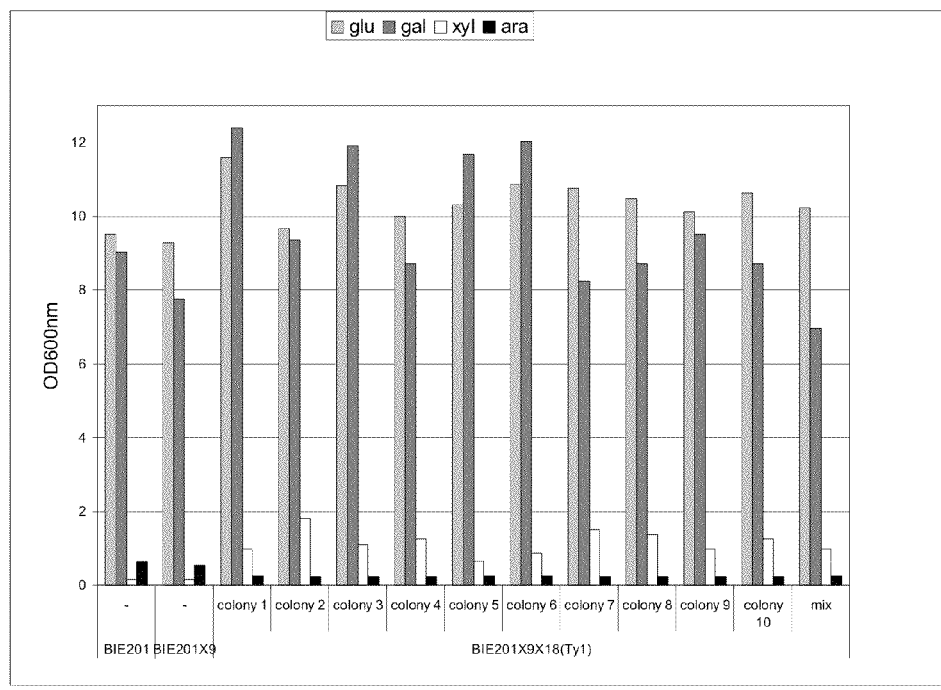
FIG. 9 sets out the growth of single colony isolates on Verduyn-medium supplemented with either 2% glucose, or 2% xylose, or 2% arabinose or 2% galactose.

The results of FIG. 9 show that both the mixed culture and the ten single colony isolates exhibit a higher final optical density at 600 nm on xylose. Although these strains grew on arabinose as sole carbon source, the final optical density at 600 nm was less as compared to the parent strains, BIE201 and BIE201×9, at 19 hours after inoculation. After prolonged growth, for several days, colony 3 was selected because it had reached the highest optical density as compared to the other single colony isolate cultures (data not shown). Growth on xylose was not different in all colonies tested.

Figure 10:
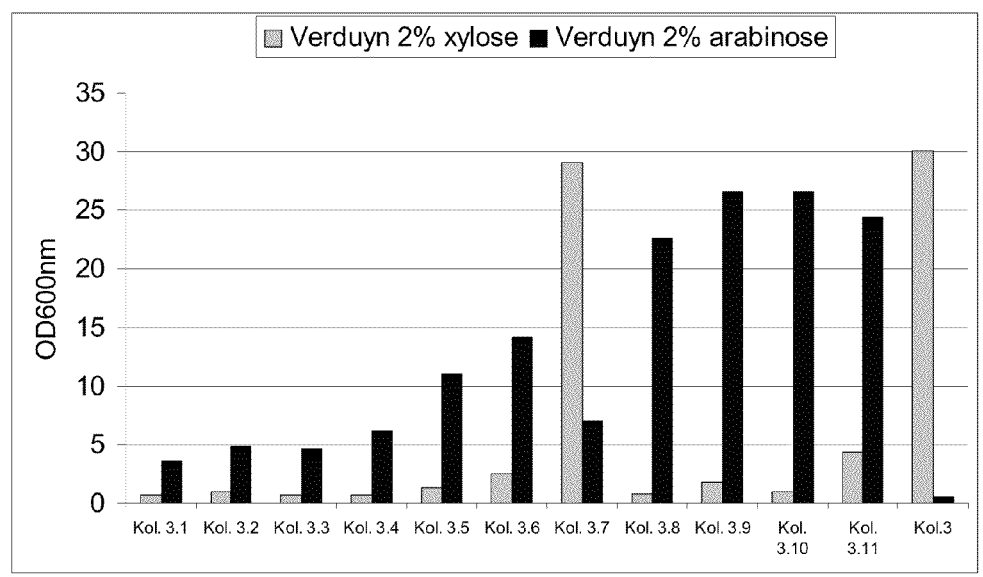
FIG. 10 sets out the growth of selected single colony isolates on Verduyn-medium supplemented with either 2% xylose or 2% arabinose.
Figure 11:
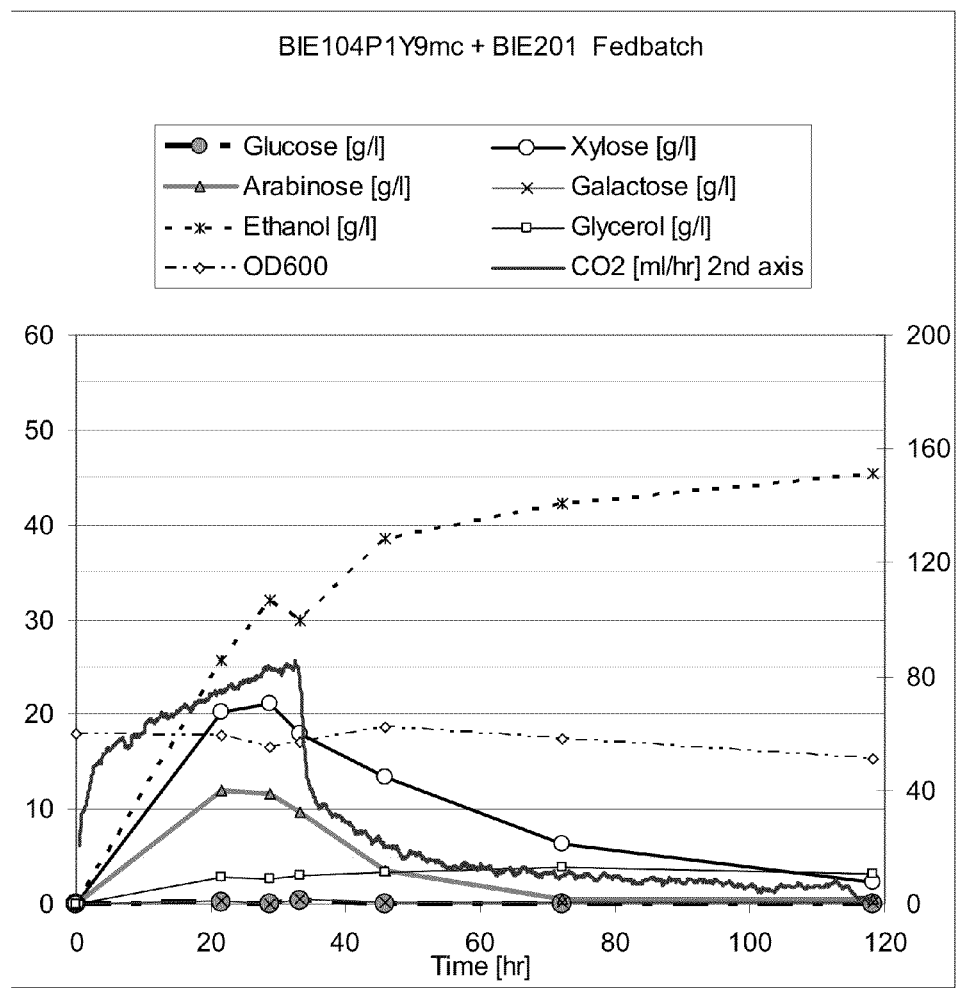
FIG. 11 sets out the sugar conversion and product formation of a mixed culture of strains BIE104P1Y9mc and BIE201 on synthetic medium, in a fed-batch experiment. $CO_2$ production was measured constantly. Growth was monitored by following optical density of the culture. Preculture was grown on 2% glucose.
Figure 12:
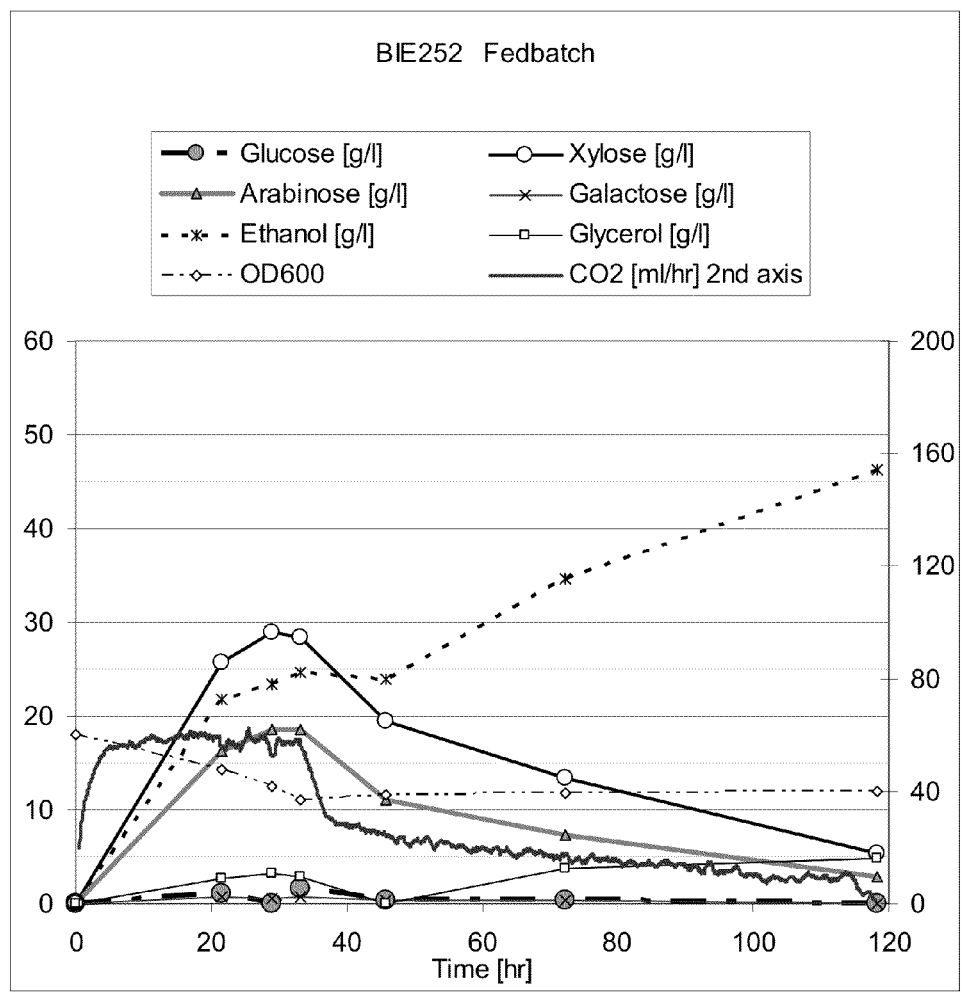
FIG. 12 sets out the sugar conversion and product formation of strain BIE252 on synthetic medium, in a fed-batch experiment. $CO_2$ production was measured constantly. Growth was monitored by following optical density of the culture. Preculture was grown on 2% glucose.

The colony 3 culture was diluted and plated on YPD-agar. Eleven single colony isolates were tested for their ability to grow on Verduyn medium, supplemented with either 2% arabinose or 2% xylose. To this end, a preculture was done on Verduyn 2% glucose. Cells were grown overnight at 30° C. and 280 rpm in an orbital shaker. An aliquot was transferred to Verduyn medium, supplemented with either 2% arabinose or 2% xylose at an initial optical density of 0.15. The culture of colony 3 was included as a control in this test. Cells were grown overnight at 30° C. and 280 rpm in a orbital shaker. Growth was assessed on basis of optical density measurements at 600 nm. The results of the optical density at 600 nm after 4 days of incubation are presented in FIG. 10.

Figure 23:
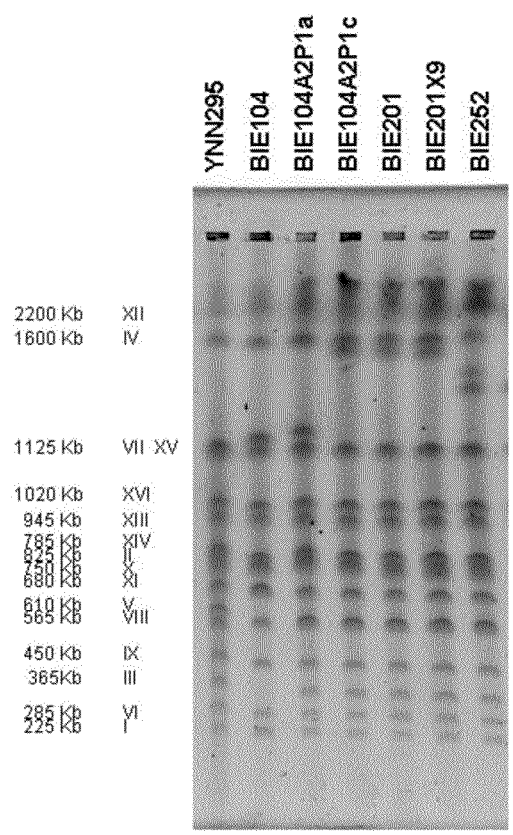
FIG. 23 sets out a CHEF gel, stained with ethidium bromide. Chromosomes were separated on their size using the CHEF technique. Strains analyzed are BIE104 (untransformed yeast cell), BIE104A2P1a (primary transformant unable to consume arabinose, synonym of BIE104A2P1), BIE104A2P1c, a strain derived from BIE104A2P1 by adaptive evolution, which is able to grow on arabinose, strain BIE201, derived from BIE104A2P1c by adaptive evolution, which can grow on arabinose under anaerobic conditions and strain BIE252, that is a mixed sugar strain. Shifts in chromosomes are observed (see text). Strain YNN295 is a marker strain (Bio-Rad), used as a reference for the size of the chromosomes.

The results show that colony 3.7 has reached an optical density similar to the culture of the control, colony 3, on xylose. In addition, its ability to grow on arabinose as sole carbon source has largely improved as compared to the culture of colony 3. The other single colony isolates also show an improved growth on arabinose, apparently at the expense of the ability to grow on xylose. The culture of single colony isolate 3.7 was designated strain BIE252. SNP's and amplification in BIE252 were determined following the same procedures as described in the co-pending PCT application, filed on 19 Apr. 2011, claiming priority from EP10160647.3. These test showed that BIE252 has the SNP's: G1363T in the SSY1 gene, A512T in YJR154w gene, A1186G in CEP3 gene, and A436C in GAL80 gene. These are the same as in BIE201. Also amplification in chromosome VII that exists in BIE201 is present in BIE252. This is shown in FIG. 23.

Example 5

Performance Test in BAM

In order to test the performance of the selected strain BIE252, the strain was inoculated in Verduyn medium, supplemented with 2% glucose. As controls, strains BIE201 and BIE104P1Y9mc were included. The first is a strain capable of fermenting glucose, galactose and arabinose (vide supra), and the latter is a strain capable of fermenting glucose, galactose and xylose.

After overnight incubation at 30° C. and 280 rpm in a rotary shaker, cells were harvested by centrifugation and cultivations for $CO_2$ production were performed at 33° C. in 100 ml Verduyn medium supplemented 5% glucose, 5% xylose, 3.5% arabinose and 1% galactose) in the BAM (Biological Activity Monitor). In one experiment, the batch experiment, the cells were added to the 100 ml of Verduyn medium supplemented with the sugars. In a second experiment, the fed-batch experiment, the 100 ml of Verduyn medium supplemented with the sugars was added to the cells at a rate of 3 ml per minute. The $CO_2$ production was constantly monitored at intervals, and samples were taken for analysis (optical density at 600 nm, ethanol, residual sugars). The strains BIE201 and BIE104P1Y9mc were mixed in a 1:1 ratio, based on the optical density, just prior to the BAM experiment.

The results of the BAM experiment are shown in FIGS. 11, 12, 13, 14, 15 and 16.

The performance of the mixed strains (BIE201 and BIE104P1Y9mc) in fed-batch mode (FIG. 11) shows that despite xylose and arabinose accumulate to a certain extent in time, already before the end of the feed (at approximately 33 hr) the consumption rate is faster than the feed rate. After 72 hrs, all arabinose has been converted, while xylose is not fully consumed. Glucose and galactose are always at or near the detection level, indicating that these sugars are preferred above the pentoses arabinose and xylose.

Figure 13:
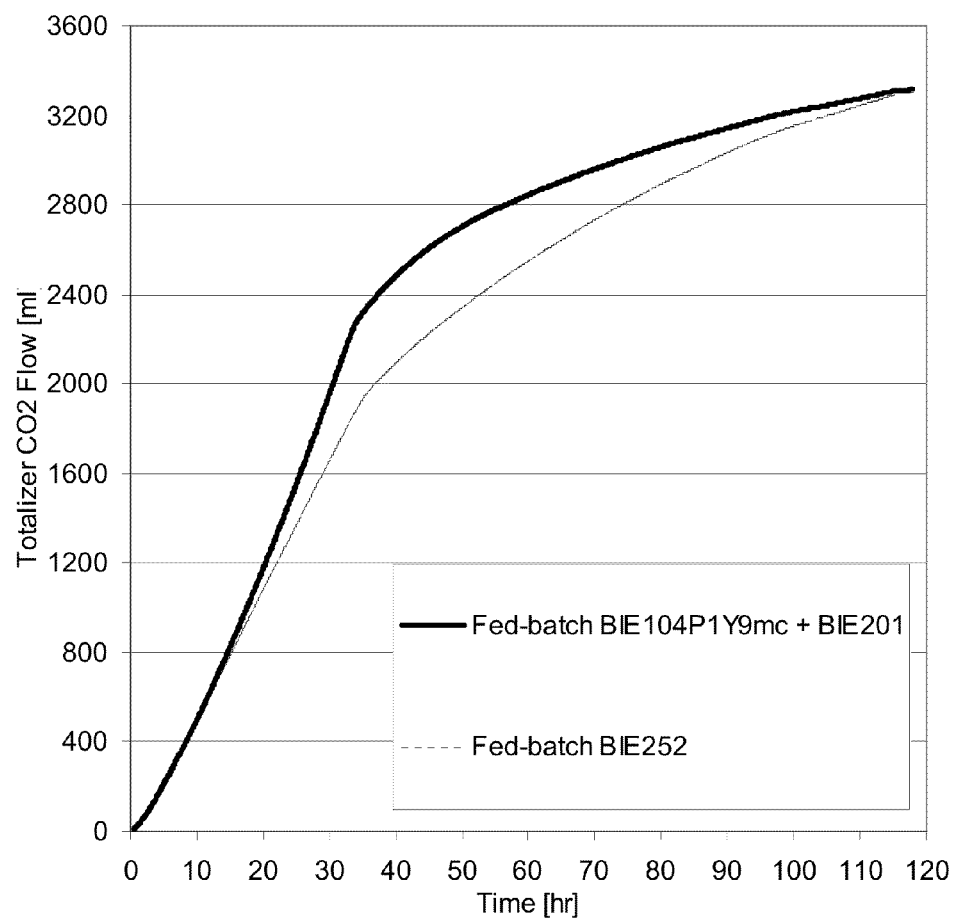
FIG. 13 sets out the total $CO_2$ that was produced in the fed-batch experiments.

The performance of strain BIE252, as tested in fed-batch mode in the BAM (see FIG. 12), shows essentially the same characteristics as the mixed strains culture. However, xylose and arabinose accumulate to higher concentrations, but the subsequent conversion into ethanol takes place at a higher rate, which results in the same ethanol titer and identical cumulative $CO_2$ production after 120 hrs (FIG. 13).

Figure 14:
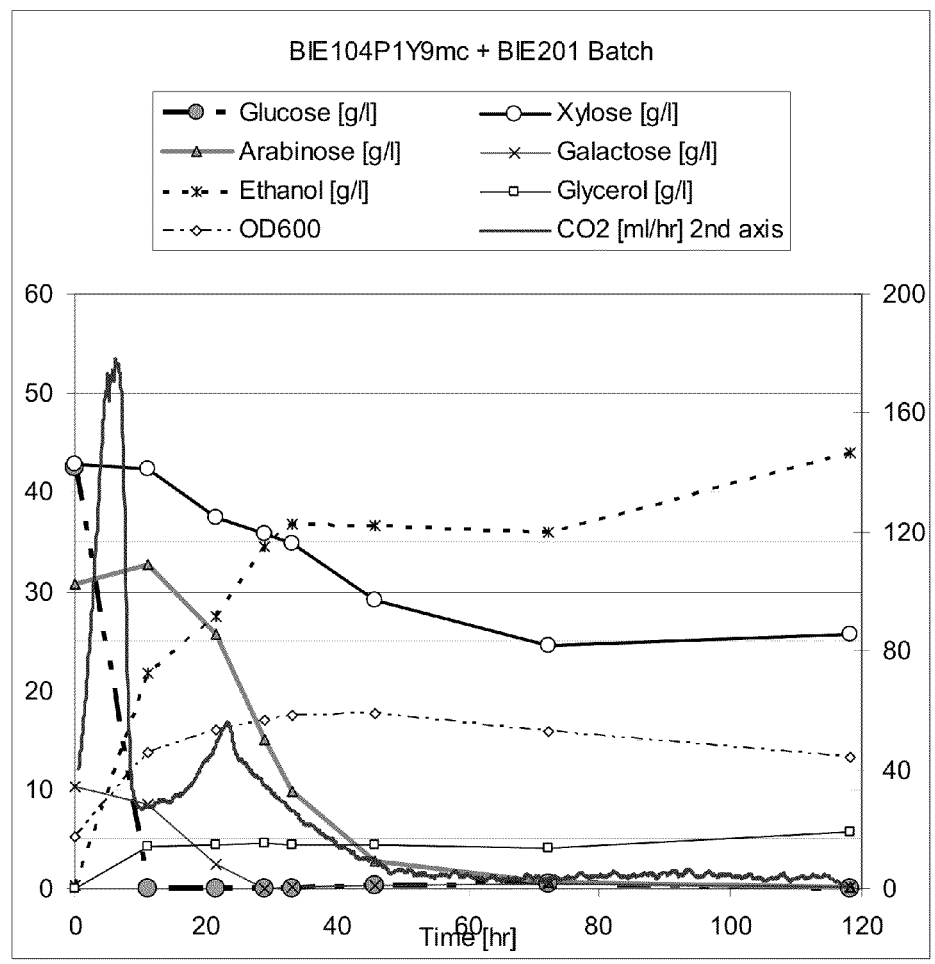
FIG. 14 sets out the sugar conversion and product formation of a mixed culture of strains BIE104P1Y9mc and BIE201 on synthetic medium, in a batch experiment. $CO_2$ production was measured constantly. Growth was monitored by following optical density of the culture. Preculture was grown on 2% glucose.
Figure 15:
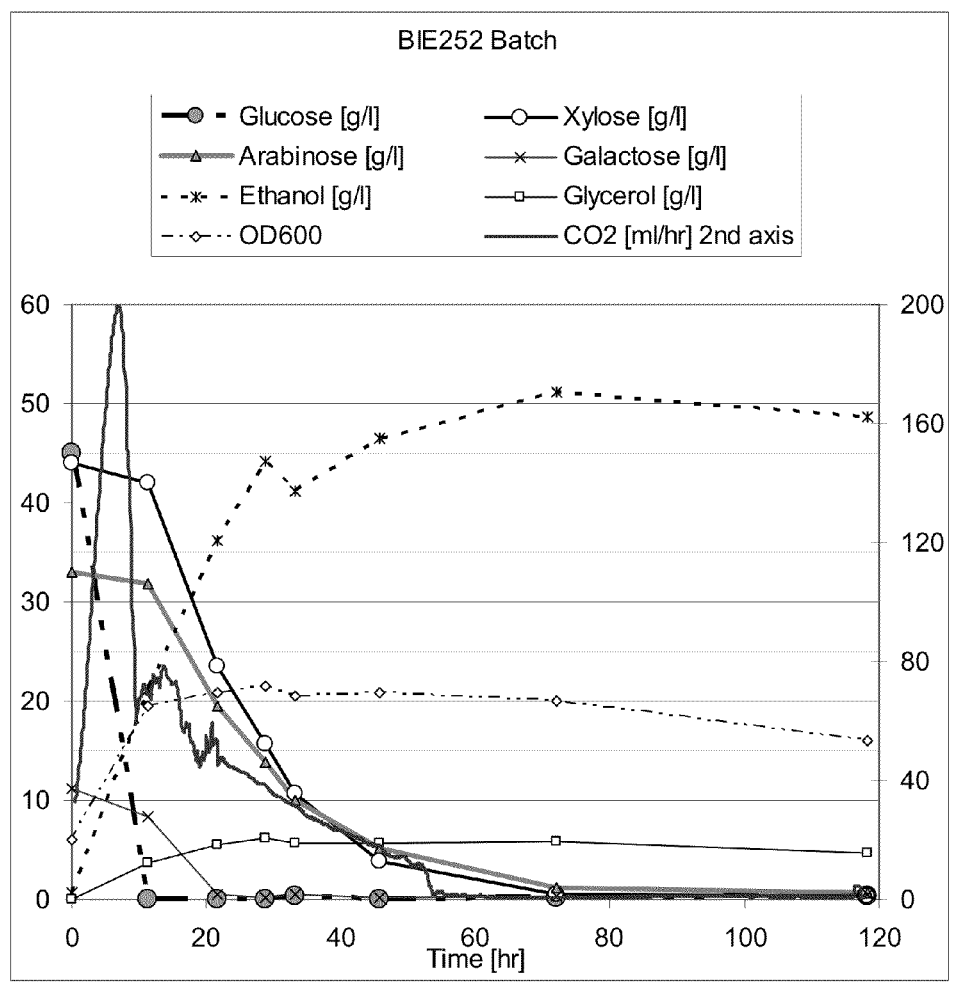
FIG. 15 sets out the sugar conversion and product formation of a mixed culture of strain BIE252 on synthetic medium, in a batch experiment. $CO_2$ production was measured constantly. Growth was monitored by following optical density of the culture. Preculture was grown on 2% glucose.
Figure 16:
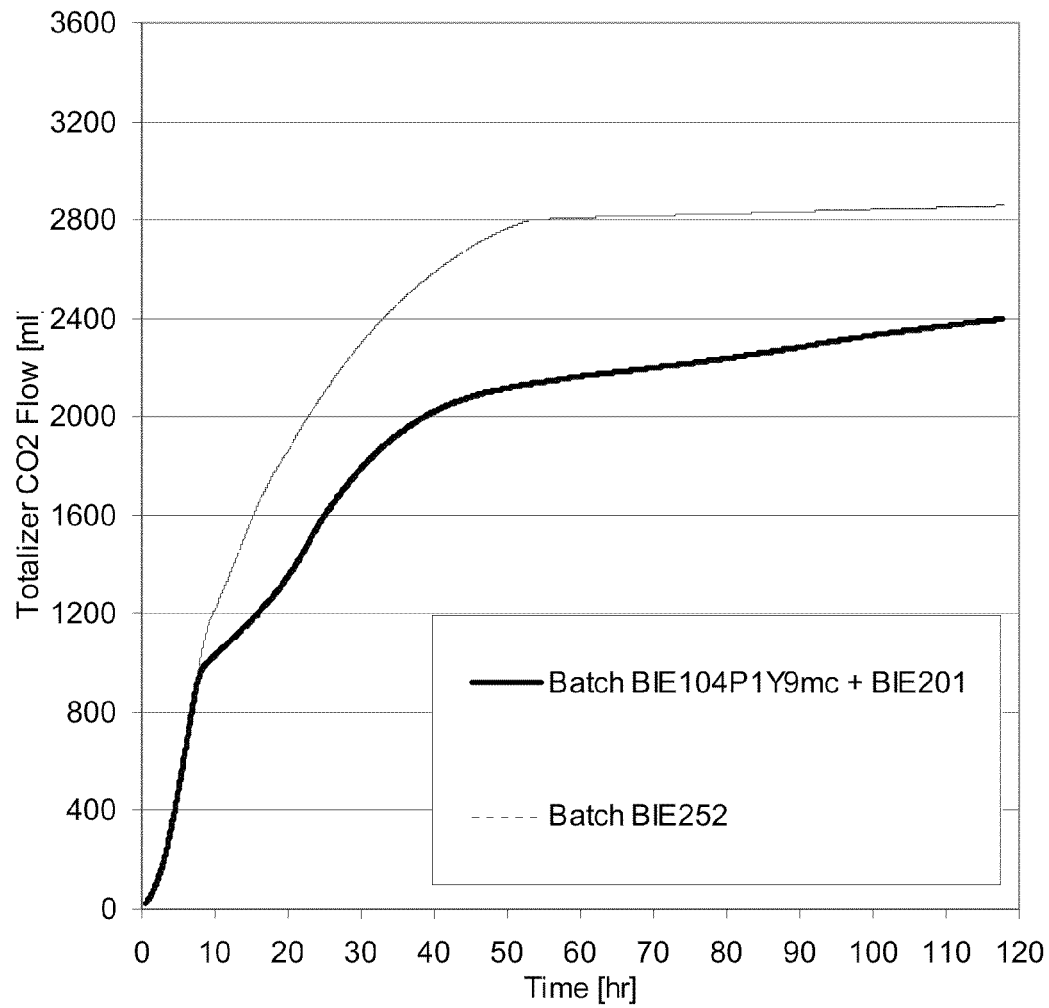
FIG. 16 sets out the total $CO_2$ that was produced in the batch experiments.

In batch mode, the performance of the mixed strains (BIE201 and BIE104P1Y9mc) in batch mode shows that glucose is consumed readily after the start of the fermentation experiment (FIG. 14). Subsequently, galactose, arabinose and xylose are being co-fermented. After approximately 30 hrs, galactose was consumed. After approximately 72 hours, arabinose was also fully consumed. Both contributed significantly to the formation of $CO_2$ and ethanol. Xylose consumption, and thus ethanol and $CO_2$ production slowed down significantly after the exhaustion of arabinose. Strain BIE252 performed better in that respect (FIG. 15). Immediately after glucose exhaustion within 10 hours, galactose, arabinose and xylose were co-fermented rapidly and efficiently. Even after galactose exhaustion, both pentoses arabinose and xylose were co-fermented completely, both contributing to $CO_2$-production and ethanol formation. The fermentation of all sugars was complete after approximately 72 hours, in case of strain BIE252. This resulted in a higher cumulative CO2- production of strain BIE252 compared to the mixed strains culture (BIE201 and BIE104P1Y9mc) as is set out in FIG. 16.

Example 6

Performance Test in Real Hydrolysates

The performance test in real hydrolysates was performed using strain BIE252 which was cultured overnight in shake flasks containing YEP medium supplemented with 2% glucose. The cells were harvested by centrifugation at resuspended at a concentration of 50 grams dry matter per liter.

The feed stocks that were tested consisted of batches of corn fiber, corn stover and wheat straw. The hydrolysis and fermentation were performed as described in the materials and methods section.

Figure 17:
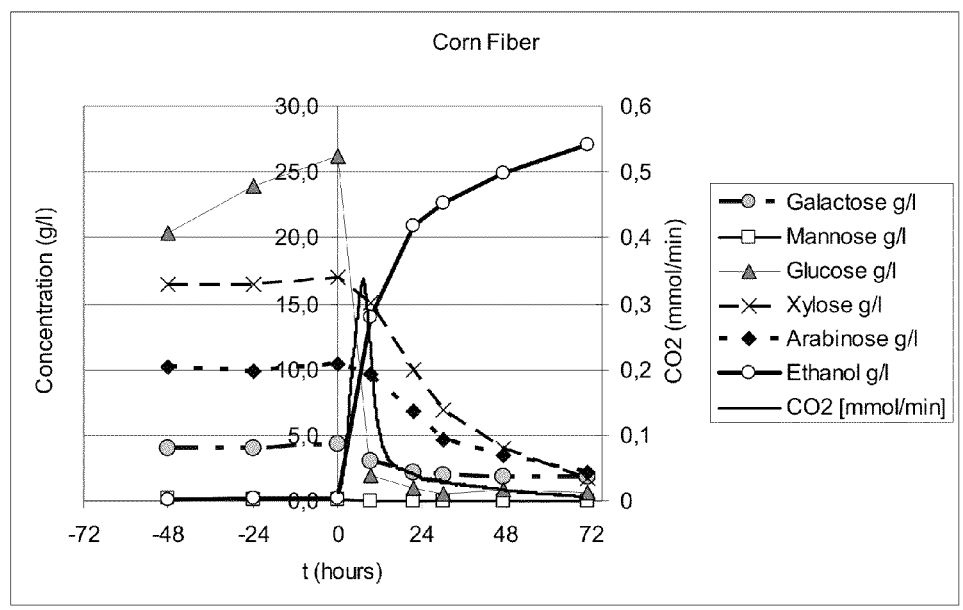
FIG. 17 sets out the performance of strain BIE252 in hydrolyzed corn fiber at 13.8% d.m. CO2 production rate, ethanol production and sugar conversion are shown.
Figure 18:
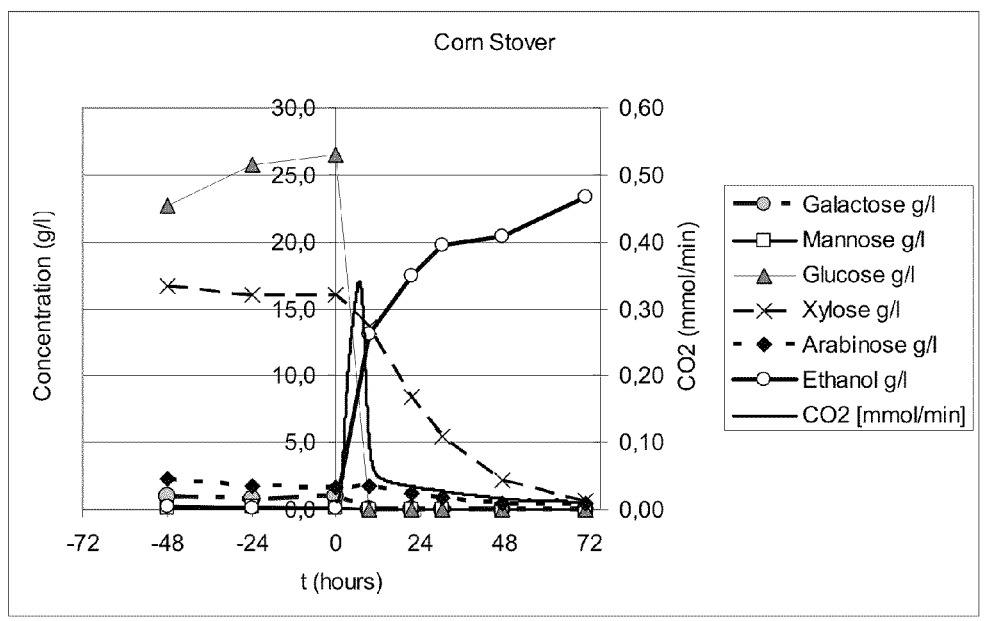
FIG. 18 sets out the performance of strain BIE252 in hydrolyzed corn stover at 10% d.m. CO2 production rate, ethanol production and sugar conversion are shown.
Figure 19:
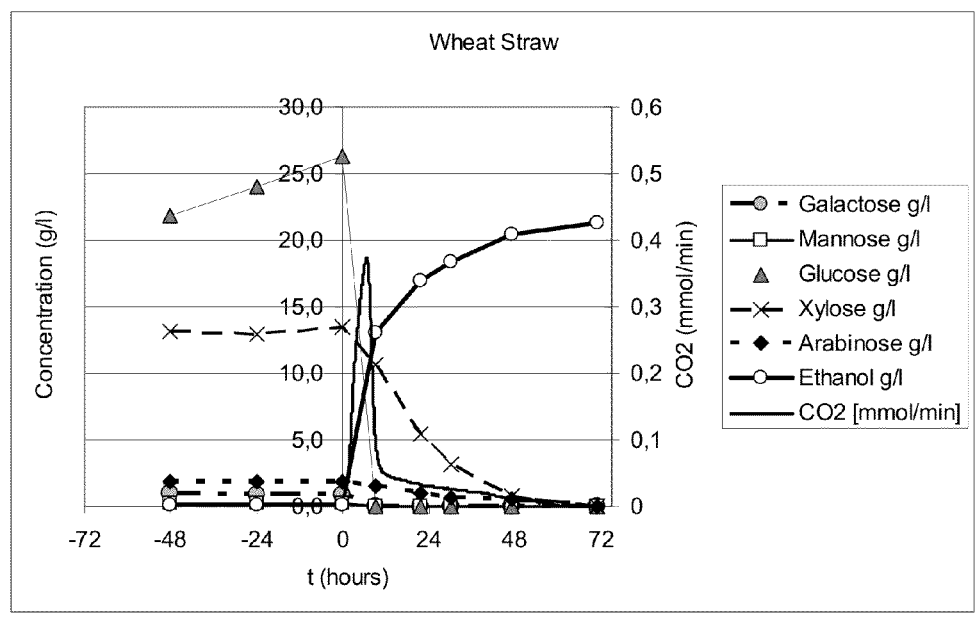
FIG. 19 sets out the performance of strain BIE252 in hydrolyzed wheat straw at 10% d.m. CO2 production rate, ethanol production and sugar conversion are shown.

The results are presented in FIG. 17 (corn fiber), 18 (corn stover) and 19 (wheat straw). In case of corn stover and wheat straw, feedstocks with a relatively low amount of galactose and arabinose but mainly consisting of glucose and xylose, all sugars were converted in 72 hours into $CO_2$ and ethanol. In case of corn fiber (FIG. 17), there is a low residual amount left of arabinose, galactose and xylose.

In the tables below the yield of the fermentation was calculated, on basis of the sugars liberated at the end of the hydrolysis and the amount of ethanol that was produced at the end of the fermentation.

TABLE 2

Total sugar released (g/l), ethanol produced (g/l) and ethanol yield ($g_{ethanol}/g_{sugar}$) of BAM fermentation of BIE252, for different lignocellulosic feedstock

| Lignocellulosic feedstock | Total sugar* (g/l) | Produced EtOH (g/l) | EtOH yield ($g_{ethanol}/g_{sugar}$) |
|---|---|---|---|
| Corn Stover | 45.4 | 22.7 | 0.50 |
| Wheat Straw | 42.7 | 20.7 | 0.48 |
| Corn Fiber | 58.1 | 27.4 | 0.47 |

*(released, monomeric sugar at start fermentation)

Based on the amount of ethanol produced at the end of the fermentation, as determined by the Anton Paar DMA 5000 density meter measurement, and the amount of pretreated feedstock that was being used, yields of the overall hydrolysis and fermentation were calculated, in duplicate. These figures are set out in table 3.

TABLE 3

Overall hydrolysis and fermentation yield (gallons of ethanol per ton dry matter) of BAM fermentation of BIE252, for different lignocellulosic feedstock

| Lignocellulosic feedstock | Overall hydrolysis and fermentation yield (gallons of ethanol per ton dry matter) 1st fermentation | Overall hydrolysis and fermentation yield (gallons of ethanol per ton dry matter) 2nd fermentation |
|---|---|---|
| Corn Stover | 81 | 81 |
| Wheat Straw | 72 | 73 |
| Corn Fiber | 67 | 69 |

Example 7

Stability Test of Strain BIE252

7.1 Stability of Strain BIE252

In order to test the stability of the strain BIE252, a single colony isolate was used to inoculate 25 ml of YEP 2% glucose. The optical density of the culture was measured at 600 nm. The culture was incubated overnight at 30° C. and 280 rpm in a rotary shaker.

After the overnight incubation, the optical density was determined. Based on the $OD^{600}$ values before and after incubation, the number of generations made during the incubations was calculated. 25 µl of the overnight culture was used to inoculate a flask containing 25 ml of fresh medium. The culture was incubated again under the same conditions as described above. This procedure was repeated until a culture was obtained in which the cells were at least one hundred generations apart from the initial single colony isolate. YEP medium supplemented with 2% glucose was chosen, because under these conditions no selection pressure is applied for maintaining the introduced genes in strain BIE252, needed for the conversion of arabinose and xylose.

Figure 20A:
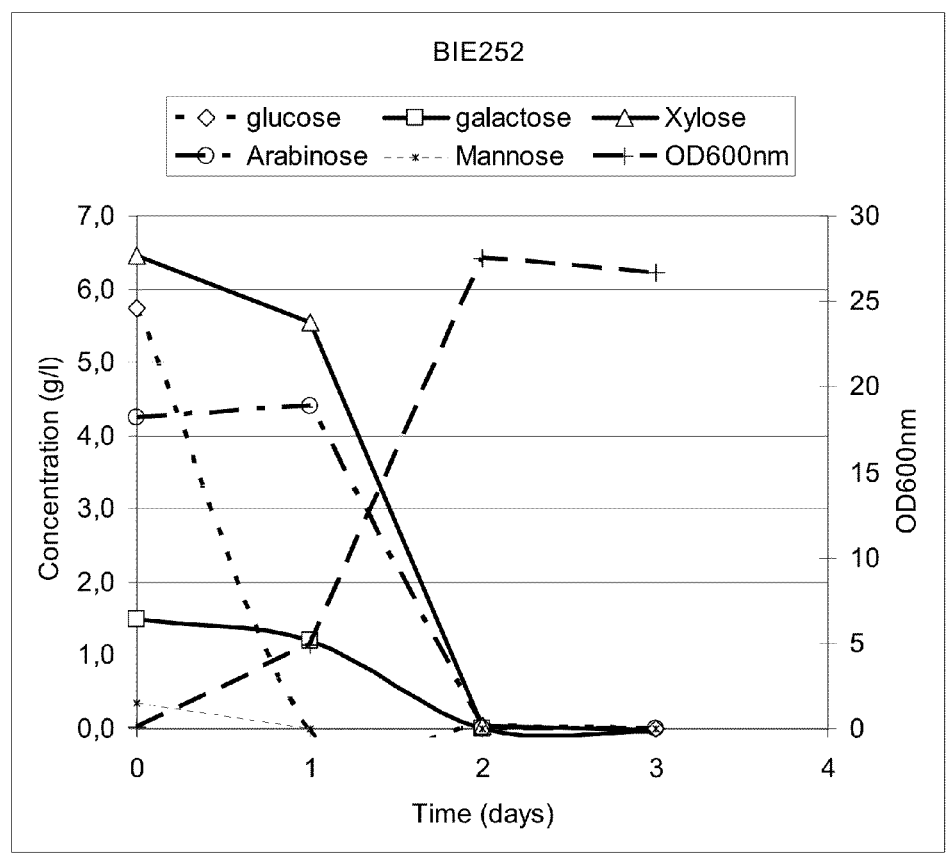
FIG. 20a sets out the sugar conversion (rate) of strain BIE252.

The cell culture obtained after at least 100 generations was diluted and plated on YPD-agar. Two single colony isolates were inoculated in Verduyn-medium 2% glucose. As a control, the parent strain BIE252 was taken along. The cultures were incubated overnight at 30° C. and 280 rpm in a rotary shaker. An aliquot of the overnight culture was used to inoculate a flask containing 25 ml of Verduyn medium supplemented with 1% glucose, 1% xylose, 0.7% arabinose, 0.3% galactose and 0.1% mannose at a start optical density of 0.15. At regular intervals, samples were taken for analysis: optical density measurements at 600 nm, and for determination of residual sugars by NMR. The results, as depicted in FIG. 20a (BIE252 culture prior to stability test), 20b (culture from colony of BIE252 after more than 100 generations) and 20c (culture from second colony of BIE252 after more than 100 generations), show that the behavior of the three strain cultures is virtually identical under the conditions tested. In other words, the performance in this growth medium has not changed; the strain is still able to utilize five different sugars with the same rates after culturing for more than 100 generations, indicating that the strain is genetically stable.

In addition, a quantitative PCR (Q-PCR) experiment was done to assess the copy number of BIE252 prior and after 100 generations cultivation in YEP medium supplemented with 2% glucose. The Q-PCR analysis was performed using the Bio-Rad iCycler iQ system from Bio-Rad (Bio-Rad Laboratories, Hercules, Calif., USA). The iQ SYBR Green Supermix (Bio-Rad) was used. Experiments were set up as suggested in the manual of the provider.

The stability of the strain BIE252 was assessed by determining the copy number of the xylA gene encoding xylose isomerase. As a reference single copy gene, the ACT1 gene was chosen.

The primers for the detection of the genes xylA and ACT1 are:

forward primer xylA SEQ ID NO 23
reverse primer xylA SEQ ID NO 24
forward primer ACT1 SEQ ID NO 25
reverse primer ACT1 SEQ ID NO 26

The results indicated that the copy number of BIE252 is about 8 copies of the xylA gene, relative to the ACT1 gene. The copy number was determined before and after the 100 generations cultivation on YEP-medium supplemented with 2% glucose, and appeared to be essentially the same, taking into account the limitations of the quantitative PCR analysis.

The chromosomal DNA of several colonies, before and after 100 generations cultivation in YEP medium supplemented with 2% glucose, was isolated. The chromosomal DNA is cut by XbaI. A Southern blot analysis is performed using the PCR product of primer pair SEQ ID NO: 23 and SEQ ID NO: 24 as a probe. The resulting autoradiogram is showing that the pattern of bands is not changed, which indicates that the strain is genetically stable after 100 generations of growth under non-selective conditions.

Figure 21:
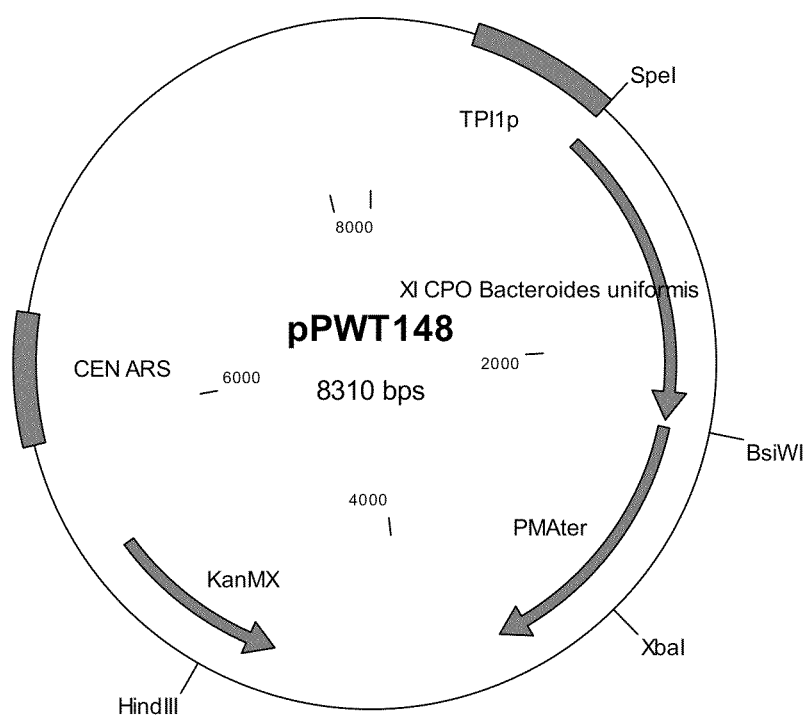
FIG. 21 sets out the physical map of plasmid pPWT148.
Figure 22:
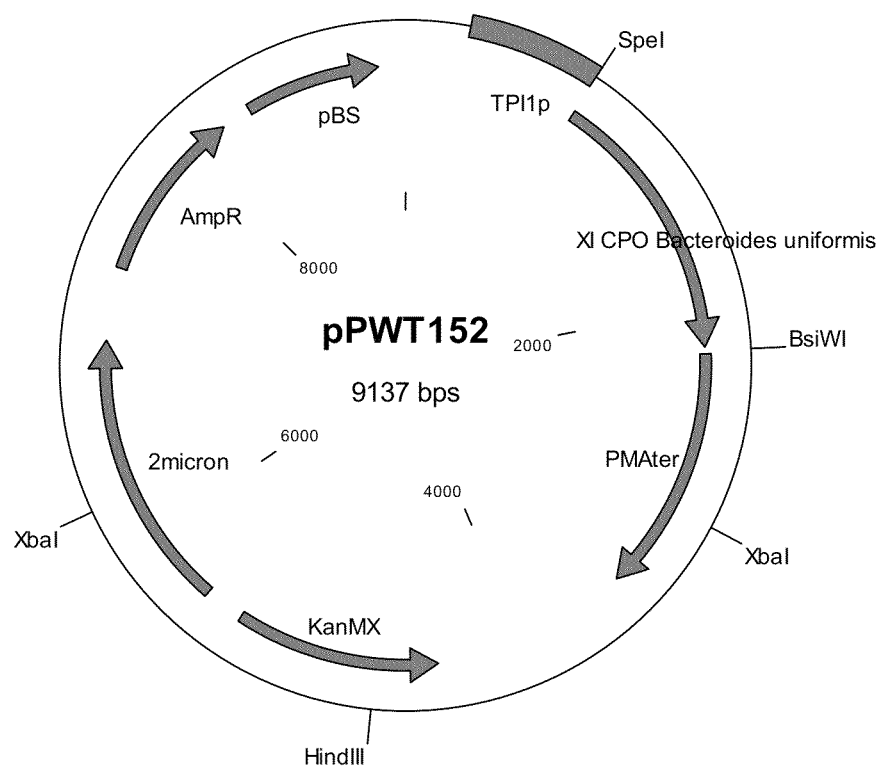
FIG. 22 sets out the physical map of plasmid pPWT152.

Comparative Experiment A 7.2 Stability of BIE201X9 Transformed with YEP and YCp Vectors Strain BIE201X9 was transformed with vectors pPWT148 (a YCp plasmid) and pPWT152 (a YEp plasmid). The physical map of plasmid pPWT148 is set out in FIG. 21. The physical map of plasmid pPWT152 is set out in FIG. 22. Transformation mixtures were plated on YPD-agar (per liter: 10 grams of yeast extract, 20 grams per liter peptone, 20 grams per liter dextrose, 20 grams of agar) containing 100 μg G418 (Sigma Aldrich) per ml. After two to four days, colonies appeared on the plates, whereas the negative control (i.e. no addition of DNA in the transformation experiment) resulted in blank YPD/G418-plates.

Three colonies of each transformation were used as a mixture for testing the stability. To this end, the mixed colonies were used to inoculate YEP medium, supplemented with 2% glucose and 100 μg G418/ml. Cells were incubated overnight at 30° C. and 280 rpm in a rotary shaker. The optical density was measured at 600 nm. The overnight culture was used to inoculate fresh YEP medium, supplemented with 2% glucose, and the same medium supplemented with 100 μg G418/ml, to a start optical density at 600 nm of 0.02. On basis of what is reported in the literature (vide supra), the expectation is that the cells that were cultured in the presence of G418 (i.e. selective pressure is applied), the majority of the cells will retain the plasmid inside the cell. However, in absence of G418, the cells are expected to lose their plasmid rapidly.

The cultures were incubated overnight at 30° C. and 280 rpm in a rotary shaker. The optical density was measured at 600 nm. On basis of the optical density measurements, it was calculated that the culture had made 8 generations in both media (i.e with and without G418). Dilutions were made and plated on YPD-plates with and without 100 μg G418/ml. Plates were incubated at 30° C. for approximately two days, or longer as needed to make colonies visible and countable.

In addition, 25 μl of the overnight culture was used to inoculate 25 ml of fresh YEP medium, supplemented with 2% glucose, and the same medium supplemented with 100 μg G418/ml. The cultures were incubated overnight at 30° C. and 280 rpm in a rotary shaker. The optical density was measured at 600 nm. On basis of the optical density measurements, it was calculated that the culture had made 8 extra generations in both media (i.e with and without G418). Dilutions were made and plated on YPD-plates with and without 100 μg G418/ml. Plates were incubated at 30° C. for approximately two days, or longer as needed to make colonies visible and countable.

On basis of the colonies that were counted on YDP-agar with and without G418, the stability could be calculated after 8 and 16 generations in presence or absence of G418. The results are summarized in the table 4.

TABLE 4

Stability of the strains of comparative experiment A (% G418 resistant clones)

| | BIE201X9-pPWT148 | BIE201X9-pPWT152 |
|---|---|---|
| % G418 resistant clones after 8 generations of growth in YEP 2% glucose | 4 | 12 |
| % G418 resistant clones after 16 generations of growth in YEP 2% glucose | 1 | 5 |
| % G418 resistant clones after 8 generations of growth in YEP 2% glucose and 100 μg G418/ml | 9 | 33 |
| % G418 resistant clones after 16 generations of growth in YEP 2% glucose and 100 μg G418/ml | 28 | 40 |

From the table, it can be seen that both YCp- and YEp-plasmids (i.e. pPWT148 and pPWT152 respectively) are not stably maintained in the transformed yeast cells, even if selection pressure is being applied during cultivation, in this case by the addition of G418 to the culture medium. It must be noted however that plasmid loss is much more severe in the absence of selection pressure.

This experiment in combination with example 7, provides insight that chromosomal integration of the xylose isomerase genes into the genome is necessary to obtain stable yeast transformants.

Example 8

Deletion of GAL80 Leads to a Better Arabinose Conversion

In Example 4 it was shown that the identified SNP in the GAL80 gene has a positive additive effect on the growth on arabinose, if the amplification of a part of chromosome VII is also present.

GAL80 encodes a transcriptional repressor involved in transcriptional regulation in response to galactose (Timson D J, et al. (2002) Biochem J 363(Pt 3):515-20). In conjunction with Gal4p and Gal3p, Gal80p coordinately regulates the expression of genes containing a GAL upstream activation site in their promoter (UAS-GAL), which includes the GAL metabolic genes GAL1, GAL10, GAL2, and GAL7 (reviewed in Lohr D, et al. (1995) FASEB J 9(9):777-87). Cells null for gal80 constitutively express GAL genes, even in non-inducing media (Torchia T E, et al. (1984) Mol Cell Biol 4(8):1521-7).

The hypothesis is that the SNP that was identified in the GAL80 gene influences the interaction between Gal80p, Gal3p and Gal4p. Hence, the expression of the galactose metabolic genes, including GAL2 encoding galactose permease, will be changed as well as compared to a yeast cell with a wild type GAL80 allele. Gal2p (galactose permease) is the main sugar transporter for arabinose (Kou et al (1970) J. Bacteriol. 103(3):671-678; Becker and Boles (2003) Appl Environ Microbiol. 69(7): 4144-4150).

Apparently, the SNP in the GAL80 gene has a positive effect on the ability to convert L-arabinose. In order to investigate whether the arabinose growth phenotype could further be improved, the coding sequence of the GAL80 gene was deleted in its entirety, using a PCR-mediated gene replacement strategy.

8.1 Disruption of the GAL80 Gene

Primers of SEQ ID NO 58 and 59 (the forward and reverse primers respectively) were used for amplification of the kanMX-marker from plasmid p427-TEF (Dualsystems Biotech, Schlieren, Switzerland). The flanks of the primers are homologous to the 5'-region and 3'-region of the GAL80 gene. Upon homologous recombination, the ORF of the GAL80 gene will be replaced by the kanMX marker, similar as described by Wach (Wach et al (1994) Yeast 10, 1793-1808). The obtained fragment is designated as the GAL80::kanMX fragment.

A yeast transformation of strain BIE252 was done with the purified GAL80::kanMX fragment according to the protocol described by Gietz and Woods (2002), Methods in Enzymology 350: 87-96). The construction of strain BIE252 has been described in EP10160622.6. Strain BIE252 is a xylose and arabinose fermenting strain of S. cerevisiae, which is a derivative of BIE201. Strain BIE252 also contains the GAL80 SNP.

The transformed cells were plated on YEPD-agar containing 100 μg/ml G418 for selection. The plates were incubated at 30° C. until colonies were visible. Plasmid p427-TEF was included as a positive control and yielded many colonies. MilliQ (i.e. no DNA) was included as a negative control and yielded no colonies. The GAL80::kanMX fragment yielded many colonies. Two independent colonies were tested by Southern blotting in order to verify the correct integration (data not shown). A colony with the correct deletion of the GAL80 gene was designated BIE252ΔGAL80.

8.2 Effect of GAL80 Gene Replacement on the Performance in the BAM

A BAM (Biological Activity Monitor; Halotec B V, Veenendaal, the Netherlands) experiment was performed. Single colony isolates of strain BIE252 and strain BIE252ΔGAL80 (a transformant in which the ORF of the GAL80 gene was correctly replaced by the kanMX marker) were used to inoculate Verduyn medium (Verduyn et al., Yeast 8:501-517, 1992) supplemented with 2% glucose. The precultures were incubated for approximately 24 hours at 30° C. and 280 rpm. Cells were harvested and inoculated in a synthetic model medium (Verduyn medium supplemented with 5% glucose, 5% xylose, 3.5% arabinose, 1% galactose and 0.5% mannose, pH 4.2) at a cell density of about 1 gram dry weight per kg of medium. $CO_2$ production was monitored constantly. Sugar conversion and product formation was analyzed by NMR. The data represent the residual amount of sugars at the indicated time points (glucose, arabinose, galactose, mannose and xylose in grams per liter) and the formation of (by-)products (ethanol, glycerol, and the like). Growth was monitored by following optical density of the culture at 600 nm. The experiment was running for approximately 72 hours.

The graphs are displayed in FIG. 23 (BIE252) and 24 (BIE252ΔGAL80).

The experiments clearly show that reference strain BIE252 converted glucose and mannose rapidly. After glucose depletion (around 10 hours), the conversion of xylose and arabinose commenced. Some galactose was already being fermented around the 10 hours time point, which might be due to the GAL80 SNP in this strain, which would allow (partial) simultaneous utilisation of glucose and galactose. At the end of the experiment, around 72 hours, almost all sugars (about 99%) were converted. An ethanol yield of 0.37 grams of ethanol per gram sugar was obtained.

Figure 20B:
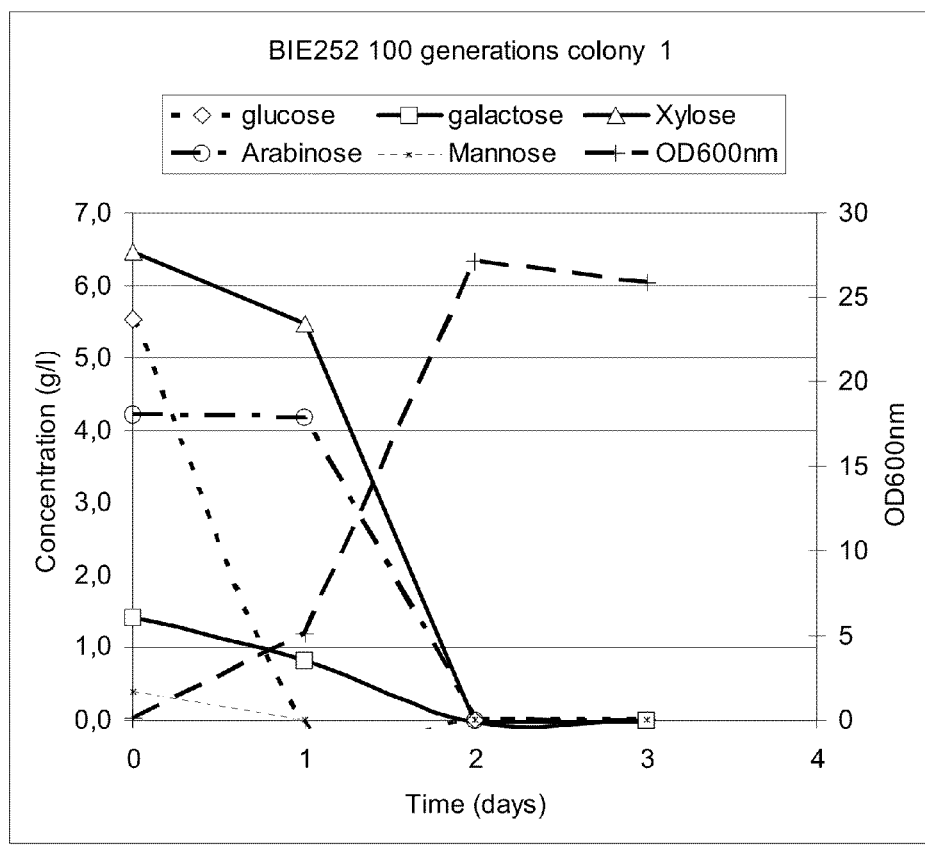
FIG. 20b sets out the sugar conversion (rate) of a single colony isolate of strain BIE252 after cultivation for more than 100 generations in YEP-medium with 2% glucose.
Figure 20C:
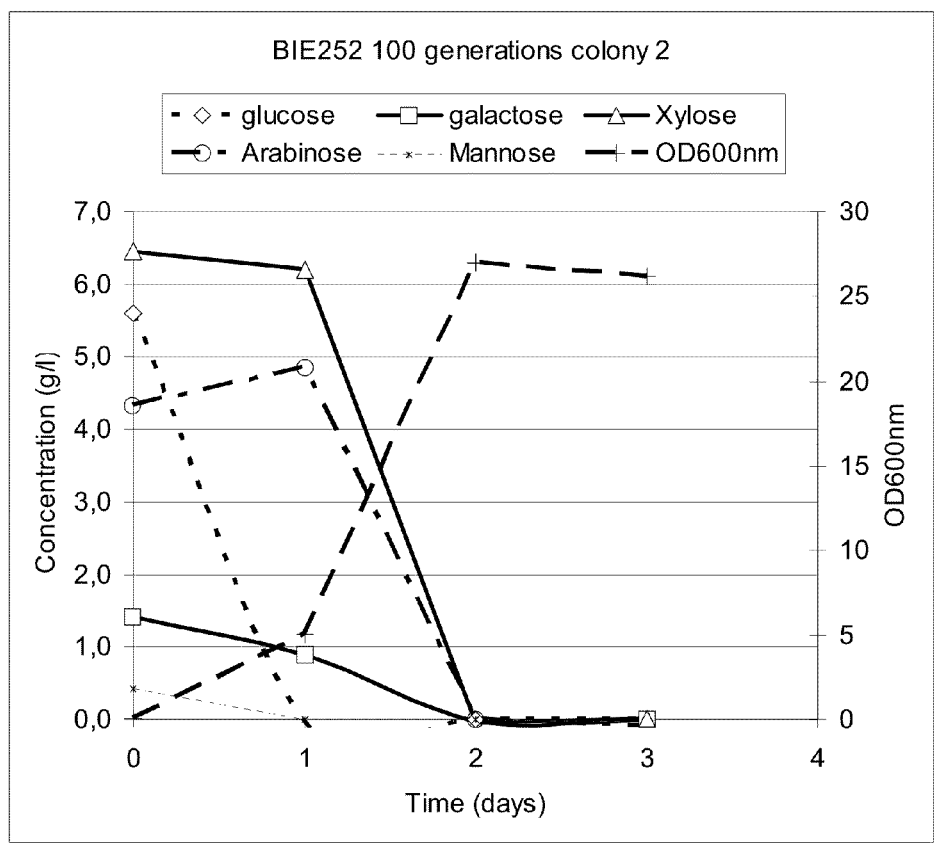
FIG. 20c sets out the sugar conversion (rate) of a single colony isolate of strain BIE252 after cultivation for more than 100 generations in YEP-medium with 2% glucose.

Strain BIE252ΔGAL80 exhibits faster sugar conversion ability than strain BIE252. Also in case of this strain, mannose and glucose are converted in the first hours of fermentation. However, as opposed to strain BIE252, in this transformant there is some co-consumption of glucose, galactose and mannose with arabinose and especially xylose. In general, sugar consumption is faster, leading to a more complete use of all available sugars. This is also apparent from the $CO_2$ evolution in time. In case of BIE252, a first peak is observed, which is basically the CO2 formed from glucose and mannose. After reaching a minimum of just above 10 ml/hr (FIG. 20) a second, more flat peak is observed. In case of BIE252ΔGAL80 however (FIG. 21), the second peak appears as a tail of the first peak, due to an intensified co-use of glucose, xylose, arabinose, mannose and galactose, as is apparent from the sugar analysis by NMR. In the parent strain BIE252, the use of the different sugars is more sequential. Hence, the yield of strain BIE252ΔGAL80 is higher at the end of the experiment (72 h): 0.40 grams of ethanol per gram sugar.

In conclusion, the deletion of the ORF of the GAL80 gene resulted in a further improved performance, as was tested in strain BIE252.

The invention claimed is:

1. A transformed *Saccharomyces cerevisiae* cell suitable for producing ethanol from a sugar composition comprising glucose, galactose, xylose, arabinose and mannose wherein said cell comprises about eight copies of at least one xylose isomerase gene, and from two to four copies of L-arabinose isomerase (araA), L-ribulokinase (araB), and L-ribulose-5-phosphate 4-epimerase (araD) genes, wherein said genes are heteroloqous and are integrated into the cell genome.

2. The yeast cell according to claim 1, wherein said cell is capable of converting at least 90% of glucose, xylose arabinose, galactose and mannose available, into ethanol.

3. The yeast cell according to claim 1, wherein said cell comprises a disruption or deletion of the GAL80 (transcriptional repressor) gene.

4. The yeast cell according claim 1, wherein said cell comprises overexpressed pentose phosphate pathway genes TAL1 (transaldolase), TKL1 (transketolase), RPE1 (ribulose-phosphate 3-epimerase), and RKI1 (ribulose-5-phosphate isomerase).

5. The yeast cell according to claim 1, wherein said cell comprises a XKS1 (xylulose kinase) gene.

6. The yeast cell according to claim 1, wherein an aldose reductase gene is deleted.

7. The yeast cell according to claim 1, wherein all genes exogenous to said cell are integrated into the genome of said cell.

8. The yeast cell according to claim 1, wherein the genes have been introduced in said cell by introduction into a host cell:
 a) a cluster consisting of said genes araA, araB and araD under control of a strong constitutive promoter;
 b) a cluster consisting of PPP-genes TAL1, TKL1, RPE1 and RKI1, optionally under control of strong constitutive promoter; and deletion of an aldose reductase gene;
 c) a cluster consisting of a xylA (xylose isomerase) gene and a XKS1 gene under control of strong constitutive promoter;
 d) a construct comprising a xylA gene under control of a strong constitutive promoter, which has the ability to integrate into the genome on multiple loci;
 and adaptive evolution of the mixed sugar construct for producing said mixed sugar cell.

9. The yeast cell according to claim 8, wherein said cell is an inhibitor resistant cell.

10. The yeast cell according to claim 8, wherein said cell is an industrial cell.

11. A process for producing ethanol from a sugar composition comprising glucose, galactose, arabinose and xylose, wherein said sugar composition is fermented with a yeast cell according to claim 1.

12. The process according to claim 11, wherein said sugar composition is produced from lignocellulosic material by:
 a) pretreatment of at least one lignocellulosic material to produce pretreated lignocellulosic material;
 b) enzymatic treatment of the pretreated lignocellulosic material to produce said sugar composition.

13. The process according to claim 11, wherein said fermentation is conducted anaerobically.

14. The yeast cell according to claim 9, wherein said cell is an industrial cell.

15. The process according to claim 12, wherein said fermentation is conducted anaerobically.

16. The yeast cell of claim 1, wherein said at least one xylose isomerase gene is a xylA gene.

* * * * *

SEQUENCE LISTING

<160> NUMBER OF SEQ ID NOS: 26

<210> SEQ ID NO 1
<211> LENGTH: 18215
<212> TYPE: DNA
<213> ORGANISM: Artificial Sequence
<220> FEATURE:
<223> OTHER INFORMATION: Synthetic plasmid

<400> SEQUENCE: 1

```
ggccaagatg gccgatctgc attttcata ataatcctcg gtactttcta caagatcaat      60
taaattccaa tcaaaaatcg tcttttgcaa gattttgaag tcacagtact tttcattttc     120
aatgtcaaca gcgccccatt tgtattgtct tcctttaact ttttcgccct tttcattaaa    180
aatgtactca ttagatgcaa ttatactgaa tggatatttt tgaaaaatat cttgtgttgc    240
attcaaaact tcatcgccga aaaagaaaca tacagggata tcttgtactc ttattatttc    300
tctaacttgt gttttgaagt ttttcaattc ctctttcgtt agcaaatctg atttagcaat    360
aaccgggatt aaattcactc tcttcgctaa ttttttcatt gttacgacgt ctaaagtatc    420
aattccctta tttgaaggtc tcagaaagta caaacaacaa tggactctat tatcaaccat    480
```

```
ttttgtccta tcaggttgtt cttcttggaa aatgtacgat cttatttctt catcaatata     540
gtttctagac tgcagcccgg gatccgtcga caagcttgtg gagaggtgac ttcatgaacc     600
aagtgtctgt cgatatacaa caaaaaggaa ccattttcat cttgatggac aacatgtgca     660
tcaaaaacct tatcgtaaag agttcttgga cccttggatg gagtgtaaac catgatttaa     720
aacagcaaat aataaaaatc gatagcgaca aaaactgtca atttcaatat tctttatatt     780
tgttgactgc ttagatattt tgagaaaatt cagcggaaac agcgtgatga gtgagttaag     840
ttctgctgtt taaataagta ttcaactact attgaagccg actcatgaag ccggttacgg     900
acaaaaccgg gcaaatttcg ccggtcccgg aattttcgtt ccgcaataa aagaaccgct     960 catcatcata gcgccagggt agtatactat agaaggtcag actaaactga gtcatctaga    1020
gtaatgacgc cttagtagct tttacatctt cataagaaaa ggaaacttgt agaatggcct    1080
ggcgatttgt ttgctttctt gtgatgaaga aatttcgatg cgattaaccg gcaaaatcag    1140
taaaggtatt tcgcggaggc ggccttcaat catcgaatac tacgtcttaa tatgatgtac    1200
tgtggttcat attttcaagt agtgttagta aatttgtata cgttcatgta agtgtgtatc    1260
ttgagtgtct gtatgggcgc ataaacgtaa gcgagacttc caaatggagc aaacgagaag    1320
agatctttaa agtattatag aagagctggg caggaactat tatgacgtaa agccttgacc    1380
ataataaaga cgattctttg tccctctata caaacatctt gcaaagatac caaatatttt    1440
caaatcctac tcaataaaaa attaatgaat aaattagtgt gtgtgcatta tatatattaa    1500
aaattaagaa ttagactaaa taagtgtttt ctaaaaaaat attaaagttg aaatgtgcgt    1560
gttgtgaatt gtgctctatt agaataatta tgacttgtgt gcgtttcata ttttaaaata    1620
ggaaataacc aagaaagaaa aagtaccatc cagagaaacc aattatatca aatcaaataa    1680
aacaaccagc ttcggtgtgt gtgtgtgtgt gaagctaaga gttgatgcca tttaatctaa    1740
aaattttaag gtgtgtgtgt ggataaaata ttagaatgac aattcgaatt gcgtaccta    1800 gtcaaaaaat tagccttttta attctgctgt aacccgtaca tgcccaaaat aggggcggg    1860 ttacacagaa tatataacat cgtaggtgtc tgggtgaaca gtttattcct ggcatccact    1920
aaatataatg gagcccgctt tttaagctgg catccagaaa aaaaagaat cccagcacca    1980 aaatattgtt ttcttcacca accatcagtt cataggtcca ttctcttagc gcaactacag    2040
agaacagggg cacaaacagg caaaaaacgg gcacaacctc aatggagtga tgcaacctgc    2100
ctggagtaaa tgatgacaca aggcaattga cccacgcatg tatctatctc attttcttac    2160
accttctatt accttctgct ctctctgatt tggaaaaagc tgaaaaaaa ggttgaaacc    2220 agttccctga aattattccc ctacttgact aataagtata taaagacggt aggtattgat    2280
tgtaattctg taaatctatt tcttaaactt cttaaattct acttttatag ttagtctttt    2340
ttttagtttt aaaacaccaa gaacttagtt tcgaataaac acacataaac aaacaaaatg    2400
ttatcagtac ctgattatga gttttggttt gttaccggtt cacaacacct ttatggtgaa    2460
gaacaattga agtctgttgc taaggatgcg caagatattg cggataaatt gaatgcaagc    2520
ggcaagttac cttataaagt agtctttaag gatgttatga cgacggctga agtatcacc    2580 aactttatga agaagttaa ttacaatgat aaggtagccg tgttattac ttggatgcac    2640 acattctcac cagctaagaa ctggattcgt ggaactgaac tgttacaaaa accattatta    2700
cacttagcaa cgcaatattt gaataatatt ccatatgcag acattgactt tgattacatg    2760
aaccttaacc aaagtgccca tggcgaccgc gagtatgcct acattaacgc ccggttgcag    2820
```

```
aaacataata agattgttta cggctattgg ggcgatgaag atgtgcaaga gcagattgca    2880
cgttgggaag acgtcgccgt agcgtacaat gagagcttta agttaaggt tgctcgcttt     2940 ggcgacacaa tgcgtaatgt ggccgttact gaaggtgaca aggttgaggc tcaaattaag    3000
atgggctgga cagttgacta ttatggtatc ggtgacttag ttgaagagat caataaggtt    3060
tcggatgctg atgttgataa ggaatacgct gacttggagt ctcggtatga atggtccaa     3120 ggtgataacg atgcggacac gtataaacat tcagttcggg ttcaattggc acaatatctg    3180
ggtattaagc ggttcttaga agaggcggt tacacagcct ttaccacgaa ctttgaagat     3240
ctttggggga tggagcaatt acctggtcta gcttcacaat tattaattcg tgatgggtat    3300
ggttttggtg ctgaaggtga ctggaagacg gctgctttag gacgggttat gaagattatg    3360
tctcacaaca agcaaaccgc ctttatggaa gactacacgt tagacttgcg tcatggtcat    3420
gaagcgatct taggttcaca catgttggaa gttgatccgt ctatcgcaag tgataaacca    3480
cgggtcgaag ttcatccatt ggatattggg ggtaaagatg atcctgctcg cctagtattt    3540
actggttcag aaggtgaagc aattgatgtc accgttgccg atttccgtga tgggttcaag    3600
atgattagct acgcggtaga tgcgaataag ccagaagccg aaacacctaa tttaccagtt    3660
gctaagcaat tatggacccc aaagatgggc ttaaagaaag gtgcactaga atggatgcaa    3720
gctggtggtg gtcaccacac gatgctgtcc ttctcgttaa ctgaagaaca aatggaagac    3780
tatgcaacca tggttggcat gactaaggca ttcttaaagt aagtgaattt actttaaatc    3840
ttgcatttaa ataaatttc tttttatagc tttatgactt agtttcaatt tatatactat     3900
tttaatgaca ttttcgattc attgattgaa agctttgtgt ttttcttga tgcgctattg     3960 cattgttctt gtctttttcg ccacatgtaa tatctgtagt agatacctga tacattgtgg    4020
atgctgagtg aaattttagt taataatgga ggcgctctta ataattttgg ggatattggc    4080
tttttttttt aaagtttaca aatgaatttt ttccgccagg atcgtacgcc gcggaaccgc    4140
cagatattca ttacttgacg caaaagcgtt tgaaataatg acgaaaaaga aggaagaaaa    4200
aaaaagaaaa ataccgcttc taggcgggtt atctactgat ccgagcttcc actaggatag    4260
cacccaaaca cctgcatatt tggacgacct ttacttacac caccaaaaac cactttcgcc    4320
tctcccgccc ctgataacgt ccactaattg agcgattacc tgagcggtcc tcttttgttt    4380
gcagcatgag acttgcatac tgcaaatcgt aagtagcaac gtctcaaggt caaaactgta    4440
tggaaacctt gtcacctcac ttaattctag ctagcctacc ctgcaagtca agaggtctcc    4500
gtgattccta gccaccctcaa ggtatgcctc tccccggaaa ctgtggcctt ttctggcaca    4560
catgatctcc acgatttcaa catataaata gcttttgata atggcaatat taatcaaatt    4620
tattttactt ctttcttgta acatctctct tgtaatccct tattccttct agctattttt    4680
cataaaaaac caagcaactg cttatcaaca cacaaacact aaatcaaaat gaatttagtt    4740
gaaacagccc aagcgattaa aactggcaaa gtttctttag gaattgagct tggctcaact    4800
cgaattaaag ccgttttgat cacggacgat tttaatacga ttgcttcggg aagttacgtt    4860
tgggaaaacc aatttgttga tggtacttgg acttacgcac ttgaagatgt ctggaccgga    4920
attcaacaaa gttatacgca attagcagca gatgtccgca gtaaatatca catgagtttg    4980
aagcatatca atgctattgg cattagtgcc atgatgcacg ataccatagc atttgatcaa    5040
caagcgaaat tattagttcc gtttcggact tggcgtaata acattacggg gcaagcagca    5100
gatgaattga ccgaattatt tgatttcaac attccacaac ggtggagtat cgcacactta    5160
taccaggcaa tcttaaataa tgaagcgcac gttaaacagg tggacttcat aacaacgctg    5220
```

```
gctggctatg taacctggaa attgtcgggt gagaaagttc taggaatcgg tgatgcgtct    5280
ggcgttttcc caattgatga aacgactgac acatacaatc agacgatgtt aaccaagttt    5340
agccaacttg acaaagttaa accgtattca tgggatatcc ggcatatttt accgcgggtt    5400
ttaccagcgg gagccattgc tggaaagtta acggctgccg gggcgagctt acttgatcag    5460
agcggcacgc tcgacgctgg cagtgttatt gcaccgccag aagggatgc tggaacagga    5520 atggtcggta cgaacagcgt ccgtaaacgc acgggtaaca tctcggtggg aacctcagca    5580
ttttcgatga acgttctaga taaaccattg tctaaagtct atcgcgatat tgatattgtt    5640
atgacgccag atgggtcacc agttgcaatg gtgcatgtta ataattgttc atcagatatt    5700
aatgcgtggg caacgatttt tcatgagttt gcagcccggt tgggaatgga attgaaaccg    5760
gatcgattat atgaaacgtt attcttggaa tcaactcgcg ctgatgcgga tgctggaggg    5820
ttggctaatt atagttatca atccggtgag aatattacta agattcaagc tggtcggccg    5880
ctatttgtac ggacaccaaa cagtaaattt agtttaccga actttatgtt gactcaatta    5940
tatgcggcgt tcgcaccct ccaacttggt atggatattc ttgttaacga gaacatgtt    6000 caaacgacg ttatgattgc acagggtgga ttgttccgaa cgccggtaat tggccaacaa    6060
gtattggcca acgcactgaa cattccgatt actgtaatga gtactgctgg tgaaggcggc    6120
ccatggggga tggcagtgtt agccaacttt gcttgtcggc aaactgcaat gaacctagaa    6180
gatttcttag atcaagaagt cttaaagag ccagaaagta tgacgttgag tccagaaccg    6240
gaacgggtgg ccggatatcg tgaattaatt caacgttatc aagctggctt accagttgaa    6300
gcagcggctg ggcaagcaat caaatattag agcttttgat taagccttct agtccaaaaa    6360
acacgttttt ttgtcattta tttcattttc ttagaatagt ttagtttatt cattttatag    6420
tcacgaatgt tttatgattc tatatagggt tgcaaacaag catttttcat tttatgttaa    6480
aacaatttca ggtttacctt ttattctgct tgtggtgacg cgggtatccg cccgctcttt    6540
tggtcaccca tgtatttaat tgcataaata attcttaaaa gtggagctag tctatttcta    6600
tttacatacc tctcatttct catttcctcc actagtagag aattttgcca tcggacatgc    6660
taccttacgc ttatatctct cattggaata tcgttttctg attaaaacac ggaagtaaga    6720
acttaattcg ttttttcgttg aactatgttg tgccagcgta acattaaaaa agagtgtaca    6780
aggccacgtt ctgtcaccgt cagaaaaata tgtcaatgag gcaagaaccg ggatggtaac    6840
aaaaatcacg atctgggtgg gtgtgggtgt attggattat aggaagccac gcgctcaacc    6900
tggaattaca ggaagctggt aatttttttgg gtttgcaatc atcaccatct gcacgttgtt    6960
ataatgtccc gtgtctatat atatccattg acggtattct attttttttgc tattgaaatg    7020 agcgtttttt gttactacaa ttggttttac agacggaatt ttccctattt gtttcgtccc    7080 attttttcctt ttctcattgt tctcatatct taaaaggtc ctttcttcat aatcaatgct    7140
ttcttttact taatatttta cttgcattca gtgaatttta atacatattc ctctagtctt    7200
gcaaaatcga tttagaatca agataccagc ctaaaaatgc tagaagcatt aaaacaagaa    7260
gtttatgagg ctaacatgca gcttccaaag ctgggcctgg ttacttttac ctggggcaat    7320
gtctcgggca ttgaccggga aaaggccta ttcgtgatca agccatctgg tgttgattat    7380
ggtgaattaa aaccaagcga tttagtcgtt gttaacttac agggtgaagt ggttgaaggt    7440
aaactaaatc cgtctagtga tacgccgact catacggtgt tatataacgc ttttcctaat    7500
attggcggaa ttgtccatac tcattcgcca tgggcagttg cctatgcagc tgctcaaatg    7560
```

```
gatgtgccag ctatgaacac gacccatgct gatacgttct atggtgacgt gccggccgcg   7620
gatgcgctga ctaaggaaga aattgaagca gattatgaag caacacgggt aaaaccatt    7680
gtgaagacgt tccaagaacg gggcctcgat tatgaagctg taccagcctc attagtcagc   7740
cagcacggcc catttgcttg gggaccaacg ccagctaaag ccgtttacaa tgctaaagtg   7800
ttggaagtgg ttgccgaaga agattatcat actgcgcaat tgacccgtgc aagtagcgaa   7860
ttaccacaat atttattaga taagcattat ttacgtaagc atggtgcaag tgcctattat   7920
ggtcaaaata tgcgcattc taaggatcat gcagttcgca agtaaacaaa tcgctcttaa    7980
atatatacct aaagaacatt aaagctatat tataagcaaa gatacgtaaa ttttgcttat   8040
attattatac acatatcata tttctatatt tttaagattt ggttatataa tgtacgtaat   8100
gcaaaggaaa taaattttat acattattga acagcgtcca agtaactaca ttatgtgcac   8160
taatagttta gcgtcgtgaa gactttattg tgtcgcgaaa agtaaaaatt ttaaaaatta   8220
gagcaccttg aacttgcgaa aaaggttctc atcaactgtt taaaaacgcg tgtcttctgt   8280
gtttcagttc agggcttttc ggaggatgtg aatcgacggc gtactgtcct tgggaacttt   8340
gtctacgtat tttcacttcc tcagcgaatc cagagactat cttgggaaat tcgacaggac   8400
agtctgttga caaccgactc ccttttgact tcataataaa aattcaatga cgcaaaagga   8460
attttaggtt tttattatt atttatttat ttctgttaat tgatccttt ctttccacta    8520
ccaacaacaa aaaaggggg aaaaagatgt ataatctaaa agacactaat ctgctcttga    8580
tatccttatt atgtaatgga ataactcata taaatgtaaa atagaacttc aaattaatat   8640
tataatgata gtcgaggtca gacacactta taatacatta agtaaagaaa aaaaaatgtc   8700
tgtcatcgag gtctcttttg tgtcgctaac aaaacatcac taaatacgaa gacactttgc   8760
atgggaagga tgcagcaaat ggcaaactaa cgggccattg attggtttac ctcttctatt   8820
tgtattacga ccagaaagaa cgaatggttt tcatcaatga ggtaggaaac gacctaaata   8880
taatgtagca tagataaaat cttttgtactg tatggttgca atgccttctt gattagtatc   8940
gaatttcctg aataatttg ttaatctcat tagccaaact aacgcctcaa cgaatttatc    9000
aaactttagt tcttttcctg ttccatttct gtttataaac tcagcatatt ggtcaaatgt   9060
tttctcgcta acttcaaaag gtattagata tcctagttct tgaagtgagt tatgaaattc   9120
gcttacagaa atggtgagcg atccgttgat atcattgtcc acataaactt ttctccaact   9180
tttcactctt ttgtataggg cgatgaattc tgcctggttg acagtgccaa acctggaagc   9240
accaaataaa tttatcagcg catctactga tgatatacaa aaatgggagt tgtcgtcgtt   9300
ttgtagtaag ttctgtagtt cctcagctgt cagtcggttt ttgcccttta catcatggtt   9360
atgaaatagc tgtgtggcca cttgcatgtc tcgtacatct tctctgctat cgaacgaagc   9420
aggtgcaact ttcttcaaga gttgtgcagg cactgcttga ttgtgaatta ggggaggagg   9480
agaggaagct atccgttgag cggaagtgtt caagttgtta taatgggttg gcgctggagg   9540
tataggcctg cctgctggtt tctgtgcgat aacattatat ctaggatcca caggtgtttt   9600
cgtatgtctt ggagaataac tttggggaga accataggag tggtgaccgt ttctgctct    9660
gttttttgtta tattgagttt gtaagggaat tggagctgag tggactctag tgttgggagt   9720
ttgtgcttga gtaaccggta ccacggctcc tcgctgcaga cctgcgagca gggaaacgct   9780
cccctcacag tcgcgttgaa ttgtccccac gccgcgcccc tgtagagaaa tataaaaggt   9840
taggatttgc cactgaggtt cttctttcat atacttcctt ttaaaatctt gctaggatac   9900
agttctcaca tcacatccga acataaacaa ccatgggtaa ggaaaagact cacgtttcga   9960
```

```
ggccgcgatt aaattccaac atggatgctg atttatatgg gtataaatgg gctcgcgata    10020
atgtcgggca atcaggtgcg acaatctatc gattgtatgg gaagcccgat gcgccagagt    10080
tgtttctgaa acatggcaaa ggtagcgttg ccaatgatgt tacagatgag atggtcagac    10140
taaactggct gacggaattt atgcctcttc cgaccatcaa gcattttatc cgtactcctg    10200
atgatgcatg gttactcacc actgcgatcc ccggcaaaac agcattccag gtattagaag    10260
aatatcctga ttcaggtgaa atattgttg atgcgctggc agtgttcctg cgccggttgc     10320
attcgattcc tgtttgtaat tgtccttta acagcgatcg cgtatttcgt ctcgctcagg     10380
cgcaatcacg aatgaataac ggtttggttg atgcgagtga ttttgatgac gagcgtaatg    10440
gctggcctgt tgaacaagtc tggaaagaaa tgcataagct tttgccattc tcaccggatt    10500
cagtcgtcac tcatggtgat ttctcacttg ataaccttat ttttgacgag gggaaattaa    10560
taggttgtat tgatgttgga cgagtcggaa tcgcagaccg ataccaggat cttgccatcc    10620
tatggaactg cctcggtgag ttttctcctt cattacagaa acggcttttt caaaaatatg    10680
gtattgataa tcctgatatg aataaattgc agtttcattt gatgctcgat gagttttcct    10740
aatcagtact gacaataaaa agattcttgt tttcaagaac ttgtcatttg tatagttttt    10800
ttatattgta gttgttctat tttaatcaaa tgttagcgtg atttatattt tttttcgcct    10860
cgacatcatc tgcccagatg cgaagttaag tgcgcagaaa gtaatatcat gcgtcaatcg    10920
tatgtgaatg ctggtcgcta tactgctgtc gattcgatac taacgccgcc atccagggta    10980
ccatcctttt gttgtttccg ggtgtacaat atggacttcc tcttttctgg caaccaaacc    11040
catacatcgg gattcctata ataccttcgt tggtctccct aacatgtagg tggcggaggg    11100
gagatataca atagaacaga taccagacaa gacataatgg gctaaacaag actacaccaa    11160
ttacactgcc tcattgatgg tggtacataa cgaactaata ctgtagccct agacttgata    11220
gccatcatca tatcgaagtt tcactaccct ttttccattt gccatctatt gaagtaataa    11280
taggcgcatg caacttcttt tcttttttt tcttttctct ctcccccgtt gttgtctcac      11340
catatccgca atgacaaaaa aaatgatgga agacactaaa ggaaaaaatt aacgacaaag    11400
acagcaccaa cagatgtcgt tgttccagag ctgatgaggg gtatcttcga acacacgaaa    11460 cttttttcctt ccttcattca cgcacactac tctctaatga gcaacggtat acggccttcc     11520
ttccagttac ttgaatttga aataaaaaaa gtttgccgct ttgctatcaa gtataaatag    11580
acctgcaatt attaatcttt tgtttcctcg tcattgttct cgttcccttt cttccttgtt    11640
tctttttctg cacaatattt caagctatac caagcataca atcaactatc tcatatacaa    11700
tgcctcaatc ctgggaagaa ctggccgctg ataagcgcgc ccgcctcgca aaaaccatcc    11760
ctgatgaatg gaaagtccag acgctgcctg cggaagacag cgttattgat ttcccaaaga    11820
aatcggggat cctttcagag gccgaactga agatcacaga ggcctccgct gcagatcttg    11880
tgtccaagct ggcggccgga gagttgacct cggtggaagt tacgctagca ttctgtaaac    11940
gggcagcaat cgcccagcag ttaacaaact gcgcccacga gttcttccct gacgccgctc    12000
tcgcgcaggc aagggaactc gatgaatact acgcaaagca caagagaccc gttggtccac    12060
tccatggcct cccatctct ctcaaagacc agcttcgagt caagggctac gaaacatcaa    12120
tgggctacat ctcatggcta aacaagtacg acgaagggga ctcggttctg acaaccatgc    12180
tccgcaaagc cggtgccgtc ttctacgtca agacctctgt cccgcagacc ctgatggtct    12240
gcgagacagt caacaacatc atcgggcgca ccgtcaaccc acgcaacaag aactggtcgt    12300
```

```
gcggcggcag ttctggtggt gagggtgcga tcgttgggat tcgtggtggc gtcatcggtg   12360
taggaacgga tatcggtggc tcgattcgag tgccggccgc gttcaacttc ctgtacggtc   12420
taaggccgag tcatgggcgg ctgccgtatg caaagatggc gaacagcatg gagggtcagg   12480
agacggtgca cagcgttgtc gggccgatta cgcactctgt tgaggacctc cgcctcttca   12540
ccaaatccgt cctcggtcag gagccatgga aatacgactc caaggtcatc cccatgccct   12600
ggcgccagtc cgagtcggac attattgcct ccaagatcaa gaacggcggg ctcaatatcg   12660
gctactacaa cttcgacggc aatgtccttc cacaccctcc tatcctgcgc ggcgtggaaa   12720
ccaccgtcgc cgcactcgcc aaagccggtc acaccgtgac cccgtggacg ccatacaagc   12780
acgatttcgg ccacgatctc atctcccata tctacgcggc tgacggcagc gccgacgtaa   12840
tgcgcgatat cagtgcatcc ggcgagccgg cgattccaaa tatcaaagac ctactgaacc   12900
cgaacatcaa agctgttaac atgaacgagc tctgggacac gcatctccag aagtggaatt   12960
accagatgga gtaccttgag aaatggcggg aggctgaaga aaaggccggg aaggaactgg   13020
acgccatcat cgcgccgatt acgcctaccg ctgcggtacg gcatgaccag ttccggtact   13080
atgggtatgc ctctgtgatc aacctgctgg atttcacgag cgtggttgtt ccggttacct   13140
ttgcggataa gaacatcgat aagaagaatg agagtttcaa ggcggttagt gagcttgatg   13200
ccctcgtgca ggaagagtat gatccggagg cgtaccatgg ggcaccggtt gcagtgcagg   13260
ttatcggacg gagactcagt gaagagagga cgttggcgat tgcagaggaa gtggggaagt   13320
tgctgggaaa tgtggtgact ccataggtcg agaatttata cttagataag tatgtactta   13380
caggtatatt tctatgagat actgatgtat acatgcatga taatatttaa acggttatta   13440
gtgccgattg tcttgtgcga taatgacgtt cctatcaaag caatacactt accacctatt   13500
acatgggcca agaaaatatt ttcgaacttg tttagaatat tagcacagag tatatgatga   13560
tatccgttag attatgcatg attcattcct acaacttttt cgtagcataa ggattaatta   13620
cttggatgcc aataaaaaaa aaaaacatcg agaaaatttc agcatgctca gaaacaattg   13680
cagtgtatca aagtaaaaaa aagattttcg ctacatgttc cttttgaaga aagaaaatca   13740
tggaacatta gatttacaaa aatttaacca ccgctgatta acgattagac cgttaagcgc   13800
acaacaggtt attagtacag agaaagcatt ctgtggtgtt gccccggact ttcttttgcg   13860
acataggtaa atcgaatacc atcatactat cttttccaat gactccctaa agaaagactc   13920
ttcttcgatg ttgtatacgt tggagcatag ggcaagaatt gtggcttgag atctagatta   13980
cgtggaagaa aggtagtaaa agtagtagta taagtagtaa aaagaggtaa aaagagaaaa   14040
ccggctacat actagagaag cacgtacaca aaaactcata ggcacttcat catacgacag   14100
tttcttgatg cattataata gtgtattaga tattttcaga aatatgcata gaacctcttc   14160
ttgcctttac tttttataca tagaacattg gcagatttac ttacactact tgtttctac   14220 gccatttctt ttgttttcaa cacttagaca agttgttgag aaccggacta ctaaaaagca   14280
atgttcccac tgaaaatcat gtacctgcag gataataacc ccctaattct gcatcgatcc   14340
agtatgtttt ttttctcta ctcatttta cctgaagata gagcttctaa aacaaaaaaa   14400
atcagcgatt acatgcatat tgtgtgttct agaattgcgg atcaccagat cgccattaca   14460
atgtatgcag gcaaatattt ctcagaatga aaatagaga aaggaaacg aaaattctgt   14520 aagatgcctt cgaagagatt tctcgatatg caaggcgtgc atcagggtga tccaaaggaa   14580
ctcgagagag agggcgaaag gcaatttaat gcattgcttc tccattgact tctagttgag   14640
cggataagtt cggaaatgta agtcacagct aatgacaaat ccactttagg tttcgaggca   14700
```

```
ctatttaggc aaaaagacga gtggggaaat aacaaacgct caaacatatt agcatatacc    14760
ttcaaaaaat gggaatagta tataaccttc cggttcgtta ataaatcaaa tctttcatct    14820
agttctctta agatttcaat attttgcttt cttgaagaaa gaatctactc tcctccccca    14880
ttcgcactgc aaagctagct tggcactggc cgtcgtttta caacgtcgtg actgggaaaa    14940
ccctggcctt acccaactta atcgccttgc agcacatccc cctttcgcca gctggcgtaa    15000
tagcgaagag gcccgcaccg atcgcccttc ccaacagttg cgcagcctga atggcgaatg    15060
ggaaattgta aacgttaata ttttgttaaa attcgcgtta aattttttgtt aaatcagctc    15120
attttttaac cataggccg aaatcggcaa atcccttat aaatcaaaag aatagaccga    15180
gatagggttg agtgttgttc cagtttggaa caagagtcca ctattaaaga acgtggactc    15240
caacgtcaaa gggcgaaaaa ccgtctatca gggcgatggc ccactacgtg aaccatcacc    15300
ctaatcaagt ttttgggt cgaggtgccg taaagcacta atcggaacc ctaaagggag    15360
cccccgattt agagcttgac ggggaaagcc ggcgaacgtg gcgagaaagg aagggaagaa    15420
agcgaaagga gcgggcgcta gggcgctggc aagtgtagcg gtcacgctgc gcgtaaccac    15480
cacacccgcc gcgcttaatg cgccgctaca gggcgcgtca ggtggcactt tcggggaaa    15540
tgtgcgcgga acccctattt gtttattttt ctaaatacat tcaaatatgt atccgctcat    15600
gagacaataa ccctgataaa tgcttcaata atattgaaaa aggaagagta tgagtattca    15660
acatttccgt gtcgccctta ttcccttttt tgcggcattt tgccttcctg tttttgctca    15720
cccagaaacg ctggtgaaag taaaagatgc tgaagatcag ttgggtgcac gagtgggtta    15780
catcgaactg gatctcaaca gcggtaagat ccttgagagt tttcgccccg aagaacgttt    15840
tccaatgatg agcacttta aagttctgct atgtggcgcg gtattatccc gtattgacgc    15900
cgggcaagac caactcggtc gccgcataca ctattctcag aatgacttgg ttgagtactc    15960
accagtcaca gaaaagcatc ttacggatgg catgacagta agagaattat gcagtgctgc    16020
cataaccatg agtgataaca ctgcggccaa cttacttctg acaacgatcg gaggaccgaa    16080
ggagctaacc gcttttttgc acaacatggg ggatcatgta actcgccttg atcgttggga    16140
accggagctg aatgaagcca taccaaacga cgagcgtgac accacgatgc ctgtagcaat    16200
ggcaacaacg ttgcgcaaac tattaactgg cgaactactt agtctagctt cccggcaaca    16260
attaatagac tggatggagg cggataaagt tgcaggacca cttctgcgct cggcccttcc    16320
ggctggctgg tttattgctg ataaatctgg agccggtgag cgtgggtctc gcggtatcat    16380
tgcagcactg gggccagatg gtaagccctc ccgtatcgta gttatctaca cgacggggag    16440
tcaggcaact atggatgaac gaaatagaca gatcgctgag ataggtgcct cactgattaa    16500
gcattggtaa ctgtcagacc aagtttactc atatatactt tagattgatt taaaacttca    16560
tttttaattt aaaaggatct aggtgaagat cctttttgat aatctcatga ccaaaatccc    16620
ttaacgtgag ttttcgttcc actgagcgtc agacccgta gaaagatca aggatcttc    16680
ttgagatcct ttttttctgc gcgtaatctg ctgcttgcaa acaaaaaaac caccgctacc    16740
agcggtggtt tgtttgccgg atcaagagct accaactctt tttccgaagg taactggctt    16800
cagcagagcg cagataccaa atactgtcct tctagtgtag ccgtagttag gccaccactt    16860
caagaactct gtagcaccgc ctacatacct cgctctgcta atcctgttac cagtggctgc    16920
tgccagtggc gataagtcgt gtcttaccgg gttggactca agacgatagt taccggataa    16980
ggcgcagcgg tcgggctgaa cggggggttc gtgcacacag cccagcttgg agcgaacgac    17040
```

-continued

```
ctacaccgaa ctgagatacc tacagcgtga gcattgagaa agcgccacgc ttcccgaagg    17100
gagaaaggcg acaggtatcc cggtaagcgg cagggtcgga acaggagagc gcacgaggga    17160
gcttccaggg ggaaacgcct ggtatcttta tagtcctgtc gggtttcgcc acctctgact    17220
tgagcgtcga ttttgtgat gctcgtcagg ggggcggagc ctatggaaaa acgccagcaa    17280
cgcggccttt ttacggttcc tggccttttg ctggcctttt gctcacatgt tctttcctgc    17340
gttatcccct gattctgtgg ataaccgtat taccgccttt gagtgagctg ataccgctcg    17400
ccgcagccga acgaccgagc gcagcgagtc agtgagcgag gaagcggaag agcgcccaat    17460
acgcaaaccg cctctccccg cgcgttggcc gattcattaa tgcagctggc acgacaggtt    17520
tcccgactgg aaagcgggca gtgagcgcaa cgcaattaat gtgagttagc tcactcatta    17580
ggcaccccag gctttacact ttatgcttcc ggctcgtatg ttgtgtggaa ttgtgagcgg    17640
ataacaattt cacacaggaa acagctatga catgattacg aatttaatac gactcacaat    17700
agggaattag cttgcgcgaa attattggct tttttttttt tttaattaat actacctttt    17760
gatgtgaacg tttactaaag tagcactatc tgtggaatgg ctgttggaac ttttccgat    17820 taacagcttg tattccaagt cctgacattc cagttgtaag ttttccaact tgtgattcaa    17880
ttgttcaatc tcttggttaa aattctcttg ttccatgaat aggctctttt tccagtctcg    17940
aaattttgaa atttctctgt tggacagctc gttgaatttt tcttagctt ctaattgtct    18000 agttataaat tcaggatccc attctgtagc caccttatcc atgaccgttt tattaattat    18060
ttcatagcac ttgtaatttt tgagtttgtt ttcctcgatt tcatcgaagt tcatttcttc    18120
ctccaaaaat ttccttttgt cttccgttat gtcaacactt tcgttgtta agcaatctct    18180 ggcctttaat agcctagttc ttagcatttc agatc                               18215
```

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
tgatcttgta gaaagtaccg agg                                             23

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
ggaaacagct atgacatgat tacg                                            24

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
ggaaacagct atgacatgat tacg                                            24

<210> SEQ ID NO 5
<211> LENGTH: 25

```
<212> TYPE: DNA
<213> ORGANISM: Artificial Sequence
<220> FEATURE:
<223> OTHER INFORMATION: Synthetic primer

<400> SEQUENCE: 5
ctttgttctt ccgttatgtc aacac                                          25

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
ttccaagaag aacaacctga tag                                            23

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
tgatgtgaac gtttactaaa g                                              21

<210> SEQ ID NO 8
<211> LENGTH: 16176
<212> TYPE: DNA
<213> ORGANISM: Artificial Sequence
<220> FEATURE:
<223> OTHER INFORMATION: Synthetic plasmid

<400> SEQUENCE: 8
tcgcgcgttt cggtgatgac ggtgaaaacc tctgacaca tgcagctccc ggagacggtc       60
acagcttgtc tgtaagcgga tgccgggagc agacaagccc gtcagggcgc gtcagcgggt     120
gttggcgggt gtcggggctg gcttaactat gcggcatcag agcagattgt actgagagtg     180
caccatatgc ggtgtgaaat accgcacaga tgcgtaagga gaaaataccg catcaggcgc     240
cattcgccat tcaggctgcg caactgttgg gaagggcgat cggtgcgggc ctcttcgcta     300
ttacgccagc tggcgaaagg gggatgtgct gcaaggcgat taagttgggt aacgccaggg     360
ttttcccagt cacgacgttg taaaacgacg ccagtaagc ttgcatgcct gcaggtcgac      420
gcggccgcat attttttgta actgtaattt cactcatgca caagaaaaaa aaaactggat     480
taaaagggag cccaaggaaa actcctcagc atatatttag aagtctcctc agcatatagt     540
tgtttgtttt ctttacacat tcactgttta ataaacttt tataatatttt cattatcgga    600 actctagatt ctatacttgt ttcccaattg ggccgatcgg gccttgctgg tagtaaacgt     660
atacgtcata aaagggaaaa gccacatgcg gaagaatttt atggaaaaaa aaaaaacctc     720
gaagttacta cttctagggg gcctatcaag taaattactc ctggtacact gaagtatata     780
agggatatag aagcaaatag ttgtcagtgc aatccttcaa gacgattggg aaaatactgt     840
aggtaccgga gacctaacta catagtgttt aaagattacg gatatttaac ttacttagaa     900
taatgccatt ttttgagtt ataataatcc tacgttagtg tgagcgggat ttaaactgtg      960
aggaccttaa tacattcaga cacttctgcg gtatcaccct acttattccc ttcgagatta    1020
tatctaggaa cccatcaggt tggtggaaga ttacccgttc taagactttt cagcttcctc    1080
```

```
tattgatgtt acacctggac accccttttc tggcatccag tttttaatct tcagtggcat    1140
gtgagattct ccgaaattaa ttaaagcaat cacacaattc tctcggatac cacctcggtt    1200
gaaactgaca ggtggtttgt tacgcatgct aatgcaaagg agcctatata cctttggctc    1260
ggctgctgta acagggaata taagggcag cataatttag gagtttagtg aacttgcaac     1320
atttactatt ttcccttctt acgtaaatat ttttcttttt aattctaaat caatcttttt    1380
caatttttg tttgtattct tttcttgctt aaatctataa ctacaaaaaa cacatacata     1440
aactaaaaat gtctgaacca gctcaaaaga acaaaaggt tgctaacaac tctctagaac     1500
aattgaaagc ctccggcact gtcgttgttg ccgacactgg tgatttcggc tctattgcca    1560
agtttcaacc tcaagactcc acaactaacc catcattgat cttggctgct gccaagcaac    1620
caacttacgc caagttgatc gatgttgccg tggaatacgg taagaagcat ggtaagacca    1680
ccgaagaaca agtcgaaaat gctgtggaca gattgttagt cgaattcggt aaggagatct    1740
taaagattgt tccaggcaga gtctccaccg aagttgatgc tagattgtct tttgacactc    1800
aagctaccat tgaaaaggct agacatatca ttaaattgtt tgaacaagaa ggtgtctcca    1860
aggaaagagt ccttattaaa attgcttcca cttgggaagg tattcaagct gccaaagaat    1920
tggaagaaaa ggacggtatc cactgtaatt tgactctatt attctccttc gttcaagcag    1980
ttgcctgtgc cgaggcccaa gttactttga tttccccatt tgttggtaga attctagact    2040
ggtacaaatc cagcactggt aaagattaca agggtgaagc cgacccaggt gttatttccg    2100
tcaagaaaat ctacaactac tacaagaagt acggttacaa gactattgtt atgggtgctt    2160
cttttcagaag cactgacgaa atcaaaaact ggctggtgt tgactatcta acaatttctc    2220
cagctttatt ggacaagttg atgaacagta ctgaaccttt cccaagagtt ttggaccctg    2280
tctccgctaa aaggaagcc ggcgacaaga tttcttacat cagcgacgaa tctaaattca    2340
gattcgactt gaatgaagac gctatggcca ctgaaaaatt gtccgaaggt atcagaaaat    2400
tctctgccga tattgttact ctattcgact tgattgaaaa gaaagttacc gcttaaggaa    2460
gtatctcgga atattaatt taggccatgt ccttatgcac gtttcttttg atacttacgg    2520
gtacatgtac acaagtatat ctatatatat aaattaatga aaatccccta tttatatata    2580
tgactttaac gagacagaac agtttttat tttttatcct atttgatgaa tgatacagtt    2640
tcttattcac gtgttatacc cacaccaaat ccaatagcaa taccggccat cacaatcact    2700
gtttcggcag cccctaagat cagacaaaac atccggaacc accttaaatc aacgtcccat    2760
atgaatcctt gcagcaaagc cgctcgtacc ggagatatac aatagaacag ataccagaca    2820
agacataatg ggctaaacaa gactacacca attacactgc ctcattgatg gtggtacata    2880
acgaactaat actgtagccc tagacttgat agccatcatc atatcgaagt ttcactaccc    2940
ttttttccatt tgccatctat tgaagtaata ataggcgcat gcaacttctt ttctttttt     3000
ttctttctc tctcccccgt tgttgtctca ccatatccgc aatgacaaaa aaatgatgga    3060
agacactaaa ggaaaaaatt aacgacaaag acagcaccaa cagatgtcgt tgttccagag    3120
ctgatgaggg gtatctcgaa gcacacgaaa ctttttcctt ccttcattca cgcacactac    3180
tctctaatga gcaacggtat acggccttcc ttccagttac ttgaatttga aataaaaaaa    3240
agtttgctgt cttgctatca agtataaata gacctgcaat tattaatctt tgtttcctc     3300
gtcattgttc tcgttccctt tcttccttgt ttcttttttct gcacaatatt tcaagctata    3360
ccaagctac aatcaactat ctcatataca atgactcaat tcactgacat tgataagcta     3420
gccgtctcca ccataagaat tttggctgtg gacaccgtat ccaaggccaa ctcaggtcac    3480
```

```
ccaggtgctc cattgggtat ggcaccagct gcacacgttc tatggagtca aatgcgcatg    3540
aacccaacca acccagactg gatcaacaga gatagatttg tcttgtctaa cggtcacgcg    3600
gtcgctttgt tgtattctat gctacatttg actggttacg atctgtctat tgaagacttg    3660
aaacagttca gacagttggg ttccagaaca ccaggtcatc ctgaatttga gttgccaggt    3720
gttgaagtta ctaccggtcc attaggtcaa ggtatctcca acgctgttgg tatggccatg    3780
gctcaagcta acctggctgc cacttacaac aagccgggct ttaccttgtc tgacaactac    3840
acctatgttt tcttgggtga cggttgtttg caagaaggta tttcttcaga agcttcctcc    3900
ttggctggtc atttgaaatt gggtaacttg attgccatct acgatgacaa caagatcact    3960
atcgatggtg ctaccagtat ctcattcgat gaagatgttg ctaagagata cgaagcctac    4020
ggttgggaag ttttgtacgt agaaaatggt aacgaagatc tagccggtat tgccaaggct    4080
attgctcaag ctaagttatc caaggacaaa ccaactttga tcaaaatgac cacaaccatt    4140
ggttacggtt ccttgcatgc cggctctcac tctgtgcacg gtgccccatt gaaagcagat    4200
gatgttaaac aactaaagag caaattcggt ttcaacccag acaagtcctt tgttgttcca    4260
caagaagttt acgaccacta ccaaaagaca atttttaaagc aggtgtcga agccaacaac    4320 aagtggaaca agttgttcag cgaataccaa aagaaattcc cagaattagg tgctgaattg    4380
gctagaagat tgagcggcca actacccgca aattgggaat ctaagttgcc aacttacacc    4440
gccaaggact ctgccgtggc cactagaaaa ttatcagaaa ctgttcttga ggatgtttac    4500
aatcaattgc cagagttgat tggtggttct gccgatttaa accttctaa cttgaccaga    4560 tggaaggaag cccttgactt ccaacctcct tcttccggtt caggtaacta ctctggtaga    4620
tacattaggt acggtattag agaacacgct atgggtgcca taatgaacgg tatttcagct    4680
ttcggtgcca actacaaacc atacggtggt actttcttga acttcgtttc ttatgctgct    4740
ggtgccgtta gattgtccgc tttgtctggc cacccagtta tttgggttgc tacacatgac    4800
tctatcggtg tcggtgaaga tggtccaaca catcaaccta ttgaaacttt agcacacttc    4860
agatccctac caaacattca agtttggaga ccagctgatg gtaacgaagt ttctgccgcc    4920
tacaagaact ctttagaatc caagcatact ccaagtatca ttgctttgtc cagacaaaac    4980
ttgccacaat tggaaggtag ctctattgaa agcgcttcta agggtggtta cgtactacaa    5040
gatgttgcta acccagatat tattttagtg gctactggtt ccgaagtgtc tttgagtgtt    5100
gaagctgcta agactttggc cgcaaagaac atcaaggctc gtgttgtttc tctaccagat    5160
ttcttcactt ttgacaaaca accctagaa tacagactat cagtcttacc agacaacgtt    5220
ccaatcatgt ctgttgaagt tttggctacc acatgttggg gcaaatacgc tcatcaatcc    5280
ttcggtattg acagatttgg tgcctccggt aaggcaccag aagtcttcaa gttcttcggt    5340 ttcacccag aaggtgttgc tgaaagagct caaaagacca ttgcattcta taagggtgac    5400
aagctaattt ctcctttgaa aaaagctttc taaattctga tcgtagatca tcagatttga    5460
tatgatatta tttgtgaaaa aatgaaataa aactttatac aacttaaata caacttttttt    5520 tataaacgat taagcaaaaa aatagtttca aacttttaac aatattccaa acactcagtc    5580
cttttccttc ttatattata ggtgtacgta ttatagaaaa atttcaatga ttacttttc    5640 tttcttttc cttgtaccag cacatggccg agcttgaatg ttaaaccctt cgagagaatc    5700
acaccattca agtataaagc caataaagaa tatcgtacca gagaattttg ccatcggaca    5760
tgctacctta cgcttatatc tctcattgga atatcgtttt ctgattaaaa cacggaagta    5820
```

```
agaacttaat tcgttttccg ttgaactatg ttgtgccagc gtaacattaa aaaagagtgt    5880
acaaggccac gttctgtcac cgtcagaaaa atatgtcaat gaggcaagaa ccgggatggt    5940
aacaaaaatc acgatctggg tgggtgtggg tgtattggat tataggaagc cacgcgctca    6000
acctggaatt acaggaagct ggtaattttt tgggtttgca atcatcacca tctgcacgtt    6060
gttataatgt cccgtgtcta tatatatcca ttgacggtat tctattttt tgctattgaa    6120 atgagcgttt tttgttacta caattggttt tacagacgga attttcccta tttgtttcgt    6180 cccattttc cttttctcat tgttctcata tcttaaaaag gtcctttctt cataatcaat     6240
gctttctttt acttaatatt ttacttgcat tcagtgaatt ttaatacata ttcctctagt    6300
cttgcaaaat cgatttagaa tcaagatacc agcctaaaaa tggtcaaacc aattatagct    6360
cccagtatcc ttgcttctga cttcgccaac ttgggttgcg aatgtcataa ggtcatcaac    6420
gccggcgcag attggttaca tatcgatgtc atggacggcc attttgttcc aaacattact    6480
ctgggccaac caattgttac ctccctacgt cgttctgtgc cacgccctgg cgatgctagc    6540
aacacagaaa agaagcccac tgcgttcttc gattgtcaca tgatggttga aaatcctgaa    6600
aaatgggtcg acgattttgc taaatgtggt gctgaccaat ttacgttcca ctacgaggcc    6660
acacaagacc ctttgcattt agttaagttg attaagtcta agggcatcaa agctgcatgc    6720
gccatcaaac ctggtacttc tgttgacgtt ttatttgaac tagctcctca tttggatatg    6780
gctcttgtta tgactgtgga acctgggttt ggaggccaaa aattcatgga agacatgatg    6840
ccaaaagtgg aaactttgag agccaagttc ccccatttga atatccaagt cgatggtggt    6900
ttgggcaagg agaccatccc gaaagccgcc aaagccggtg ccaacgttat tgtcgctgga    6960
accagtgttt tcactgcagc tgacccgcac gatgttatct ccttcatgaa agaagaagtc    7020
tcgaaggaat tgcgttctag agatttgcta gattagttgt acatatgcgg catttcttat    7080
atttatactc tctatactat acgatatggt attttttct cgttttgatc tcctaatata    7140
cataaaccga gccattccta ctatacaaga tacgtaagtg cctaactcat gggaaaaatg    7200
ggccgcccag ggtggtgcct tgtccgtttt cgatgatcaa tccctgggat gcagtatcgt    7260
caatgacact ccataaggct tccttaacca aagtcaaaga actcttcttt tcattctctt    7320
tcactttctt accgccatct agatcaatat ccatttcgta ccccgcggaa ccgccagata    7380
ttcattactt gacgcaaaag cgtttgaaat aatgacgaaa aagaaggaag aaaaaaaaag    7440
aaaaataccg cttctaggcg ggttatctac tgatccgagc ttccactagg atagcaccca    7500
aacacctgca tatttggacg accttttactt acaccaccaa aaaccactttt cgcctctccc    7560 gcccctgata acgtccacta attgagcgat tacctgagcg gtcctctttt gtttgcagca    7620
tgagacttgc atactgcaaa tcgtaagtag caacgtctca aggtcaaaac tgtatggaaa    7680
ccttgtcacc tcacttaatt ctagctagcc taccctgcaa gtcaagaggt ctccgtgatt    7740
cctagccacc tcaaggtatg cctctccccg gaaactgtgg ccttttctgg cacacatgat    7800
ctccacgatt tcaacatata aatagctttt gataatggca atattaatca aatttatttt    7860
acttctttct tgtaacatct ctcttgtaat cccttattcc ttctagctat ttttcataaa    7920
aaaccaagca actgcttatc aacacacaaa cactaaatca aatggctgc cggtgtccca    7980 aaaattgatg cgttagaatc tttgggcaat ccttttggagg atgccaagag agctgcagca    8040
tacagagcag ttgatgaaaa atttaaaattt gatgatcaca aaattattgg aattggtagt    8100
ggtagcacag tggtttatgt tgccgaaaga attggacaat atttgcatga ccctaaattt    8160
tatgaagtag cgtctaaatt catttgcatt ccaacaggat tccaatcaag aaacttgatt    8220
```

```
ttggataaca agttgcaatt aggctccatt gaacagtatc ctcgcattga tatagcgttt    8280
gacggtgctg atgaagtgga tgagaattta caattaatta aaggtggtgg tgcttgtcta    8340
tttcaagaaa aattggttag tactagtgct aaaaccttca ttgtcgttgc tgattcaaga    8400
aaaaagtcac caaacatttt aggtaagaac tggaggcaag gtgttcccat tgaaattgta    8460
ccttcctcat acgtgagggt caagaatgat ctattagaac aattgcatgc tgaaaaagtt    8520
gacatcagac aaggaggttc tgctaaagca ggtcctgttg taactgacaa taataacttc    8580
attatcgatg cggatttcgg tgaaatttcc gatccaagaa aattgcatag agaaatcaaa    8640
ctgttagtgg gcgtggtgga acaggtttta ttcatcgaca acgcttcaaa agcctacttc    8700
ggtaattctg acggtagtgt tgaagttacc gaaaagtgag cagatcaaag gcaaagacag    8760
aaaccgtagt aaaggttgac ttttcacaac agtgtctcca tttttatat tgtattatta    8820 aagctattta gttatttgga tactgttttt tttccagaag ttttcttttt agtaaagtac    8880
aatccagtaa aaatgaagga tgaacaatcg gtgtatgcag attcaacacc aataaatgca    8940
atgtttattt ctttggaacg tttgtgttgt tcgaaatcca ggataatcct tcaacaagac    9000
cctgtccgga taaggcgtta ctaccgatga cacaccaagc tcgagtaacg gagcaagaat    9060
tgaaggatat ttctgcacta aatgccaaca tcagatttaa tgatccatgg acctggttgg    9120
atggtaaatt ccccactttt gcctgatcca gccagtaaaa tccatactca acgacgatat    9180
gaacaaattt ccctcattcc gatgctgtat atgtgtataa attttacat gctcttctgt    9240 ttagacacag aacagcttta aataaaatgt tggatatact ttttctgcct gtggtgtcat    9300
ccacgctttt aattcatctc ttgtatggtt gacaatttgg ctattttta acagaaccca    9360 acggtaattg aaattaaaag ggaaacgagt gggggcgatg agtgagtgat actaaaatag    9420
acaccaagag agcaaagcgg tcccagcggc cgcgaattcg gcgtaatcat ggtcatagct    9480
gtttcctgtg tgaaattgtt atccgctcac aattccacac aacatacgag ccggaagcat    9540
aaagtgtaaa gcctggggtg cctaatgagt gagctaactc acattaattg cgttgcgctc    9600
actgcccgct ttccagtcgg gaaacctgtc gtgccagctg cattaatgaa tcggccaacg    9660
cgcggggaga ggcggtttgc gtattgggcg ctcttccgct tcctcgctca ctgactcgct    9720
gcgctcggtc gttcggctgc ggcgagcggt atcagctcac tcaaaggcgg taatacggtt    9780
atccacagaa tcaggggata acgcaggaaa gaacatgtga gcaaaaggcc agcaaaaggc    9840
caggaaccgt aaaaaggccg cgttgctggc gttttccat aggctccgcc cccctgacga    9900
gcatcacaaa aatcgacgct caagtcagag gtggcgaaac ccgacaggac tataaagata    9960
ccaggcgttt ccccctggaa gctccctcgt gcgctctcct gttccgaccc tgccgcttac   10020
cggatacctg tccgcctttc tcccttcggg aagcgtggcg ctttctcaat gctcacgctg   10080
taggtatctc agttcggtgt aggtcgttcg ctccaagctg ggctgtgtgc acgaaccccc   10140
cgttcagccc gaccgctgcg ccttatccgg taactatcgt cttgagtcca acccggtaag   10200
acacgactta tcgccactgg cagcagccac tggtaacagg attagcagag cgaggtatgt   10260
aggcggtgct acagagttct tgaagtggtg gcctaactac ggctacacta aaggacagt   10320 atttggtatc tgcgctctgc tgaagccagt taccttcgga aaaagagttg gtagctcttg   10380
atccggcaaa caaaccaccg ctggtagcgg tggtttttt gtttgcaagc agcagattac   10440
gcgcagaaaa aaaggatctc aagaagatcc tttgatcttt tctacggggt ctgacgctca   10500
gtggaacgaa aactcacgtt aagggatttt ggtcatgaga ttatcaaaaa ggatcttcac   10560
```

```
ctagatcctt ttaaattaaa aatgaagttt taaatcaatc taaagtatat atgagtaaac   10620
ttggtctgac agttaccaat gcttaatcag tgaggcacct atctcagcga tctgtctatt   10680
tcgttcatcc atagttgcct gactccccgt cgtgtagata actacgatac gggagggctt   10740
accatctggc cccagtgctg caatgatacc gcgagaccca cgctcaccgg ctccagattt   10800
atcagcaata aaccagccag ccggaagggc cgagcgcaga agtggtcctg caactttatc   10860
cgcctccatc cagtctatta attgttgccg ggaagctaga gtaagtagtt cgccagttaa   10920
tagtttgcgc aacgttgttg ccattgctac aggcatcgtg gtgtcacgct cgtcgtttgg   10980
tatggcttca ttcagctccg gttcccaacg atcaaggcga gttacatgat cccccatgtt   11040
gtgcaaaaaa gcggttagct ccttcggtcc tccgatcgtt gtcagaagta agttggccgc   11100
agtgttatca ctcatggtta tggcagcact gcataattct cttactgtca tgccatccgt   11160
aagatgcttt tctgtgactg gtgagtactc aaccaagtca ttctgagaat agtgtatgcg   11220
gcgaccgagt tgctcttgcc cggcgtcaat acgggataat accgcgccac atagcagaac   11280
tttaaaagtg ctcatcattg gaaaacgttc ttcggggcga aaactctcaa ggatcttacc   11340
gctgttgaga tccagttcga tgtaacccac tcgtgcaccc aactgatctt cagcatcttt   11400
tactttcacc agcgtttctg ggtgagcaaa aacaggaagg caaaatgccg caaaaaaggg   11460
aataagggcg acacggaaat gttgaatact catactcttc cttttcaat attattgaag   11520 catttatcag ggttattgtc tcatgagcgg atacatattt gaatgtattt agaaaaataa   11580
acaaataggg gttccgcgca catttccccg aaaagtgcca cctgacgtca actatacaaa   11640
tgacaagttc ttgaaaacaa gaatcttttt attgtcagta ctgattagaa aaactcatcg   11700
agcatcaaat gaaactgcaa tttattcata tcaggattat caataccata ttttgaaaa   11760 agccgtttct gtaatgaagg agaaaactca ccgaggcagt tccataggat ggcaagatcc   11820
tggtatcggt ctgcgattcc gactcgtcca acatcaatac aacctattaa tttcccctcg   11880
tcaaaaataa ggttatcaag tgagaaatca ccatgagtga cgactgaatc cggtgagaat   11940
ggcaaaagct tatgcatttc tttccagact tgttcaacag gccagccatt acgctcgtca   12000
tcaaaatcac tcgcatcaac caaaccgtta ttcattcgtg attgcgcctg agcgagacga   12060
aatacgcgat cgctgttaaa aggacaatta caaacaggaa tcgaatgcaa ccggcgcagg   12120
aacactgcca gcgcatcaac aatattttca cctgaatcag gatattcttc taatacctgg   12180
aatgctgttt tgccggggat cgcagtggtg agtaaccatg catcatcagg agtacggata   12240
aaatgcttga tggtcggaag aggcataaat tccgtcagcc agtttagtct gaccatctca   12300
tctgtaacat cattggcaac gctacctttg ccatgtttca gaaacaactc tggcgcatcg   12360
ggcttcccat acaatcgata gattgtcgca cctgattgcc cgacattatc gcgagcccat   12420
ttatacccat ataaatcagc atccatgttg gaatttaatc gcggcctcga acgtgagtc   12480 ttttccttac ccatggttgt ttatgttcgg atgtgatgtg agaactgtat cctagcaaga   12540
ttttaaaagg aagtatatga agaagaacc tcagtggcaa atcctaacct tttatatttc   12600
tctacagggg cgcggcgtgg ggacaattca acgcgactgt gacgcgttct agaacacaca   12660
atatgcatgt aatcgctgat ttttttgtt ttagaagctc tatcttcagg taaaaatgag   12720
tagagaaaaa aaaacatact ggatcgatgc agaattaggg ggttattatc ctgcaggtac   12780
atgattttca gtgggaacat tgctttttag tagtccggtt ctcaacaact tgtctaagtg   12840
ttgaaaacaa aagaaatggc gtagaaacaa agtagtgtaa gtaaatctgc caatgttcta   12900
tgtataaaaa gtaaaggcaa gaagaggttc tatgcatatt tctgaaaata tctaatacac   12960
```

```
tattataatg catcaagaaa ctgtcgtatg atgaagtgcc tatgagtttt tgtgtacgtg    13020
cttctctagt atgtagccgg tttctctttt ttacctctttt ttactactta tactactact    13080
tttactacct ttcttccacg taatctagat ctcaagccac aattcttgcc ctatgctcca    13140
acgtatacaa catcgaagaa gagtctttct ttagggagtc attggaaaag atagtatgat    13200
ggtattcgat ttacctatgt cgcaaaagaa agtccggggc aacaccacag aatgctttct    13260
ctgtactaat aacctgttgt gcgcttaacg gtctaatcgt taatcagcgg tggttaaatt    13320
tttgtaaatc taatgttcca tgattttctt tcttcaaaag gaacatgtag cgaaaatctt    13380 tttttactt tgatacactg caattgtttc tgagcatgct gaaattttct cgatgttttt    13440
tttttttatt ggcatccaag taattaatcc ttatgctacg aaaaagttgt aggaatgaat    13500
catgcataat ctaacggata tcatcatata ctctgtgcta atattctaaa caagttcgaa    13560
aatattttct tggcccatgt aataggtggt aagtgtattg ctttgatagg aacgtcatta    13620
tcgcacaaga caatcggcac taataaccgt ttaaatatta tcatgcatgt atacatcagt    13680
atctcataga aatatacctg taagtacata cttatctaag tataaattct cgacctatgg    13740
agtcaccaca tttcccagca acttccccac ttcctctgca atcgccaacg tcctctcttc    13800
actgagtctc cgtccgataa cctgcactgc aaccggtgcc ccatggtacg cctccggatc    13860
atactcttcc tgcacgaggg catcaagctc actaaccgcc ttgaaactct cattcttctt    13920
atcgatgttc ttatccgcaa aggtaaccgg aacaaccacg ctcgtgaaat ccagcaggtt    13980
gatcacagag gcatacccat agtaccggaa ctggtcatgc cgtaccgcag cggtaggcgt    14040
aatcggcgcg atgatggcgt ccagttcctt cccggccttt tcttcagcct cccgccattt    14100
ctcaaggtac tccatctggt aattccactt ctggagatgc gtgtcccaga gctcgttcat    14160
gttaacagct ttgatgttcg ggttcagtag gtctttgata tttggaatcg ccggctcgcc    14220
ggatgcactg atatcgcgca ttacgtcggc gctgccgtca gccgcgtaga tatgggagat    14280
gagatcgtgg ccgaaatcgt gcttgtatgg cgtccacggg gtcacggtgt gaccggcttt    14340
ggcgagtgcg gcgacggtgg ttccacgcc gcgcaggata ggagggtgtg gaaggacatt    14400
gccgtcgaag ttgtagtagc cgatattgag cccgccgttc ttgatcttgg aggcaataat    14460
gtccgactcg gactggcgcc agggcatggg gatgaccttg gagtcgtatt ccatggctc    14520 ctgaccgagg acggatttgg tgaagaggcg gaggtcctca acagagtgcg taatcggccc    14580
gacaacgctg tgcaccgtct cctgaccctc catgctgttc gccatctttg catacggcag    14640
ccgcccatga ctcggcctta gaccgtacag gaagttgaac gcggccggca ctcgaatcga    14700
gccaccgata tccgttccta caccgatgac gccaccacga atcccaacga tcgcaccctc    14760
accaccagaa ctgccgccgc acgaccagtt cttgttgcgt gggttgacgg tgcgcccgat    14820
gatgttgttg actgtctcgc agaccatcag ggtctgcggg acagaggtct tgacgtagaa    14880
gacggcaccg gctttgcgga gcatggttgt cagaaccgag tccccttcgt cgtacttgtt    14940
tagccatgag atgtagccca ttgatgtttc gtagcccttg actcgaagct ggtctttgag    15000
agagatgggg aggccatgga gtggaccaac gggtctcttg tgctttgcgt agtattcatc    15060 gagttcccctt gcctgcgcga gagcggcgtc agggaagaac tcgtgggcgc agtttgttaa    15120
ctgctgggcg attgctgccc gtttacagaa tgctagcgta acttccaccg aggtcaactc    15180 tccgccgcc agcttggaca caagatctgc agcggaggcc tctgtgatct tcagttcggc    15240
ctctgaaagg atccccgatt tctttgggaa atcaataacg ctgtcttccg caggcagcgt    15300
```

```
ctggactttc cattcatcag ggatggtttt tgcgaggcgg gcgcgcttat cagcggccag    15360
ttcttcccag gattgaggca ttgtatatga gatagttgat tgtatgcttg gtatagcttg    15420
aaatattgtg cagaaaaaga acaaggaag aaagggaacg agaacaatga cgaggaaaca     15480
aaagattaat aattgcaggt ctatttatac ttgatagcaa agcggcaaac ttttttttatt   15540 tcaaattcaa gtaactggaa ggaaggccgt ataccgttgc tcattagaga gtagtgtgcg    15600
tgaatgaagg aaggaaaaag tttcgtgtgt tcgaagatac ccctcatcag ctctggaaca    15660
acgacatctg ttggtgctgt ctttgtcgtt aattttttcc tttagtgtct tccatcattt    15720
tttttgtcat tgcggatatg gtgagacaac aacgggggag agagaaaaga aaaaaaaga    15780 aaagaagttg catgcgccta ttattacttc aatagatggc aaatggaaaa agggtagtga    15840
aacttcgata tgatgatggc tatcaagtct agggctacag tattagttcg ttatgtacca    15900
ccatcaatga ggcagtgtaa tttgtgtagt cttgtttagc ccattatgtc ttgtctggta    15960
tctgttctat tgtatatctc ccctccgcca cctacatgtt agggagacca acgaaggtat    16020
tataggaatc ccgatgtatg ggtttggttg ccagaaaaga ggaagtccat attgtacacc    16080
cggaaacaac aaaaggatgg gcccatgacg tctaagaaac cattattatc atgacattaa    16140
cctataaaaa taggcgtatc acgaggccct ttcgtc                              16176
```

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
acgccagggt tttcccagtc ac                                                22

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
ccagcaccct aagccgacta gg                                                22

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
caccaacctg atgggttcct ag                                                22

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
acggtgctga tgaagtggat g                                                 21

```
<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
accacgccca ctaacagttt g                                              21

<210> SEQ ID NO 14
<211> LENGTH: 16580
<212> TYPE: DNA
<213> ORGANISM: Artificial Sequence
<220> FEATURE:
<223> OTHER INFORMATION: Synthetic plasmid

<400> SEQUENCE: 14
taaaagaaaa cattctctag ggattacgag gtaaagatac attttcaagg cttattcgat     60
tctgtgaact cagttggaat attaagggac aggttgtttc cttgcaccca gagaagcaat    120
atcgttgagc atgttcgaca ttgcgtatcc ttggatgaaa gacgtggaaa attcaagcag    180
ttatgtttca ctccgatgcc gtacattccg aaactatttt cattgacata ttgtaatcat    240
ataactgacc agtgttcgcc ggtgccaact tctaatgcat taatgcgtga tctaaccccg    300
gaaaatcctt tgataaaata cactttaaaa agtggcgcac attctattag taatccttct    360
ccactcattc ctgataaccc tggaaggttg ttatcgagca aaagcgagga aactacagag    420
ttgctgttgg acctgaactc attcttagaa ggtaattcat acgcgagaga tacagaatgt    480
tcaacaagag gaattgaagc cattttccaa cttcaatcta tccaaggcag cggtacatca    540
agtagaatga ctatgacacc cgacttgatt gaaaaatggt ttccaggtga tcggccatct    600
tggccgatca ttctgacgtt ggtggaggtt gggcgcctga ctgtgagaca aagagaact    660 tgtcaaattt aacgctgcga tggattttag cagaggcaat caaatttggt gttaaattca    720
aacctggtgc aatacatgat ttcgctacca acacacttc gattggatct ttattcgcag    780
acacacatga ttaccttagt ttcaactcac caaagaaatg ttccctacta ggagtgagtg    840
ataatgagga tggagcccga gaggataaat ctggcagaaa tgagagaatg gaagattgtc    900
taaaaaatat aaaagagact agattgagct tgaaagatga aaagaaaaa gtgaaggatg    960 cttttactct taaatgtgga catgcaaata aatttatgag attggtgtgg tgggtattgg   1020
aactgctccc cattggaata cgaatggaaa ataagaagg aaagtggcaa aattttcata   1080
cacctaacct cggaagatcg tcgacaagct tgtggagagg tgacttcatg aaccaagtgt   1140
ctgtcgatat acaacaaaaa ggaaccattt tcatcttgat ggacaacatg tgcatcaaaa   1200
accttatcgt aaagagttct tggacccttg gatggagtgt aaaccatgat ttaaaacagc   1260
aaataataaa aatcgatagc gacaaaaact gtcaatttca atattcttta tatttgttga   1320
ctgcttagat attttgagaa aattcagcgg aaacagcgtg atgagtgagt taagttctgc   1380
tgtttaaata agtattcaac tactattgaa gccgactcat gaagccggtt acggacaaaa   1440
ccgggcaaat ttcgccggtc ccggaatttt cgtttccgca ataaaagaac cgctcatcat   1500
catagcgcca gggtagtata ctatagaagg tcagactaaa ctgagtcatc tagagtaatg   1560
acgccttagt agcttttaca tcttcataag aaaaggaaac ttgtagaatg gcctggcgat   1620
ttgtttgctt tcttgtgatg aagaaatttc gatgcgatta accggcaaaa tcagtaaagg   1680
tatttcgcgg aggcggcctt caatcatcga atactacgtc ttaatatgat gtactgtggt   1740
```

-continued

```
tcatattttc aagtagtgtt agtaaatttg tatacgttca tgtaagtgtg tatcttgagt    1800
gtctgtatgg gcgcataaac gtaagcgaga cttccaaatg gagcaaacga gaagagatct    1860
ttaaagtatt atagaagagc tgggcaggaa ctattatgac gtaaagcctt gaccataata    1920
aagacgattc tttgtccctc tatacaaaca tcttgcaaag ataccaaata ttttcaaatc    1980
ctactcaata aaaaattaat gaataaatta gtgtgtgtgc attatatata ttaaaaatta    2040
agaattagac taaataaagt gtttctaaaa aaatattaaa gttgaaatgt gcgtgttgtg    2100
aattgtgctc tattagaata attatgactt gtgtgcgttt catattttaa aataggaaat    2160
aaccaagaaa gaaaagtac catccagaga aaccaattat atcaaatcaa ataaaacaac     2220
cagcttcggt gtgtgtgtgt gtgtgaagct aagagttgat gccatttaat ctaaaaattt    2280
taaggtgtgt gtgtggataa aatattagaa tgacaattcc ccggaattgc gtacgcccgg    2340
gtcgcgaccg cggcttaaca gtacatgttg acaatggctt cgtacaattc ttgcttacca    2400
gaagtttgct ttggttcacc gttagccttg gcgtaagcaa ccaaatcttc caaagtcaac    2460
ttaccatctt caaattcctt acccttacca gagtcgaaag aagcgtatct gtcagccaac    2520
atcttcttgt aaggagattc ttccaataat ttagcagcag attccaaagc tctggccatg    2580
acatccatac cggcaatgtg agcgatgaag atatcttcca gtcagtagaa gtttcttctg    2640
gtcttagcat cgaagttggt accaccgtta ccgaaaccac cgtttctgat gatttgcatc    2700
atagcttgag tcaattcaaa gttgtcgatt ggaattggt cggtgtccca accgttttgg     2760
tagtcacctc tgttagcatc aatggaaccc aacataccgt tgtcgacagc aacagccaat    2820
tcgtgttcga aagtgtgacc ggccaaagta gcgtggttga cttcgatgtt gaccttgaag    2880
tccttgtcca agttgtgagc cttcaagaaa ccgatgacag tttcggtgtc aacatcgtat    2940
tggtgcttgg ttggttccat tggctttggt tcaatcaaga agtacccctt gaaacctctg    3000
gcacgagcgt agtcacgagc aatggtcaac atttgagcca agtgttcctt ttctctcttt    3060
tggtcagtgt tcaacaagga catgtaacct tctctaccac cccagaaaac gtagttggaa    3120
ccacctaatt caatggtagc atcgatggcg ttcttgattt ggatggcagc tctggcaaca    3180
acatcgaaat ctgggttggt agcggcaccg ttcatgtatc tggcatgacc aaagacgtta    3240
gcagtacccc ataatagctt gataccagtt tcagcttgct tttgcttagc gtaagcaaca    3300
atttccttca agttagcttc gtattcttcg atggtttcag cttcttcaca caagtcaaca    3360
tcgtggaaac agtagtattc aatacccatc ttttgcataa attcgaaacc agcgtccatc    3420
ttgttcttag cagcttggac cttgtcagct tcaccgttcc atgggaattt cttggtacca    3480
ccaccgaatt ggtcaccacc ttcagcacac aaggtatgcc accaagccat agcgaacttt    3540
aaccattcag acatcttctt acccatgata accttgtcag catcgtagta tctgaaggcc    3600
attgggttct tggattcctt accttcgaat tgatcttac caataccctgg gaagtattcc     3660 ttggtagcca ttttttagttt atgtatgtgt ttttactagt tatagattta agcaagaaaa    3720
gaatacaaac aaaaaattga aaaagattga tttagaatta aaaagaaaaa tatttacgta    3780
agaagggaaa atagtaaatg ttgcaagttc actaaactcc taaattatgc tgcccttttat    3840 attccctgtt acagcagccg agccaaaggt ataggctc ctttgcatta gcatgcgtaa      3900
caaaccacct gtcagtttca accgaggtgg tatccgagag aattgtgtga ttgctttaat    3960
taatttcgga gaatctcaca tgccactgaa gattaaaaac tggatgccag aaaaggggtg    4020
tccaggtgta acatcaatag aggaagctga aaagtcttag aacgggtaat cttccaccaa    4080
cctgatgggt tcctagatat aatctcgaag ggaataagta gggtgatacc gcagaagtgt    4140
```

```
ctgaatgtat taaggtcctc acagtttaaa tcccgctcac actaacgtag gattattata    4200
actcaaaaaa atggcattat tctaagtaag ttaaatatcc gtaatcttta aacactatgt    4260
agttaggtct cgggcccag cgccagtagg gttgttgagc ttagtaaaaa tgtgcgcacc     4320
acaagcctac atgactccac gtcacatgaa accacaccgt ggggccttgt tgcgctagga    4380
ataggatatg cgacgaagac gcttctgctt agtaaccaca ccacattttc aggggggtcga   4440
tctgcttgct tcctttactg tcacgagcgg cccataatcg cgcttttttt ttaaaaggcg    4500
cgagacagca aacaggaagc tcgggtttca accttcggag tggtcgcaga tctggagact    4560
ggatctttac aatacagtaa ggcaagccac catctgcttc ttaggtgcat gcgacggtat    4620
ccacgtgcag aacaacatag tctgaagaag gggggagga gcatgttcat tctctgtagc     4680
agtaagagct tggtgataat gaccaaaact ggagtctcga aatcatataa atagacaata    4740
tattttcaca caatgagatt tgtagtacag ttctattctc tctcttgcat aaataagaaa    4800
ttcatcaaga acttggtttg atatttcacc aacacacaca aaaacagta cttcactaaa     4860
tttacacaca aaacaaaatg ttgtgttcag taattcagag acagacaaga gaggtttcca    4920
acacaatgtc tttagactca tactatcttg ggtttgatct ttcgacccaa caactgaaat    4980
gtctcgccat taaccaggac ctaaaaattg tccattcaga aacagtggaa tttgaaaagg    5040
atcttccgca ttatcacaca aagaagggtg tctatataca cggcgacact atcgaatgtc    5100
ccgtagccat gtggttagag gctctagatc tggttctctc gaaatatcgc gaggctaaat    5160
ttccattgaa caaagttatg gccgtctcag ggtcctgcca gcagcacggg tctgtctact    5220
ggtcctccca agccgaatct ctgttagagc aattgaataa gaaaccggaa aaagatttat    5280
tgcactacgt gagctctgta gcatttgcaa ggcaaaccgc ccccaattgg caagaccaca    5340
gtactgcaaa gcaatgtcaa gagtttgaag agtgcatagg tgggcctgaa aaaatggctc    5400
aattaacagg gtccagagcc catttttagat ttactggtcc tcaaattctg aaaattgcac   5460
aattagaacc agaagcttac gaaaaaacaa agaccatttc tttagtgtct aatttttga     5520
cttctatctt agtgggccat cttgttgaat tagaggaggc agatgcctgt ggtatgaacc    5580
tttatgatat acgtgaaaga aaattcagtg atgagctact acatctaatt gatagttctt    5640
ctaaggataa aactatcaga caaaaattaa tgagagcacc catgaaaaat ttgatagcgg    5700
gtaccatctg taaatatttt attgagaagt acggtttcaa tacaaactgc aaggtctctc    5760
ccatgactgg ggataattta gccactatat gttcttttacc cctgcggaag aatgacgttc    5820
tcgtttccct aggaacaagt actacagttc ttctggtcac cgataagtat cacccctctc    5880
cgaactatca tcttttcatt catccaactc tgccaaacca ttatatgggt atgatttgtt    5940
attgtaatgg ttctttggca agggagagga taagagacga gttaaacaaa gaacgggaaa    6000
ataattatga gaagactaac gattggactc ttttttaatca agctgtgcta gatgactcag    6060
aaagtagtga aaatgaatta ggtgtatatt ttcctctggg ggagatcgtt cctagcgtaa    6120
aagccataaa caaagggtt atcttcaatc caaaaacggg tatgattgaa agagaggtgg     6180
ccaagttcaa agacaagagg cacgatgcca aaaatattgt agaatcacag gctttaagtt    6240
gcagggtaag aatatctccc ctgctttcgg attcaaacgc aagctcacaa cagagactga    6300
acgaagatac aatcgtgaag tttgattacg atgaatctcc gctgcgggac tacctaaata    6360
aaaggccaga aaggactttt tttgtaggtg gggcttctaa aaacgatgct attgtgaaga    6420
agtttgctca agtcattggt gctacaaagg gtaatttag gctagaaaca ccaaactcat     6480
```

```
gtgcccttgg tggttgttat aaggccatgt ggtcattgtt atatgactct aataaaattg    6540
cagttccttt tgataaattt ctgaatgaca attttccatg gcatgtaatg gaaagcatat    6600
ccgatgtgga taatgaaaat tgggatcgct ataattccaa gattgtcccc ttaagcgaac    6660
tggaaaagac tctcatctaa aatatgtttg aataatttat catgccctga caagtacaca    6720
caaacacaga cacataatat acatacatat atatatatca ccgttattat gcgtgcacat    6780
gacaatgccc ttgtatgttt cgtatactgt agcaagtagt catcattttg ttccccgttc    6840
ggaaaatgac aaaaagtaaa atcaataaat gaagagtaaa aaacaattta tgaaagggtg    6900
agcgaccagc aacgagagag acaaatcaaa ttagcgcttt ccagtgagaa tataagagag    6960
cattgaaaga gctaggttat acgcgtgaag atctcgttat gtacccgaat atgtcagttt    7020
acattggtca gtctattgga gaattaagtt tgatcgtagg tatagaccgg acaatatgcc    7080
ggaatatgta aggcaattgt tccaagattt ggaaggtatt gatttaaaaa gtaataaagt    7140
ttcaaataaa tatgataagc aagataatag caacgggagt gaaatcaatg ggggcttttt    7200
tgataatgag gaagggcagg aactccacat gggtcaaaaa gcaagttatt ttgcaacgac    7260
atacaattca agattatttg acagtaaata ctcccaatta aaaagaaat tcatggactg    7320 ggatagtaat tcctggacag atattccaga tgatttaaaa atatacctac agcaagatga    7380
atcgctttag cattaaaaaa acccccttcgg tacgtaatat aaaaaatttt ataggtaata    7440
tacatatata aaaatacttc aatcattttt acaatcttgt atactttata caacatgtga    7500
aatcttctgc ttctggacat caatattcaa atacaggcca atcttaggta aaacatttgg    7560
agaaaagaag dataaggcag gacgagggaa gataaatagt ttcgttaatt ataaatacat    7620
gcagataaat aaaggaatat caaatattat gaatagaaaa agaagatggt gagacaaaaa    7680
agtagtaata aataggtcca aatcttcttt atttcccctt tcttttctta tccttttgtt    7740
ttctccatat tgtataagaa tatattctta ggaaaatcaa cagggaatac agtatagtga    7800
ttttcgttcc ttttttgagcg taatcccttc gagactgtga tgttgattat ttttgttgtg    7860
atttcaaaat tcttaggtta gttgtatagt tcccgttcat aacataatgg atagtaaatg    7920
aaaaatcaaa ataagggtga aacaaataga caataaagat gtagttttcg aggacgaaaa    7980
acaaacctaa ccaacaatga ccttatcacc atcgaattca taagcaggaa tttctaagtt    8040
taagggggca ggtccctttc tgattctacc ggaaatatca taatgtgaac catggcaagg    8100
acagaaccaa ccaccaaaat caccggcttc accaattgga acacaaccta agtgagtaca    8160
aatacccagc ataattaacc attgagggtc tttgactctg tcagcatcgg tctgtgggtc    8220
cttcaaagcg gacatatcca cactgttggc ttcctgaatt tcatgaggag ttctgtgtct    8280
aatgaacaca ggcttacctt gccatttgac aaccacgttt ttacccaatg ggatagccgc    8340
taaattaact tcaactttag ccatagccaa aacatcggca gtagcggtca tagatgaaat    8400
aaaggtttct acggttgatt tggcacctgc agatgacaaa agacccatag caccgaccat    8460
aaagtaagca taagaacggc ctttatcagc atcgttattt tcctttaaaa cgtcatcaaa    8520
atttggggtc ctgtacgtgg atttgctagc cagcaaagat tgagaaatca ggtaccacgg    8580
ctcctcgctg cagacctgcg agcagggaaa cgctcccctc acagtcgcgt tgaattgtcc    8640
ccacgccgcg cccctgtaga gaaatataaa aggttaggat ttgccactga ggttcttctt    8700
tcatatactt ccttttaaaa tcttgctagg atacagttct cacatcacat ccgaacataa    8760
acaaccatgg gtaaggaaaa gactcacgtt tcgaggccgc gattaaattc caacatggat    8820
gctgatttat atgggtataa atgggctcgc gataatgtcg ggcaatcagg tgcgacaatc    8880
```

-continued

```
tatcgattgt atgggaagcc cgatgcgcca gagttgtttc tgaaacatgg caaaggtagc    8940
gttgccaatg atgttacaga tgagatggtc agactaaact ggctgacgga atttatgcct    9000
cttccgacca tcaagcattt tatccgtact cctgatgatg catggttact caccactgcg    9060
atccccggca aaacagcatt ccaggtatta aagaatatc ctgattcagg tgaaaatatt     9120
gttgatgcgc tggcagtgtt cctgcgccgg ttgcattcga ttcctgtttg taattgtcct    9180
tttaacagcg atcgcgtatt tcgtctcgct caggcgcaat cacgaatgaa taacggtttg    9240
gttgatgcga gtgattttga tgacgagcgt aatggctggc ctgttgaaca agtctggaaa    9300
gaaatgcata agcttttgcc attctcaccg gattcagtcg tcactcatgg tgatttctca    9360
cttgataacc ttattttga cgagggaaa ttaataggtt gtattgatgt tggacgagtc      9420
ggaatcgcag accgatacca ggatcttgcc atcctatgga actgcctcgg tgagttttct    9480
ccttcattac agaaacggct ttttcaaaaa tatggtattg ataatcctga tatgaataaa    9540
ttgcagtttc atttgatgct cgatgagttt ttctaatcag tactgacaat aaaaagattc    9600
ttgttttcaa gaacttgtca tttgtatagt tttttatat tgtagttgtt ctattttaat     9660
caaatgttag cgtgatttat attttttttc gcctcgacat catctgccca gatgcgaagt    9720
taagtgcgca gaaagtaata tcatgcgtca atcgtatgtg aatgctggtc gctatactgc    9780
tgtcgattcg atactaacgc cgccatccag ggtaccatcc ttttgttgtt tccgggtgta    9840
caatatggac ttcctctttt ctggcaacca aacccataca tcgggattcc tataatacct    9900
tcgttggtct ccctaacatg taggtggcgg aggggagata tacaatagaa cagataccag    9960
acaagacata atgggctaaa caagactaca caaattacac tgcctcattg atggtggtac   10020
ataacgaact aatactgtag ccctagactt gatagccatc atcatatcga agtttcacta   10080
cccttttcc atttgccatc tattgaagta ataataggcg catgcaactt ctttctttt      10140
tttttctttt ctctctcccc cgttgttgtc tcaccatatc cgcaatgaca aaaaaaatga   10200
tggaagacac taaggaaaa aattaacgac aaagacagca ccaacagatg tcgttgttcc     10260
agagctgatg aggggtatct tcgaacacac gaaactttt ccttccttca ttcacgcaca    10320
ctactctcta atgagcaacg gtatacggcc ttccttccag ttacttgaat ttgaaataaa   10380
aaaagtttgc cgctttgcta tcaagtataa atagacctgc aattattaat cttttgtttc   10440
ctcgtcattg ttctcgttcc ctttcttcct tgtttctttt tctgcacaat atttcaagct   10500
ataccaagca tacaatcaac tatctcatat acaatgcctc aatcctggga agaactggcc   10560
gctgataagc gcgcccgcct cgcaaaaacc atccctgatg aatggaaagt ccagacgctg   10620
cctgcggaag acagcgttat tgatttccca agaaatcgg ggatcctttc agaggccgaa    10680
ctgaagatca cagaggcctc cgctgcagat cttgtgtcca agctggcggc cggagagttg   10740
acctcggtgg aagttacgct agcattctgt aaacgggcag caatcgccca gcagttaaca   10800
aactgcgccc acgagttctt ccctgacgcc gctctcgcgc aggcaaggga actcgatgaa   10860
tactacgcaa agcacaagag acccgttggt ccactccatg gcctccccat ctctctcaaa   10920
gaccagcttc gagtcaaggg ctacgaaaca tcaatgggct acatctcatg gctaaacaag   10980
tacgacgaag gggactcggt tctgacaacc atgctccgca aagccggtgc cgtcttctac   11040
gtcaagacct ctgtcccgca gaccctgatg gtctgcgaga cagtcaacaa catcatcggg   11100
cgcaccgtca acccacgcaa caagaactgg tcgtgcggcg cagttctgg tggtgagggt    11160
gcgatcgttg ggattcgtgg tggcgtcatc ggtgtaggaa cggatatcgg tggctcgatt   11220
```

```
cgagtgccgg ccgcgttcaa cttcctgtac ggtctaaggc cgagtcatgg gcggctgccg   11280
tatgcaaaga tggcgaacag catggagggt caggagacgg tgcacagcgt tgtcgggccg   11340
attacgcact ctgttgagga cctccgcctc ttcaccaaat ccgtcctcgg tcaggagcca   11400
tggaaatacg actccaaggt catccccatg ccctggcgcc agtccgagtc ggacattatt   11460
gcctccaaga tcaagaacgg cgggctcaat atcggctact acaacttcga cggcaatgtc   11520
cttccacacc ctcctatcct gcgcggcgtg gaaaccaccg tcgccgcact cgccaaagcc   11580
ggtcacaccg tgaccccgtg gacgccatac aagcacgatt tcggccacga tctcatctcc   11640
catatctacg cggctgacgg cagcgccgac gtaatgcgcg atatcagtgc atccggcgag   11700
ccggcgattc caaatatcaa agacctactg aacccgaaca tcaaagctgt taacatgaac   11760
gagctctggg acacgcatct ccagaagtgg aattaccaga tggagtacct tgagaaatgg   11820
cgggaggctg aagaaaaggc cgggaaggaa ctggacgcca tcatcgcgcc gattacgcct   11880
accgctgcgg tacggcatga ccagttccgg tactatgggt atgcctctgt gatcaacctg   11940
ctggatttca cgagcgtggt tgttccggtt acctttgcgg ataagaacat cgataagaag   12000
aatgagagtt tcaaggcggt tagtgagctt gatgccctcg tgcaggaaga gtatgatccg   12060
gaggcgtacc atggggcacc ggttgcagtg caggttatcg gacggagact cagtgaagag   12120
aggacgttgg cgattgcaga ggaagtgggg aagttgctgg gaaatgtggt gactccatag   12180
gtcgagaatt tatacttaga taagtatgta cttacaggta tatttctatg agatactgat   12240
gtatacatgc atgataatat ttaaacggtt attagtgccg attgtcttgt gcgataatga   12300
cgttcctatc aaagcaatac acttaccacc tattacatgg gccaagaaaa tattttcgaa   12360
cttgtttaga atattagcac agagtatatg atgatatccg ttagattatg catgattcat   12420
tcctacaact ttttcgtagc ataaggatta attacttgga tgccaataaa aaaaaaaaac   12480
atcgagaaaa tttcagcatg ctcagaaaca attgcagtgt atcaaagtaa aaaaagatt   12540 ttcgctacat gttccttttg aagaaagaaa atcatggaac attagattta caaaaattta   12600
accaccgctg attaacgatt agaccgttaa gcgcacaaca ggttattagt acagagaaag   12660
cattctgtgg tgttgccccg gactttcttt tgcgacatag gtaaatcgaa taccatcata   12720
ctatcttttc caatgactcc ctaaagaaag actcttcttc gatgttgtat acgttggagc   12780
atagggcaag aattgtggct tgagatctag attacgtgga agaaaggtag taaaagtagt   12840
agtataagta gtaaaaagag gtaaaaagag aaaaccggct acatactaga gaagcacgta   12900
cacaaaaact cataggcact tcatcatacg acagtttctt gatgcattat aatagtgtat   12960
tagatatttt cagaaatatg catagaacct cttcttgcct ttacttttta tacatagaac   13020
attggcagat ttacttacac tactttgttt ctacgccatt tcttttgttt tcaacactta   13080
gacaagttgt tgagaaccgg actactaaaa agcaatgttc ccactgaaaa tcatgtacct   13140
gcaggataat aacccctaa ttctgcatcg atccagtatg ttttttttc tctactcatt   13200 tttacctgaa gatagagctt ctaaaacaaa aaaaatcagc gattacatgc atattgtgtg   13260
ttctagaatt gcggatcacc agatcgccat tacaatgtat gcaggcaaat atttctcaga   13320
atgaaaaata gagaaaagga aacgaaaatt ctgtaagatg ccttcgaaga gatttctcga   13380
tatgcaaggc gtgcatcagg gtgatccaaa ggaactcgag agagagggcg aaaggcaatt   13440
taatgcattg cttctccatt gacttctagt tgagcggata agttcggaaa tgtaagtcac   13500
agctaatgac aaatccactt taggtttcga ggcactattt aggcaaaaag acgagtgggg   13560
aaataacaaa cgctcaaaca tattagcata taccttcaaa aaatgggaat agtatataac   13620
```

```
cttccggttc gttaataaat caaatctttc atctagttct cttaagatttt caatattttg   13680 cttctcttgaa gaaagaatct actctcctcc cccattcgca ctgcaaagct agcttggcac   13740
tggccgtcgt tttacaacgt cgtgactggg aaaaccctgg ccttacccaa cttaatcgcc   13800
ttgcagcaca tcccccttc gccagctggc gtaatagcga agaggcccgc accgatcgcc    13860
cttcccaaca gttgcgcagc ctgaatggcg aatgggaaat tgtaaacgtt aatattttgt   13920
taaaattcgc gttaaatttt tgttaaatca gctcattttt taaccaatag gccgaaatcg   13980
gcaaaatccc ttataaatca aaagaataga ccgagatagg gttgagtgtt gttccagttt   14040
ggaacaagag tccactatta agaacgtgg actccaacgt caagggcga aaaccgtct      14100 atcagggcga tggcccacta cgtgaaccat caccctaatc aagttttttg gggtcgaggt   14160
gccgtaaagc actaaatcgg aaccctaaag ggagcccccg atttagagct tgacggggaa   14220
agccggcgaa cgtggcgaga aggaaggga agaaagcgaa aggagcgggc gctagggcgc     14280
tggcaagtgt agcggtcacg ctgcgcgtaa ccaccacacc cgccgcgctt aatgcgccgc   14340
tacagggcgc gtcaggtggc acttttcggg gaaatgtgcg cggaacccct atttgtttat   14400
ttttctaaat acattcaaat atgtatccgc tcatgagaca ataaccctga taaatgcttc   14460
aataatattg aaaaaggaag agtatgagta ttcaacattt ccgtgtcgcc cttattccct   14520 ttttttgcggc attttgcctt cctgtttttg ctcacccaga aacgctggtg aaagtaaaag   14580
atgctgaaga tcagttgggt gcacgagtgg gttacatcga actggatctc aacagcggta   14640
agatccttga gagttttcgc cccgaagaac gttttccaat gatgagcact tttaaagttc   14700
tgctatgtgg cgcggtatta tcccgtattg acgccgggca agaccaactc ggtcgccgca   14760
tacactattc tcagaatgac ttggttgagt actcaccagt cacagaaaag catcttacgg   14820
atggcatgac agtaagagaa ttatgcagtg ctgccataac catgagtgat aacactgcgg   14880
ccaacttact tctgacaacg atcggaggac cgaaggagct aaccgctttt ttgcacaaca   14940
tgggggatca tgtaactcgc cttgatcgtt gggaaccgga gctgaatgaa gccataccaa   15000
acgacgagcg tgacaccacg atgcctgtag caatggcaac aacgttgcgc aaactattaa   15060
ctggcgaact acttagtcta gcttcccggc aacaattaat agactggatg gaggcggata   15120
aagttgcagg accacttctg cgctcggccc ttccggctgg ctggtttatt gctgataaat   15180
ctggagccgg tgagcgtggg tctcgcggta tcattgcagc actggggcca gatggtaagc   15240
cctcccgtat cgtagttatc tacacgacgg ggagtcaggc aactatggat gaacgaaata   15300
gacagatcgc tgagataggt gcctcactga ttaagcattg gtaactgtca gaccaagttt   15360
actcatatat actttagatt gatttaaaac ttcattttta atttaaaagg atctaggtga   15420
agatcctttt tgataatctc atgaccaaaa tcccttaacg tgagttttcg ttccactgag   15480
cgtcagaccc cgtagaaaag atcaaaggat cttcttgaga tcctttttt ctgcgcgtaa   15540 tctgctgctt gcaaacaaaa aaaccaccgc taccagcggt ggtttgtttg ccggatcaag   15600
agctaccacc tcttttccg aaggtaactg gcttcagcag agcgcagata ccaaatactg   15660
tccttctagt gtagccgtag ttaggccacc acttcaagaa ctctgtagca ccgcctacat   15720
acctcgctct gctaatcctg ttaccagtgg ctgctgccag tggcgataag tcgtgtctta   15780
ccgggttgga ctcaagacga tagttaccgg ataaggcgca gcggtcgggc tgaacggggg   15840
gttcgtgcac acagcccagc ttggagcgaa cgacctacac cgaactgaga tacctacagc   15900
gtgagcattg agaaagcgcc acgcttcccg aagggagaaa ggcggacagg tatccggtaa   15960
```

```
gcggcagggt cggaacagga gagcgcacga gggagcttcc aggggggaaac gcctggtatc    16020 tttatagtcc tgtcgggttt cgccacctct gacttgagcg tcgattttg tgatgctcgt     16080 caggggggcg gagcctatgg aaaaacgcca gcaacgcggc cttttacgg ttcctggcct     16140 tttgctggcc ttttgctcac atgttctttc ctgcgttatc ccctgattct gtggataacc    16200
gtattaccgc ctttgagtga gctgataccg ctcgccgcag ccgaacgacc gagcgcagcg    16260
agtcagtgag cgaggaagcg gaagagcgcc caatacgcaa accgcctctc cccgcgcgtt    16320
ggccgattca ttaatgcagc tggcacgaca ggtttcccga ctggaaagcg ggcagtgagc    16380
gcaacgcaat taatgtgagt tagctcactc attaggcacc ccaggcttta cactttatgc    16440
ttccggctcg tatgttgtgt ggaattgtga gcggataaca atttcacaca ggaaacagct    16500
atgacatgat tacgaattta atacgactca caatagggaa ttagcttgcg cgaaattatt    16560
ggcttttttt ttttttaat                                                16580

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
ccaaggcagc ggtacatcaa gtag                                          24

<210> SEQ ID NO 16
<211> LENGTH: 23
<212> TYPE: DNA
<213> ORGANISM: Artificial Sequence
<220> FEATURE:
<223> OTHER INFORMATION: Synthetic primer

<400> SEQUENCE: 16
tgcacatgtt gtccatcaag atg                                           23

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
ggaaacagct atgacatgat tacg                                          24

<210> SEQ ID NO 18
<211> LENGTH: 23
<212> TYPE: DNA
<213> ORGANISM: Artificial Sequence
<220> FEATURE:
<223> OTHER INFORMATION: synthetic primer

<400> SEQUENCE: 18
gtagcgaaat catgtattgc acc                                           23

<210> SEQ ID NO 19
<211> LENGTH: 120
<212> TYPE: DNA
<213> ORGANISM: Artificial Sequence
<220> FEATURE:
<223> OTHER INFORMATION: synthetic primer

<400> SEQUENCE: 19
```

```
tttctcatgg tagcgcctgt gcttcggtta cttctaagga agtccacaca aatcaagatc    60
cgttagacgt ttcagcttcc aaaacagaag aatgtgagac gctggggccc gagacctaac   120
```

<210> SEQ ID NO 20
<211> LENGTH: 120
<212> TYPE: DNA
<213> ORGANISM: Artificial Sequence
<220> FEATURE:
<223> OTHER INFORMATION: synthetic primer

<400> SEQUENCE: 20

```
ggaggtggta ctgaagcagg ttgaggagag gcatgatggg ggttctctgg aacagctgat    60
gaagcaggtg ttgttgtctg ttgagagtta gccttagtgt tgtggagagg tgacttcatg   120
```

<210> SEQ ID NO 21
<211> LENGTH: 120
<212> TYPE: DNA
<213> ORGANISM: Artificial Sequence
<220> FEATURE:
<223> OTHER INFORMATION: synthetic primer

<400> SEQUENCE: 21

```
tttctcatgg tagcgcctgt gcttcggtta cttctaagga agtccacaca aatcaagatc    60
cgttagacgt ttcagcttcc aaaacagaag aatgtgagag ctcccctcac agacgcgttg   120
```

<210> SEQ ID NO 22
<211> LENGTH: 120
<212> TYPE: DNA
<213> ORGANISM: Artificial Sequence
<220> FEATURE:
<223> OTHER INFORMATION: synthetic primer

<400> SEQUENCE: 22

```
gaggtggtac tgaagcaggt tgaggagagg catgatgggg gttctctgga acagctgatg    60
aagcaggtgt tgttgtctgt tgagagttag ccttagtgca atgacaagt tcttgaaaac   120
```

<210> SEQ ID NO 23
<211> LENGTH: 22
<212> TYPE: DNA
<213> ORGANISM: Artificial Sequence
<220> FEATURE:
<223> OTHER INFORMATION: synthetic primer

<400> SEQUENCE: 23

```
caccgttagc cttggcgtaa gc                                              22
```

<210> SEQ ID NO 24
<211> LENGTH: 21
<212> TYPE: DNA
<213> ORGANISM: Artificial Sequence
<220> FEATURE:
<223> OTHER INFORMATION: synthetic primer

<400> SEQUENCE: 24

```
cactttcgaa cacgaattgg c                                               21
```

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 25
gttacgtcgc cttggacttc g                                           21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
cggcaatacc tgggaacatg g                                           21
```